(12) United States Patent
Hanna

(10) Patent No.: US 10,195,218 B2
(45) Date of Patent: Feb. 5, 2019

(54) CRYSTALLIZATION METHOD AND BIOAVAILABILITY

(71) Applicant: GRUNENTHAL GMBH, Aachen (DE)

(72) Inventor: Mazen Hanna, Lutz, FL (US)

(73) Assignee: GRUNENTHAL GMBH (DE)

( * ) Notice: Subject to any disclaimer, the term of this patent is extended or adjusted under 35 U.S.C. 154(b) by 0 days.

(21) Appl. No.: 15/609,641

(22) Filed: May 31, 2017

(65) Prior Publication Data

US 2018/0000847 A1 Jan. 4, 2018

Related U.S. Application Data

(60) Provisional application No. 62/343,509, filed on May 31, 2016.

(51) Int. Cl.

| A61K 31/4164 | (2006.01) |
|---|---|
| A61K 31/663 | (2006.01) |
| C07D 233/56 | (2006.01) |
| A61K 31/198 | (2006.01) |
| A61K 31/662 | (2006.01) |
| A61K 9/20 | (2006.01) |
| A61K 9/48 | (2006.01) |

(52) U.S. Cl.
CPC .......... *A61K 31/663* (2013.01); *A61K 31/198* (2013.01); *A61K 31/4164* (2013.01); *A61K 31/662* (2013.01); *A61K 9/20* (2013.01); *A61K 9/48* (2013.01)

(58) Field of Classification Search
CPC . A61K 31/4164; A61K 31/663; C07D 233/56
USPC .......................................... 514/399; 548/112
See application file for complete search history.

(56) References Cited

U.S. PATENT DOCUMENTS

| 3,959,361 | A | 5/1976 | Krueger et al. |
|---|---|---|---|
| 3,961,934 | A | 6/1976 | Ratts |
| 4,939,130 | A | 7/1990 | Jaeggi et al. |
| 5,431,920 | A | 7/1995 | Bechard |
| 5,512,552 | A | 4/1996 | Sohda et al. |
| 6,468,559 | B1 | 10/2002 | Chen et al. |
| 6,476,006 | B2 | 11/2002 | Flashner-Barak et al. |
| 6,541,454 | B1 | 4/2003 | Breuer et al. |
| 6,676,965 | B1 | 1/2004 | Lulla et al. |
| 6,676,970 | B2 | 1/2004 | Bader et al. |
| 6,677,320 | B2 | 1/2004 | Diederich et al. |
| 6,936,275 | B2 | 8/2005 | Fassihi et al. |
| 7,008,640 | B2 | 3/2006 | Watanabe et al. |
| 7,011,847 | B2 | 3/2006 | Lulla et al. |
| 7,038,083 | B2 | 5/2006 | Lidor-Hadas et al. |
| 7,192,938 | B2 | 3/2007 | Bauss et al. |
| 7,309,698 | B2 | 12/2007 | Boyd et al. |
| 7,332,603 | B2 | 2/2008 | De Ferra et al. |
| 7,345,088 | B2 | 3/2008 | Green et al. |
| 7,354,912 | B2 | 4/2008 | Lichtenberger |
| 7,410,957 | B2 | 8/2008 | Bauss et al. |
| 7,411,087 | B2 | 8/2008 | Patel et al. |
| 7,425,549 | B2 | 9/2008 | Little et al. |
| 7,435,827 | B2 | 10/2008 | Aronhime et al. |
| 7,439,385 | B2 | 10/2008 | Deshpande et al. |
| 7,473,684 | B2 | 1/2009 | Harrison et al. |
| 7,528,280 | B2 | 5/2009 | Danda et al. |
| 7,582,768 | B2 | 9/2009 | Aronhime et al. |
| 7,589,211 | B2 | 9/2009 | Aronhime et al. |
| 7,645,459 | B2 | 1/2010 | Dansereau et al. |
| 7,645,460 | B2 | 1/2010 | Dansereau et al. |
| 7,687,636 | B2 | 3/2010 | Aronhime et al. |
| 7,704,977 | B2 | 4/2010 | Leonard |
| 7,718,634 | B2 | 5/2010 | Bauss et al. |
| 7,820,722 | B2 | 10/2010 | Raoof et al. |
| 8,053,429 | B2 | 11/2011 | Cumming et al. |
| 8,119,159 | B2 | 2/2012 | Cumming et al. |
| 8,158,153 | B2 | 4/2012 | Liversidge et al. |
| 8,399,023 | B2 | 3/2013 | Hanna et al. |
| 9,169,279 | B2 * | 10/2015 | Hanna ................. C07F 9/65061 |
| 9,334,296 | B2 | 5/2016 | Hanna et al. |
| 9,340,565 | B2 | 5/2016 | Hanna et al. |
| 2002/0142996 | A1 | 10/2002 | Okuno et al. |
| 2003/0064966 | A1 | 4/2003 | Palepu |
| 2003/0091623 | A1 | 5/2003 | Cumming et al. |
| 2003/0181421 | A1 | 9/2003 | Horowitz et al. |
| 2004/0127466 | A1 | 7/2004 | Palepu |
| 2004/0157798 | A1 | 8/2004 | Little |
| 2004/0157799 | A1 | 8/2004 | Seaman |
| 2004/0176327 | A1 | 9/2004 | Okuno et al. |
| 2004/0220264 | A1 | 11/2004 | Yu et al. |

(Continued)

FOREIGN PATENT DOCUMENTS

| AR | 080072 | 3/2012 |
|---|---|---|
| AU | 2011218625 A1 | 9/2011 |

(Continued)

OTHER PUBLICATIONS

Tidy, Dr. Colin, Seronegative Arthropathies, https://patient.info/doctor/seronegative-arthropathies, Apr. 16, 2014.*
International Search Report and Written Opinion in International Application No. PCT/US2016/052492, dated Dec. 16, 2016.
Morris et al., "An integrated approach to the selection of optimal salt form for a new drug candidate", International Journal of Pharmaceutics, 1994, 105, 209-217.
Bronner, "Intestinal Calcium Absorption: Mechanisms and Applications," J. Nutr. 1347-1352 (1987).
Bronner, "Current Concepts of Calcium Absorption: An Overview," J. Nutr. 122:642-643 (1992).
Dupuis et al., "Does the Inihbition of Microvillus Protein Phosphorylation by Lysine Explain the Activity of the Latter on Calcium Transfer?" J. Biochem. 13:1163-1170 (1981).
Dupuis et al., "Enterocyte Microvillus Can Phosphorylate Molecules Which Inhibit Endogenous Phosphorylation of its Proteins," Archives Internationales de Physiologie et de Biochimie 92:1-11 (1984).

(Continued)

*Primary Examiner* — Brenda L Coleman

(74) *Attorney, Agent, or Firm* — J.A. Lindeman & Co., PLLC

(57) ABSTRACT

Preparation, in-vitro and in vivo characterization of novel forms of (1-hydroxy-2-imidazol-1-yl-1-phosphono-ethyl) phosphonic acid, suitable for pharmaceutical compositions in drug delivery systems for humans.

19 Claims, 43 Drawing Sheets

(56) References Cited

U.S. PATENT DOCUMENTS

| | | |
|---|---|---|
| 2004/0230076 A1 | 11/2004 | Lifshitz-Liron et al. |
| 2005/0054616 A1 | 3/2005 | Aronhime et al. |
| 2005/0260262 A1 | 11/2005 | Dansereau et al. |
| 2006/0068010 A1 | 3/2006 | Turner et al. |
| 2006/0069069 A1 | 3/2006 | Kajander et al. |
| 2006/0173009 A1 | 8/2006 | Kanoh et al. |
| 2006/0178439 A1 | 8/2006 | Mohakhud et al. |
| 2006/0210639 A1 | 9/2006 | Liversidge |
| 2007/0015736 A1 | 1/2007 | Glausch et al. |
| 2007/0021389 A1 | 1/2007 | Aronhime et al. |
| 2007/0021616 A1 | 1/2007 | Aronhime et al. |
| 2007/0021617 A1 | 1/2007 | Aronhime et al. |
| 2007/0021618 A1 | 1/2007 | Aronhime et al. |
| 2007/0021619 A1 | 1/2007 | Aronhime et al. |
| 2007/0049557 A1 | 3/2007 | Ahmed et al. |
| 2007/0088161 A1 | 4/2007 | Stockel et al. |
| 2007/0134319 A1 | 6/2007 | Zannou et al. |
| 2007/0196464 A1 | 8/2007 | Cumming et al. |
| 2007/0218130 A1 | 9/2007 | Ahmed et al. |
| 2007/0225258 A1 | 9/2007 | Walsh |
| 2007/0238707 A1 | 10/2007 | Leonard |
| 2008/0090784 A1 | 4/2008 | Labriola et al. |
| 2008/0139514 A1 | 6/2008 | Gore et al. |
| 2008/0153784 A1 | 6/2008 | Zhang et al. |
| 2008/0153785 A1 | 6/2008 | Shin et al. |
| 2008/0167271 A1 | 7/2008 | Masini-Eteve |
| 2008/0249069 A1 | 10/2008 | Bauss et al. |
| 2008/0254089 A1 | 10/2008 | Glausch et al. |
| 2008/0255366 A1 | 10/2008 | Mohakhud et al. |
| 2008/0275001 A1 | 11/2008 | Cumming et al. |
| 2008/0286359 A1 | 11/2008 | Dansereau et al. |
| 2008/0287400 A1 | 11/2008 | Dansereau et al. |
| 2009/0023683 A1 | 1/2009 | Kocherlakota et al. |
| 2009/0075941 A1 | 3/2009 | Selander et al. |
| 2009/0082312 A1 | 3/2009 | Czarnik |
| 2009/0137808 A1 | 5/2009 | Samsel et al. |
| 2009/0209763 A1 | 8/2009 | Lidor-Hadas et al. |
| 2009/0215729 A1 | 8/2009 | Johnson et al. |
| 2009/0238876 A1 | 9/2009 | Danenberg et al. |
| 2009/0281064 A1 | 11/2009 | Ahmed et al. |
| 2010/0029596 A1 | 2/2010 | Ryu et al. |
| 2010/0047306 A1 | 2/2010 | Loeffler et al. |
| 2010/0056481 A1 | 3/2010 | Glausch et al. |
| 2010/0086593 A1 | 4/2010 | Dansereau et al. |
| 2010/0113394 A1 | 5/2010 | Dansereau et al. |
| 2010/0113395 A1 | 5/2010 | Dansereau et al. |
| 2010/0119559 A1 | 5/2010 | Dansereau et al. |
| 2010/0215743 A1 | 8/2010 | Leonard |
| 2010/0248640 A1 | 9/2010 | Macnaughtan et al. |
| 2011/0028435 A1 | 2/2011 | Hanna et al. |
| 2011/0182985 A1 | 7/2011 | Coughlan et al. |
| 2011/0263537 A1 | 10/2011 | Desai |
| 2012/0190647 A1 | 7/2012 | Hanna et al. |
| 2013/0303488 A1 | 11/2013 | Tabuteau |
| 2014/0349974 A1* | 11/2014 | Tabuteau ............ A61K 31/675 514/94 |
| 2015/0306116 A1 | 10/2015 | Hanna et al. |
| 2016/0016982 A1 | 1/2016 | Hanna et al. |

FOREIGN PATENT DOCUMENTS

| | | |
|---|---|---|
| AU | 2010278860 A1 | 2/2012 |
| CN | 103070668 | 5/2013 |
| CN | 102070668 B | 7/2013 |
| EP | 1154761 A1 | 11/2001 |
| EP | 1392325 A1 | 3/2004 |
| EP | 1567533 A2 | 8/2005 |
| EP | 1591122 A1 | 11/2005 |
| EP | 1612212 A1 | 1/2006 |
| EP | 1880744 A1 | 1/2008 |
| EP | 1925621 A1 | 5/2008 |
| JP | 2003-520240 | 7/2003 |
| JP | 2004-528303 A | 9/2004 |
| JP | 2008-533173 A | 8/2008 |
| WO | WO 92/14474 A1 | 9/1992 |
| WO | WO 95/08331 A1 | 3/1995 |
| WO | WO 96/07417 A1 | 3/1996 |
| WO | WO 97/05903 A2 | 2/1997 |
| WO | WO 98/52547 A1 | 11/1998 |
| WO | WO 98/56360 A2 | 12/1998 |
| WO | WO 00/21541 A1 | 4/2000 |
| WO | WO 00/50012 A1 | 8/2000 |
| WO | WO 00/61111 A1 | 10/2000 |
| WO | WO 00/64516 A1 | 11/2000 |
| WO | WO 01/52859 A1 | 7/2001 |
| WO | WO 01/82903 A1 | 11/2001 |
| WO | WO 01/97788 A2 | 12/2001 |
| WO | WO 02/080933 A1 | 10/2002 |
| WO | WO 02/087554 A2 | 11/2002 |
| WO | WO 02/089816 A1 | 11/2002 |
| WO | WO 03/007916 A1 | 1/2003 |
| WO | WO 03/051373 A1 | 6/2003 |
| WO | WO 2004/024165 A1 | 3/2004 |
| WO | WO 2004/035061 A1 | 4/2004 |
| WO | WO 2004/056373 A1 | 7/2004 |
| WO | WO 2004/075860 A2 | 9/2004 |
| WO | WO 2004/078161 A1 | 9/2004 |
| WO | WO 2004/078163 A2 | 9/2004 |
| WO | WO 2004/100941 A1 | 11/2004 |
| WO | WO 2005/000404 A2 | 1/2005 |
| WO | WO 2005/005447 A2 | 1/2005 |
| WO | WO 2005/025551 A2 | 3/2005 |
| WO | WO 2005/037157 A1 | 4/2005 |
| WO | WO 2005/044831 A2 | 5/2005 |
| WO | WO 2005/048979 A2 | 6/2005 |
| WO | WO 2005/063218 A2 | 7/2005 |
| WO | WO 2005/063717 A1 | 7/2005 |
| WO | WO 2005/099676 A2 | 10/2005 |
| WO | WO 2005/115331 A2 | 12/2005 |
| WO | WO 2006/018033 A1 | 2/2006 |
| WO | WO 2006/019843 A1 | 2/2006 |
| WO | WO 2006/020009 A1 | 2/2006 |
| WO | WO 2006/039499 A2 | 4/2006 |
| WO | WO 2006/066067 A2 | 6/2006 |
| WO | WO 2006/080780 A1 | 8/2006 |
| WO | WO 2006/102117 A1 | 9/2006 |
| WO | WO 2006/112889 A1 | 10/2006 |
| WO | WO 2007/016982 A1 | 2/2007 |
| WO | WO 2007/023342 A2 | 3/2007 |
| WO | WO 2007/032808 A1 | 3/2007 |
| WO | WO 2007/069049 A2 | 6/2007 |
| WO | WO 2007/093226 A1 | 8/2007 |
| WO | WO 2007/117706 A2 | 10/2007 |
| WO | WO 2007/125521 A2 | 11/2007 |
| WO | WO 2007/146234 A2 | 12/2007 |
| WO | WO 2008/040763 A1 | 4/2008 |
| WO | WO 2008/058722 A1 | 5/2008 |
| WO | WO 2008/064849 A1 | 6/2008 |
| WO | WO 2008/085281 A1 | 7/2008 |
| WO | WO 2008/100767 A1 | 8/2008 |
| WO | WO 2008/113177 A1 | 9/2008 |
| WO | WO 2009/018834 A1 | 2/2009 |
| WO | WO 2009/035265 A2 | 3/2009 |
| WO | WO 2009/040818 A1 | 4/2009 |
| WO | WO 2009/042179 A1 | 4/2009 |
| WO | WO 2009/056952 A1 | 5/2009 |
| WO | WO 2009/068567 A1 | 6/2009 |
| WO | WO 2009/072119 A2 | 6/2009 |
| WO | WO 2009/107850 A2 | 9/2009 |
| WO | WO 2009/112493 A1 | 9/2009 |
| WO | WO 2009/121935 A2 | 10/2009 |
| WO | WO 2010/014765 A1 | 2/2010 |
| WO | WO 2010/014766 A1 | 2/2010 |
| WO | WO 2010/060619 A1 | 6/2010 |
| WO | WO 2010/071866 A2 | 6/2010 |
| WO | WO 2010/099255 A1 | 9/2010 |
| WO | WO 2011/014781 A1 | 2/2011 |
| WO | WO 2011/097269 A1 | 8/2011 |
| WO | WO 2011/097269 A9 | 8/2011 |
| WO | WO 2011/132826 A1 | 10/2011 |
| WO | WO 2012/071517 A2 | 5/2012 |

(56) References Cited

FOREIGN PATENT DOCUMENTS

WO    WO 2015/051327 A1    4/2015
WO       2017/049294 A1    3/2017

OTHER PUBLICATIONS

Gueguen et al., "The Bioavailability of Dietary Calcium," J. Am. Col. Nutr. 19(2):119S-136S (2000).
Wasserman et al., "The Influence of Amino Acids and Other Organic Compounds on the Gastrointestinal Absorption of Calcium and Strontium in the Rat," J. Nutr. 371-383 (1956).
Atelvia Prescribing Information, revised Oct. 2010.
International Search Report and Written Opinion for PCT International Application No. PCT/US2010/043916, dated Sep. 27, 2010.
International Search Report and Written Opinion of PCT PCT/US11/23427 dated Apr. 22, 2011.
PCT International Search Report of PCT International Application No. PCT/US2010/043892, dated Feb. 11, 2011.
Written Opinion of the International Searching Authority of PCT International Application No. PCT/US2020/043892, dated Feb. 11, 2011.
PCT International Search Report and Written Opinion of PCT International Application No. PCT/US2011/062050, dated Apr. 10, 2012.
European Search Report for PCT/US2010/043916 dated Jan. 15, 2013.
Supplemental European Search Report for PCT/US2011/023427, dated Dec. 10, 2013.
McNamara et al. "Use of Glutaric Acid Cocrystal to Improve Bioavailability of a Low Solubility API," Pharmaceutical Research, Aug. 2006, vol. 23, No. 8, pp. 1888-1897; p. 1899, para. 4; p. 1889, para 8 to p. 1890, para 1; p. 1891, Fig. 4; p. 1894, para 2.
Coleman et al., "The Effects of Adding Zoledronic Acid to Neoadjuvant Chemotherapy on Tumor Response: Exploratory Evidence for Direct Anti-Tumor Activity in Breast Cancer," British J Cancer 102(7):1099-1105 (2010).
Davies et al., "Evaluating the Effects of Zolendronic Acid (ZOL) on Overall Survival (OS) in Patients (Pts) with Multiple Myeloma (MM): Results of the Medical Research Council (MRC) Myeloma IX Study," J Clinical Oncology 28(15): Abstract 8021 (2010).
Gnant et al., "Endocrine Therapy Plus Zolendronic Acid in Premenopausal Breast Cancer," New Englang J Medicine 360(17):679-691 2009).
Sorbera et al., "Zolendronate Disodium. Treatment of Tumor-Induced Hypercalcemia, Angiogenesis Inhibitor," Drugs of the Future, 25(3):259-268 (2000).
Patent Examination Report in Australian Application No. 2012216632 dated Aug. 14, 2014.
Office Action for JP Application No. 2012-552048 dated Sep. 17, 2014.
International Preliminary Report on Patentability in PCT application No. PCT/US2010/043892 dated Feb. 9, 2012.
International Search Report in PCT application No. PCT/US2011/023427 dated Aug. 11, 2011.
International Preliminary Report on Patentability in PCT application No. PCT/US2011/023427 dated Aug. 7, 2012.
International Preliminary Report on Patentability in PCT application No. PCT/US2011/062050 dated Mar. 6, 2014.
Office Action for JP Application No. 2012-523084 dated Aug. 1, 2014.
English Translation of Office Action for JP Application No. 2012-523084 dated Aug. 1, 2014.
Examination Report in Australian Application No. 2010278860 dated Aug. 14, 2014.
Vippagunta et al., "Crystalline solid," Advanced Drug Delivery, 2001, vol. 48 pp. 3-26.
Ulrich, "Crystallization," Chapter 4, Kirk-Othmer Encyclopedia of Chemical Technology, John Wiley and Sons 2002.
International Search Report and Written Opinion in International Application No. PCT/IB2017/000746, dated Sep. 18, 2017.

* cited by examiner

CRYSTALLIZATION METHOD AND BIOAVAILABILITY

CROSS-REFERENCE TO RELATED APPLICATIONS

This application claims priority under 35 USC § 119 to U.S. Application 62/343,509 filed May 31, 2016, which is incorporated herein by reference.

FIELD OF THE INVENTION

This disclosure pertains to improvement of the aqueous solubility and permeability of poorly permeable and sparingly water soluble drug compounds through generating novel crystalline forms of such drugs. The novel forms include but are not limited to cocrystals, salts, hydrates, solvates, solvates of salts, and mixtures thereof. Methods for the preparation and pharmaceutical compositions suitable for drug delivery systems that include one or more of these new forms are disclosed.

BACKGROUND OF THE INVENTION

Many Biopharmaceutic Classification System (BCS) class III or IV drugs suffer from the lack of gastrointestinal (GI) tract membrane permeability leading to poor oral bioavailability. Different strategies have been implemented to improve the permeability and subsequently the oral bioavailability of such drugs. For example, the U.S. patent application 20060068010 describes a formulation method for improving the permeability of drugs and subsequently increasing their bioavailability by granulation of the physical solid mixture of the drug with one or more amino acids, at least one inter-granular hydrophilic polymer, and an additional immediate release excipient. Another application WO 200602009 A1 disclosed the increase of the oral bioavailability for poorly permeable drugs such as bisphosphonates; risedronate as one of those drugs was mixed with a chelating agent such as ethylenediaminetetraacetate (EDTA) and other excipients to make an oral dosage form. Yet another application, WO 2007093226 A1, describes a method for improving the bioavailability of ibandronate by generating a physical mixture of the drug together with a modified amino acid (acylation or sulphonation of the amino group with phenyl or cyclohexyl) and other excipients. Another application WO 2003007916 A1 reports a gastric retention system to improve the bioavailability of a poorly permeable drug, alendronate, which was orally formulated with vitamin D and released an hour after the immediate release of vitamin D. WO 2006080780 discloses yet another method to improve the permeability and bioavailability of alendronate, a poorly permeable bisphosphonate, by mixing it with a biocompatible cationic polymer (i.e. water soluble chitosan) with up to a 10:1 weight ratio of the chitosan to the drug, while the resulting mixture can be formulated into a solid or liquid oral dosage form. A further method of improving permeability of drug materials was discussed in the U.S. patent application 2007/014319 A1, where an oral dosage form was formulated by a powder mixture of a bisphosphonic acid (e.g. zoledronic acid) together with an inactive ingredient (either an ester of a medium chain fatty acid or a lipophilic polyethylene glycol ester). A similar approach was disclosed in the US application 2007/0238707 A1 where a medium length fatty acid or its derivative (6-20 carbon atom fatty acid chain) was physically mixed with a poorly permeable drug (e.g. zoledronic acid) in a capsule that was enterically coated.

Zoledronic acid, known as (1-hydroxy-2-imidazol-1-yl-1-phosphono-ethyl)phosphonic acid, is depicted by the following chemical structure:

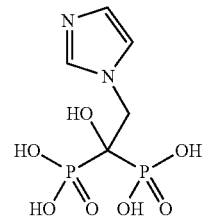

Zoledronic acid is a third generation bisphosphonate which far exceeds the previous generations in terms of efficacy and is used predominately for indications of osteoporosis, Paget's disease, hypercalcemia, and inhibition of bone metastasis. It was originally developed by Novartis and marketed as the monohydrate under the brand names Zometa® and Reclast®. Zoledronic acid was first approved in 2000 for the treatment of hypercalcemia in Canada. It was later approved for use in the US for hypercalcemia in 2001, for multiple myeloma and bone metastases from solid tumors in 2002, and for osteoporosis and Paget's disease in 2007. Clinical trials have also been conducted or are on-going exploring the use of zoledronic acid in neoadjuvant or adjuvant cancer therapy, Coleman, et al., British J Cancer 2010; 102(7): 1099-1105, Gnant, et al., New England J Medicine. 2009, 360 (17):679-691 and Davies, et al. J Clinical Oncology, 2010, 28(7s): Abstract 8021. Zoledronic acid is administered as an intravenous (IV) dose of 4 mg over 15 minutes for hypercalcemia of malignancy, multiple myeloma, and bone metastases from solid tumors, while an IV dose of 5 mg over 15 minutes is used for osteoporosis and Paget's disease.

Zoledronic acid is sparingly soluble in water and 0.1 N HCl solution but is freely soluble in 0.1 N NaOH. Zoledronic acid is practically insoluble in various organic solvents. Much effort has been taken to generate novel oral formulations of zoledronic acid through crystallization and metal salt formation to improve its aqueous solubility, permeability, and subsequent oral bioavailability. A crystalline trihydrate was disclosed in the U.S. Patent application 2006/0178439 A1 and world patent application WO2007/032808. Seven hydrated forms, an amorphous form, three monosodium salts, and eleven disodium salts with varying degrees of hydration of zoledronic acid were also disclosed in the patent application WO2005/005447 A2. Zoledronate metal salts including $Na^+$, $Mg^{2+}$, $Zn^{2+}$ were reported in the journal of Drugs of the Future (Sorbera et al, 25(3), *Drugs of the Future*, (2000)). Zoledronate, zoledronic, or zoledronic salt represents the ionic form of zoledronic acid. Patent application WO2008/064849 A1 from Novartis disclosed additional metal salts including two $Ca^{2+}$ salts, two $Zn^{2+}$ salts, one $Mg^{2+}$ salt, as well as a monohydrate, a trihydrate, an amorphous form, and an anhydrous form.

According to the US Food and Drug Administration (FDA) Summary Basis of Approval (SBA) for zoledronic acid, the poor oral bioavailability (approximately 1%), is partially due to its poor permeability in the GI tract. It was also noted that insoluble metal complexes were formed in the upper intestines, most commonly with calcium. Zoledronic acid has also been shown to cause severe gastric and intestinal irritations.

All of the above attempts to improve the oral bioavailability of zoledronic acid were either focused on improving the aqueous solubility by generating novel solid forms, or by mixing the drug with an inactive ingredient that has enhanced GI tract permeability. The improvement of aqueous solubility failed to improve the bioavailability of zoledronic acid, since the formation of insoluble zoledronate calcium complexes is unlikely to be prevented. On the other hand, powder mixtures of the poorly permeable drug with inactive permeability enhancers improved the bioavailability of the drug. This approach of mixing different materials with different particle sizes and size distributions could result in poor blend/physical mixture uniformity. Constituents of the mixture could also segregate during transportation or with shaking and vibration. Additionally, the powder blends require rigorous batch-to-batch consistency to ensure the uniformity of the blend batches.

The present invention relates, in part, to a deliberate molecular design to create a molecular complex of a drug and additional component(s) (coformer(s)) in a single crystalline structure. The benefit of such design can lead to the elimination of all the batch to batch blend uniformity and particle segregation problems that powder blends often suffer from. In addition, this invention simplifies the manufacturing of the solid dosage form (comprised of drug and excipient) such that the final solid dosage form is, in one embodiment, a powder of the molecular complex.

Additionally, the resulting molecular complexes possess very different physicochemical properties compared to the parent drug, coformer or their physical mixture. These properties include but are not limited to melting point, thermal and electrical conductivity, aqueous solubility, rate of dissolution and permeability across the GI tract membrane. The permeability improvement could result in the enhancement of the oral bioavailability of the BCS class III and IV drugs. This concept of a molecular complex by design was employed to improve the permeability and subsequent bioavailability of a poorly permeable drug such as zoledronic acid. The mechanisms behind the permeability enhancement, however, are not fully understood.

The upward trend in the use of oral drugs continues especially in light of the goal to decrease the overall cost of healthcare. Orally administered drugs are becoming more preferred in various therapeutic areas including cancers. Clearly, there is an opportunity to create oral dosage forms of IV drugs where oral dosage forms do not yet exist due to their poor aqueous solubility and/or poor permeability providing a clear clinical benefit for patients. Given the fact that zoledronic acid is only approved for IV administration, there is a need to develop an oral dosage form of zoledronic acid. By using pharmaceutically acceptable and/or approved coformers to hydrogen bond with zoledronic acid, novel molecular complexes (e.g. cocrystals, salts, solvates, and mixtures thereof) with improve solubility and/or permeability can be created. These novel molecular complexes could be used in the development of an oral dosage form of zoledronic acid for the treatment of osteoporosis, Paget's disease, hypercalcemia, inhibition of bone metastasis and Psoriatic Arthritis.

SUMMARY OF THE INVENTION

The present disclosure is directed, in part, towards generating new forms of zoledronic acid, which have the therapeutic efficacy of zoledronic acid discussed above, with improved aqueous solubility, rate of dissolution, and/or improved permeability and thus enhanced bioavailability. One aspect of the present disclosure includes novel molecular complexes of zoledronic acid that includes cocrystals, salts, and solvates (e.g. hydrates and mixed solvates as well as solvates of salts), and mixtures containing such materials. In addition, the disclosure further includes methods for the preparation of such complexes.

The disclosure further includes compositions of molecular complexes of zoledronic acid suitable for incorporation in a pharmaceutical dosage form. Specific molecular complexes pertaining to the disclosure include, but are not limited to, complexes of zoledronic acid with sodium, ammonium, ammonia, L-lysine, DL-lysine, nicotinamide, adenine, and glycine. Obvious variants of the disclosed zoledronic acid forms in the disclosure, including those described by the drawings and examples, will be readily apparent to the person of ordinary skill in the art having the present disclosure and such variants are considered to be a part of the current invention.

The invention further includes compositions comprising molecular complexes of zoledronic acid and excess coformer, preferably, L-lysine, DL-lysine, or glycine. The invention further includes compositions comprising physical mixes of zoledronic acid and a coformer, preferably, L-lysine, DL-lysine, or glycine.

The disclosure also includes results of an in vivo study of parent (pure) zoledronic acid and selected zoledronic acid complexes prepared by the methods of the invention in rat and dog models. The drug concentrations in the rat plasma and dog serum samples along with the pharmacokinetic (PK) profiles are also included.

The disclosure also includes method of treatment of disease that could be caused by the immune system attacking body joints such as Psoriatic Arthritis using pharmaceutical formulations of the novel zoledronic acid generated by this invention. The foregoing and other features and advantages of the disclosed technology will become more apparent from the following detailed description, which proceeds with reference to the accompanying drawings. Such description is meant to be illustrative, but not limiting, of the invention.

DETAILED DESCRIPTION OF THE PREFERRED EMBODIMENTS

Figure 1:
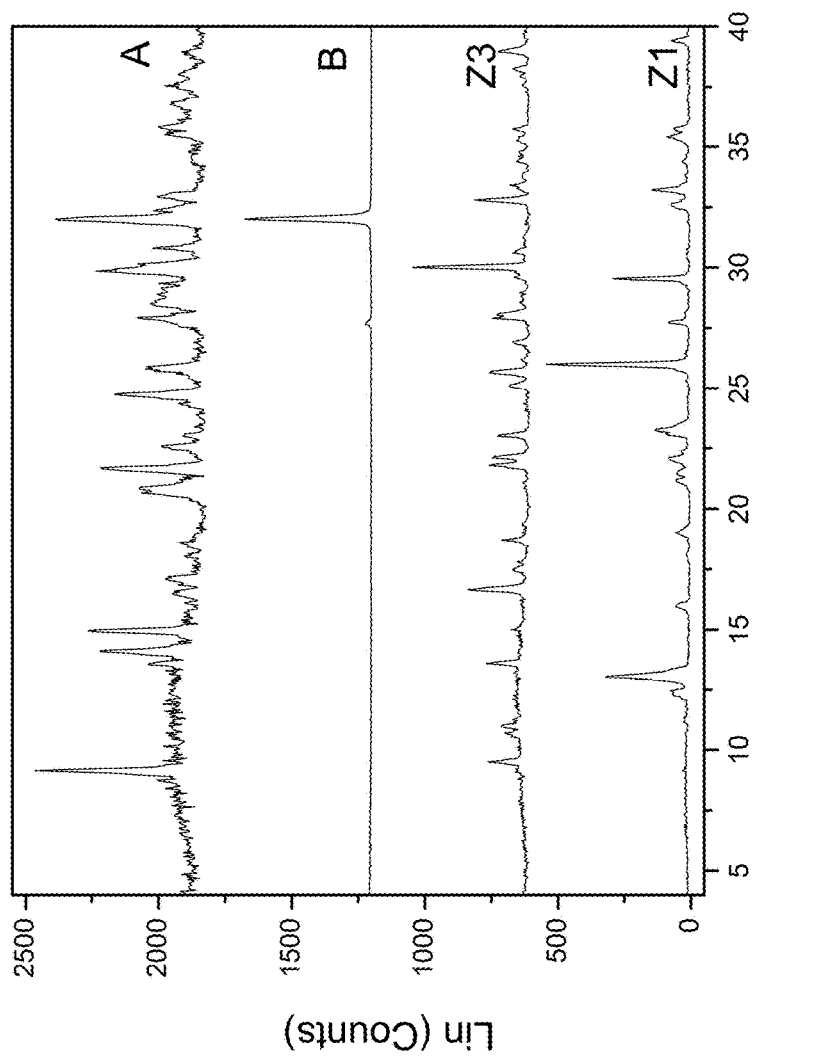
FIG. 1 shows PXRD diffractograms of: (A=zoledronic acid, sodium zoledronic salt and water complex), (B=NaCl), (Z1=Zoledronic acid monohydrate), (Z3=Zoledronic acid trihydrate).

In general, active pharmaceutical ingredients (APIs) in the pharmaceutical compositions can be prepared in a variety of different forms including prodrugs, amorphous forms, solvates, hydrates, cocrystals, salts and polymorphs. The discovery of novel API forms may provide an opportunity to improve the performance characteristics of a pharmaceutical product.

Additionally, discovery of drug forms expands the array of resources available for designing pharmaceutical dosage forms with targeted release profiles or other desired characteristics.

A specific characteristic that can be targeted includes the crystal form of an API. The alteration of the crystal form of a given API would result in the modification of the physical properties of the target molecule. For example, various polymorphs of a given API exhibit different aqueous solubility, while the thermodynamically stable polymorph would exhibit a lower solubility than the meta-stable polymorph. In addition, pharmaceutical polymorphs can also differ in properties such as rate of dissolution, shelf life, bioavailability, morphology, vapor pressure, density, color, and compressibility. Accordingly, it is desirable to enhance the properties of an API by forming molecular complexes such as a cocrystal, a salt, a solvate or hydrate with respect to aqueous solubility, rate of dissolution, bioavailability, Cmax, Tmax, physicochemical stability, down-stream processibility (e.g. flowability compressibility, degree of brittleness, particle size manipulation), decrease in polymorphic form diversity, toxicity, taste, production costs, and manufacturing methods.

In the development of orally delivered drugs, it is often advantageous to have novel crystal forms of such drugs that possess improved properties, including increased aqueous solubility and stability. In many cases, the dissolution rate increase of drugs is desired as it would potentially increase their bioavailability. This also applies to the development of novel forms of zoledronic acid which, when administered orally to a subject could achieve a greater or similar bioavailability and PK profile when compared to an IV or other formulations on a dose-for-dose basis.

Cocrystals, salts, solvates and hydrates of zoledronic acid of the present invention could give rise to improved properties of zoledronic acid. For example, a new form of zoledronic acid is particularly advantageous if it can improve the bioavailability of orally delivered zoledronic acid. A number of novel zoledronic acid forms have been synthesized, characterized, and disclosed herein. Of particular interest are the zoledronic acid and the standard amino acids since they have indicated enhanced permeability compared with other molecular complexes of zoledronic acid. The mechanism of enhanced permeability of these complexes is not yet understood and, while not to be bound by this explanation, it is possible that they moderate the formation of the insoluble Ca' zoledronate salt resulting in more zoledronic acid to be absorbed paracellularly through the tight junctions. It must be stressed that this is a possible mechanism of enhanced permeability.

Schematic diagrams for zoledronic acid:amino acid complexes (a zoledronic acid:lysine complex and a zoledronic acid:glycine complex, two embodiments of the invention) are shown below. The diagrams show a molecular structure of the complex and possible interactions between the constituents of the complex which is different from the physical mix of the constituents.

Zoledronic Acid: Lysine Complex

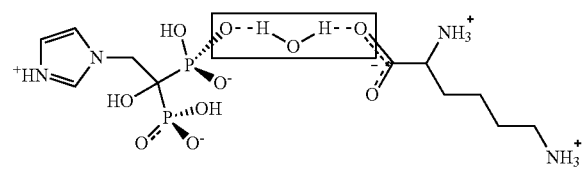

Zoledronic Acid: Glycine Complex

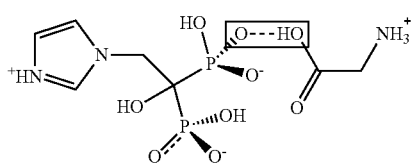

These represent one of the arrangements that molecules of the drug and the standard amino acids coformers could interact to form a stable complex that even when stressed thermally at elevated relative humidity (RH) environment have not displayed any signs of deterioration or disintegration to its original constituents. Such stability can be attributed to the hydrogen bonding (dashed line in the box) in these molecular complexes. When packing in a crystal structure these complexes have very different morphologies to that of its constituents or their physical mix as indicated by their powder X-ray diffraction (PXRD) patterns and therefore would possess different, unpredictable physicochemical properties.

The present invention provides a new crystal form of zoledronic acid in the form of zoledronic acid, sodium zoledronate and water complex, characterized by an X-ray powder diffraction pattern having strong peaks at about 8.1, 13.3, 21.5, 24.6, and 25.6±0.2 degrees two-theta.

The present invention provides a new crystal form of zoledronic acid in the form of ammonium zoledronic salt and water complex, characterized by an X-ray powder diffraction pattern having strong peaks at about 11.0, 14.6, 15.4, 19.9, and 29.4±0.2 degrees two-theta.

The present invention provides a new crystal form of zoledronic acid in the form of zoledronic, L-lysine, and water complex, characterized by an X-ray powder diffraction pattern having strong peaks at about 9.0, 14.4, 18.1, 26.0, and 29.6±0.2 degrees two-theta.

The present invention provides a new crystal form of zoledronic acid in the form of zoledronic, DL-lysine, and water complex, characterized by an X-ray powder diffraction pattern having strong peaks at about 9.1, 14.7, 18.0, 21.2, and 26.0±0.2 degrees two-theta.

The present invention provides a new crystal form of zoledronic acid in the form of zoledronic acid, zoledronic, DL-lysine, ethanol, and water complex, characterized by an X-ray powder diffraction pattern having strong peaks at about 8.8, 9.7, 17.6, 23.1, and 26.5±0.2 degrees two-theta.

The present invention provides a new crystal form of zoledronic acid in the form of zoledronic acid, nicotinamide, and water complex, characterized by an X-ray powder diffraction pattern having strong peaks at about 13.1, 15.2, 21.0, 23.9, and 26.5±0.2 degrees two-theta.

The present invention provides a new crystal form of zoledronic acid in the form of zoledronic, adenine, and water complex, characterized by an X-ray powder diffraction pattern having strong peaks at about 13.6, 15.9, 19.7, 27.9, and 29.5±0.2 degrees two-theta.

The present invention provides a new crystal form of zoledronic acid in the form of zoledronic and glycine complex, characterized by an X-ray powder diffraction pattern having strong peaks at about 10.2, 17.8, 19.9, 22.9, and 28.1±0.2 degrees two-theta.

The present invention provides a new crystal form of zoledronic acid in the form of zoledronic diammonia water complex, characterized by an X-ray powder diffraction pattern having strong peaks at about 12.2, 13.0, 14.1, 17.1, and 19.3±0.2 degrees two-theta.

The present invention provides a new crystal form of zoledronic acid in the form of zoledronic, DL-lysine, and water complex, characterized by an X-ray powder diffraction pattern having strong peaks at about 8.3, 11.8, 12.3, 15.8, and 20.8±0.2 degrees two-theta.

The present invention provides a new crystal form of zoledronic acid in the form of zoledronic acid, L-lysine, and water complex, characterized by an X-ray powder diffraction pattern having strong peaks at about 9.6, 10.7, 14.3, 21.4, 23.5±0.2 degrees two-theta.

The present invention provides a new crystal form of zoledronic acid in the form of zoledronic, DL-lysine, and water complex, characterized by an X-ray powder diffraction pattern having strong peaks at about 9.7, 10.8, 14.4, 18.9, 21.4±0.2 degrees two-theta.

The present invention provides rat plasma or dog serum concentration levels and PK profiles of IV, orally and ID delivered zoledronic acid parent compound versus complexes of zoledronic acid created using the method of this invention.

Accordingly, in a first aspect, the present invention includes complexes of zoledronic acid with sodium, ammonium, ammonia, L-lysine, DL-lysine, nicotinamide, adenine and glycine which are capable of complexing in the solid-state, for example, through dry or solvent-drop grinding (liquid assisted grinding), heating or solvent evaporation of their solution in single or mixed solvent systems, slurry suspension, supercritical fluids or other techniques known to a person skilled in the art.

Another aspect of the invention provides zoledronic and nicotinamide complex by dissolving both compounds in water:ethylacetate (1:1 v/v) and allowing the solvent mixtures to evaporate to form crystalline material.

Another aspect of the invention provides zoledronic and glycine solid complex from dissolving both compounds in water, and allowing the solvent to evaporate to form crystalline material.

Another aspect of the invention provides complexes of zoledronic acid and sodium, ammonium, ammonia, L-lysine, DL-lysine, nicotinamide, adenine and glycine suitable for a pharmaceutical formulation than can be delivered orally to the human body. The pharmaceutical formulation contains a therapeutically effective amount of at least one of the novel molecular complexes of zoledronic acid according to the invention and at least one pharmaceutically acceptable carrier, (also known in the art as a pharmaceutically acceptable excipient). The novel molecular complexes of zoledronic acid are therapeutically useful for the treatment and/or prevention of disease states associated with osteoporosis, hypercalcemia (TIH), cancer induced bone metastasis, Paget's disease or adjuvant or neoadjuvant therapies, discussed above. Psoriatic Arthritis (PsA) is another indication that can benefit from using the novel molecular complexes or its active ingredient for treatment thereof. Psoriatic Arthritis is a joint inflammation thought to be caused by the immune system attacking body joints. If left untreated it could lead to joint damage and subsequent dysfunction.

The invention also relates to methods of treatment of several disease conditions including PsA using novel molecular complexes of zoledronic acid of the invention or a pharmaceutical formulation containing them. A pharmaceutical formulation of the invention may be in any pharmaceutical form which contains a novel molecular complex of zoledronic acid according to the invention. The pharmaceutical formulation may be, for example, a tablet, capsule, liquid suspension, injectable, suppository, topical, or transdermal. The pharmaceutical formulations generally contain about 1% to about 99% by weight of at least one novel molecular complex of zoledronic acid of the invention and 99% to 1% by weight of a suitable pharmaceutical excipient.

Complexes of zoledronic acid and sodium, ammonium, ammonia, L-lysine, DL-lysine, nicotinamide, adenine, and glycine have been observed by their PXRD patterns and FTIR spectra.

Another aspect of the invention provides in vivo data in rats concerning the oral bioavailability of zoledronic acid delivered orally and intraduodenally.

Another aspect of the invention provides PK profiles of the parent compound delivered by different routes; IV, oral and ID.

Another aspect of the invention provides modified oral bioavailability values of novel zoledronic acid complexes prepared by the method of invention, compared with the orally delivered parent compound.

Another aspect of the invention provides the addition of excess cocrystal formers to the zoledronic acid complexes.

Another aspect of the invention provides a method where the excess cocrystal formers consist of standard amino acids.

Another aspect of the invention provides modified PK profiles of zoledronic acid complexes with excess cocrystal formers, compared with that of the orally delivered parent compound.

Another aspect of the invention provides improved aqueous solubility of novel zoledronic acid complexes compared with the parent compound.

Another aspect of the invention provides modified oral bioavailability values of novel zoledronic acid complexes with excess cocrystal formers, compared with the orally delivered parent compound.

Another aspect of the invention provides in vivo data in dogs concerning the oral bioavailability of zoledronic acid delivered IV or orally.

Another aspect of the invention provides modified oral bioavailability values in dogs of novel zoledronic acid complexes prepared by the method of invention delivered in gelatin capsules compared with the orally delivered parent compound.

Another aspect of the invention provides modified oral bioavailability values in dogs of novel zoledronic acid complexes prepared by the method of invention delivered in enteric coated gel capsules compared with that of the parent compound.

Another aspect of the invention provides substantial improvement in oral bioavailability values in dogs of novel zoledronic acid complexes with excess cocrystal formers prepared by the method of invention delivered in hard gelatin capsules.

Another aspect of the invention provides substantial improvement in oral bioavailability values in dogs of novel zoledronic acid complex (zoledronic, DL-lysine and water) with excess cocrystal former (DL-lysine) prepared by the method of the invention delivered in hard gelatin capsules.

Another aspect of the invention provides substantial improvement in oral bioavailability values in dogs of micronized novel zoledronic acid complex (zoledronic, DL-lysine and water) with excess micronized cocrystal former (DL-lysine) prepared by the method of the invention delivered in hard gelatin capsules.

Another aspect of the invention provides micronized novel zoledronic acid complex (zoledronic, DL-lysine and water) where the particle mean size diameter is 5 micron by volume.

Another aspect of the invention provides micronized excess cocrystal former (DL-lysine) where the particle mean size diameter is 5 micron by volume.

Another aspect of the invention provides slight improvement in oral bioavailability values for zoledronic acid in dogs via zoledronic acid and novel zoledronic acid complexes orally delivered through enteric coated capsules.

Another aspect of the invention provides a reduced oral bioavailability values for zoledronic acid in dogs via novel zoledronic acid complexes with excess physical mix of coformer.

Another aspect of the invention provides a molecular complex comprising a bisphosphonic acid or salt thereof and at least one coformer, wherein the bioavailability of the bisphosphonic acid or salt thereof from the molecular complex is greater than the bioavailability of the bisphosphonic acid or salt thereof without the coformer. The bisphosphonic acid may be, for example, zoledronic acid, clodronic acid, tiludronic acid, pamidronic acid, alendronic acid, risedronic acid ibandronic acid or other bisphosphonic acids known in the art.

Another aspect of the invention provides a method for enhancing the bioavailabilty or permeability of a bisphosphonic acid comprising the step of administering to a patient in need thereof a therapeutically effective amount of a bisphosphonic acid in the form of a molecular complex.

The techniques and approaches set forth in the present disclosure can further be used by the person of ordinary skill in the art to prepare variants thereof, said variants are considered to be part of the inventive disclosure.

EXAMPLES

The following examples illustrate the invention without intending to limit the scope of the invention.

Zoledronic acid as a starting material used in all experiments in this disclosure was supplied by Farmkemi Limited (Wuhan Pharma Chemical Co.), China with purity of ca. 98% and was purified further via recrystallization from water. All other pure chemicals (Analytical Grade) were supplied by Sigma-Aldrich and used without further purification.

Enteric coating of gelatin capsules was contracted out to AzoPharma, Hollywood, Fla., USA. A 10% w/w coating solution of Eudragit L100-55, and triethyl citrate, 9.09 and 0.91 w/w % respectively, in purified water and acetone was used in the Vector LDCS pan coater to achieve a uniform coating layer on the capsules. The coating uniformity and functionality for duodenal delivery was tested by 2 hr dissolution in simulated gastric fluid stirred at 75 rpm and 37° C. All capsules remained closed for the duration of this test.

Samples Micronization was carried out at the Jet Pulverizer Company (NJ, USA) using a three inch diameter mill.

Solid Phase Characterization

Analytical techniques used to observe the crystalline forms include powder X-ray diffraction (PXRD) and Fourier transform infrared spectroscopy (FTIR). The particular methodology used in such analytical techniques should be viewed as illustrative, and not limiting in the context of data collection. For example, the particular instrumentation used to collect data may vary; routine operator error or calibration standards may vary; sample preparation method may vary (for example, the use of the KBr disk or Nujol mull technique for FTIR analysis).

Fourier Transform FTIR Spectroscopy (FTIR): FTIR analysis was performed on a Perkin Elmer Spectrum 100 FTIR spectrometer equipped with a solid-state ATR accessory. Powder X-Ray Diffraction (PXRD): All zoledronic acid molecular complex products were observed by a D-8 Bruker X-ray Powder Diffractometer using Cu Kα (λ=1.540562 Å), 40 kV, 40 mA. The data were collected over an angular range of 3° to 40° 2θ in continuous scan mode at room temperature using a step size of 0.05° 2θ and a scan speed of 6.17°/min. Laser scattering particle size analysis: All micronized samples were tested using the Horiba LA950 laser scattering particle size analyzer, dry method using air at pressure of 0.3 MPA to fluidize the micronized samples before flowing in the path of a laser beam. The micronized samples were further tested using light microscopy to verify the Horiba results.

Figure 2:
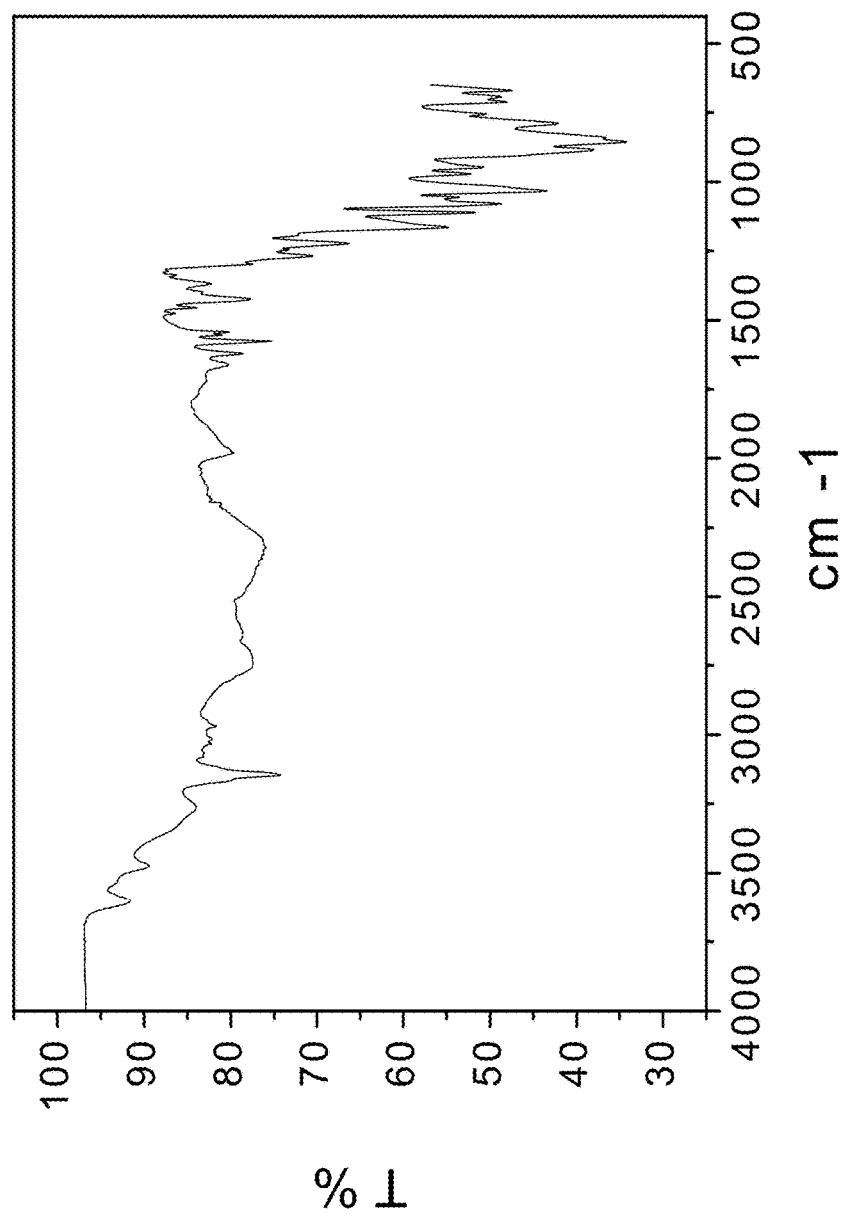
FIG. 2 is an FTIR spectrum of a complex comprising zoledronic acid, sodium zoledronic salt, and water.

Example 1: Preparation of Zoledronic Acid, Sodium Zoledronic Salt, and Water Complex 200 mg of zoledronic acid was slurried with 180 mg of sodium chloride in 1 mL of 1:1 ethanol:water overnight. The material was filtered and rinsed. The particulate material was gathered and stored in a screw cap vial for subsequent analysis. The material was characterized by PXRD and FTIR corresponding to FIG. 1 and FIG. 2, respectively.

Figure 3:
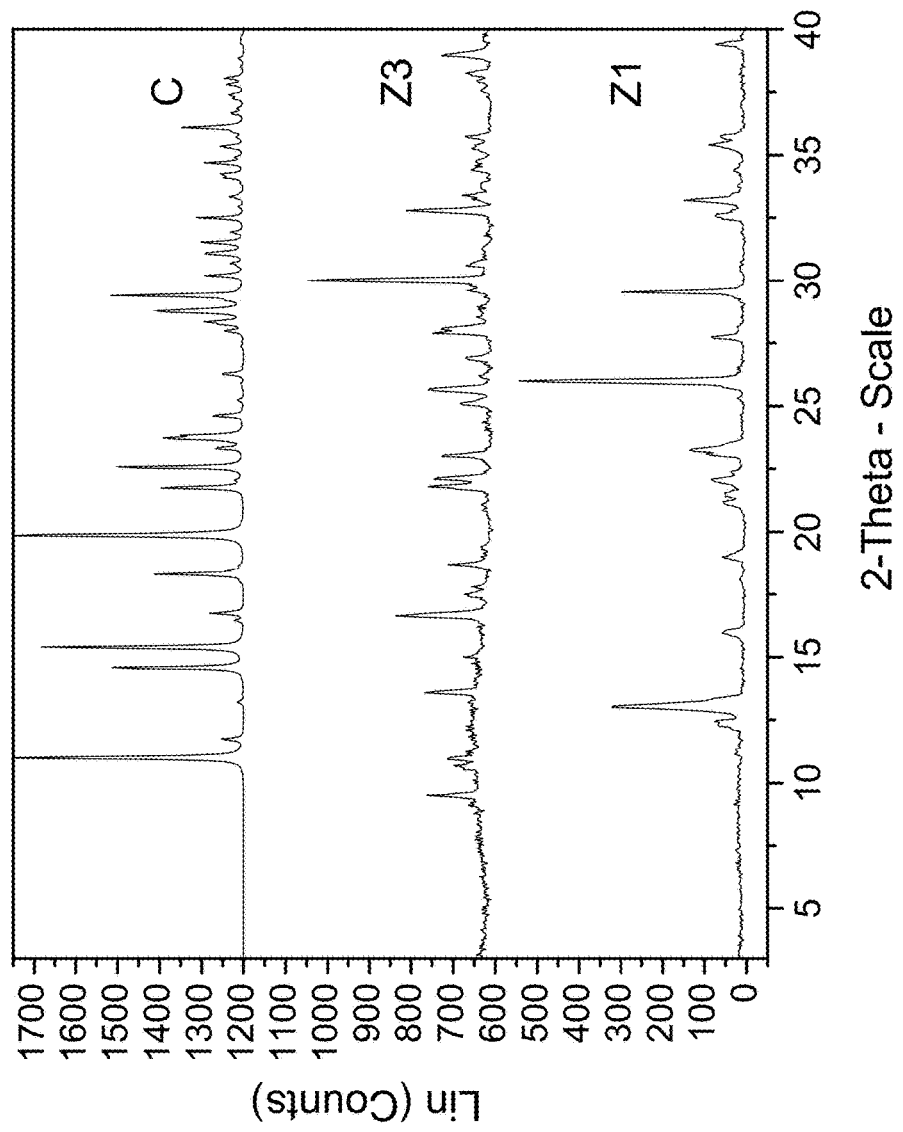
FIG. 3 shows PXRD diffractograms of: (C=ammonium zoledronic salt and water complex), (Z1=Zoledronic acid monohydrate), and (Z3=Zoledronic acid trihydrate).
Figure 4:
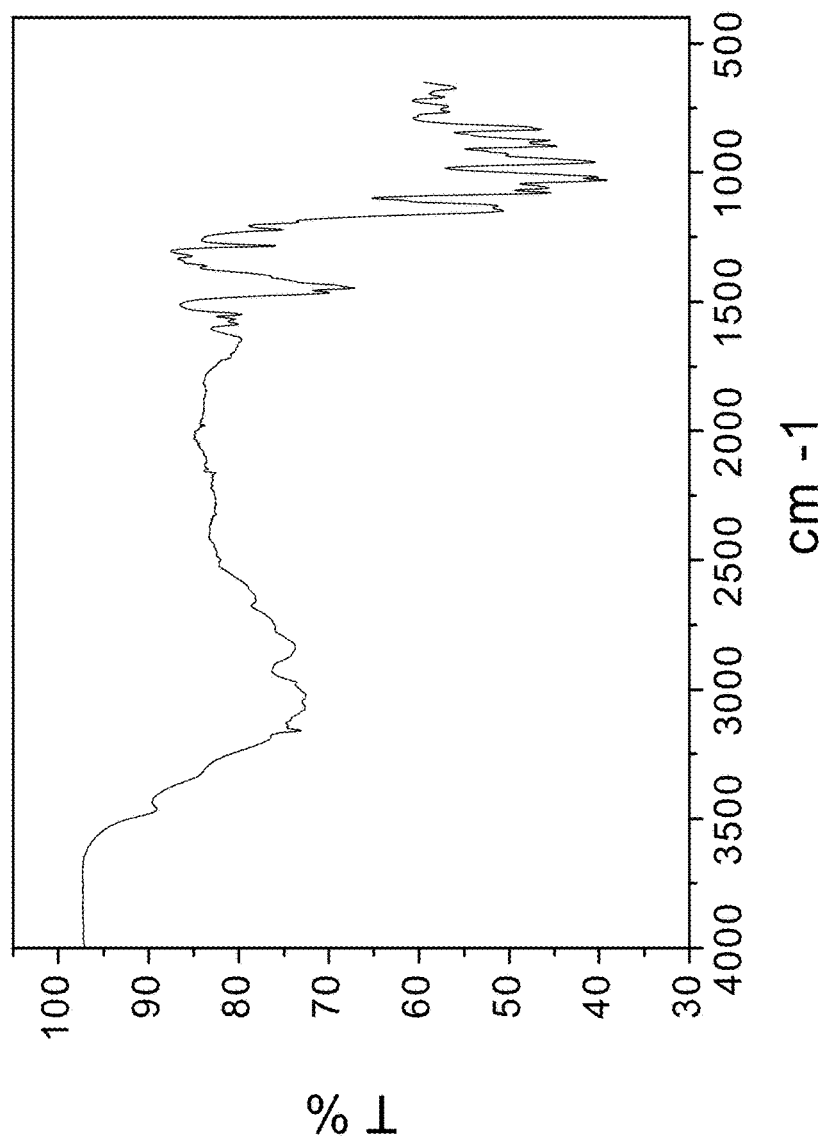
FIG. 4 is an FTIR spectrum of ammonium zoledronic salt and water complex.

Example 2: Preparation of Ammonium Zoledronic Salt and Water Complex 300 mg of zoledronic acid was slurried in 7N ammonia in methanol overnight. The material was filtered and rinsed. The particulate material was dissolved in water and left to evaporate at ambient conditions to obtain colorless plates after 1 week. The material was characterized by PXRD and FTIR corresponding to FIG. 3 and FIG. 4, respectively.

Figure 5:
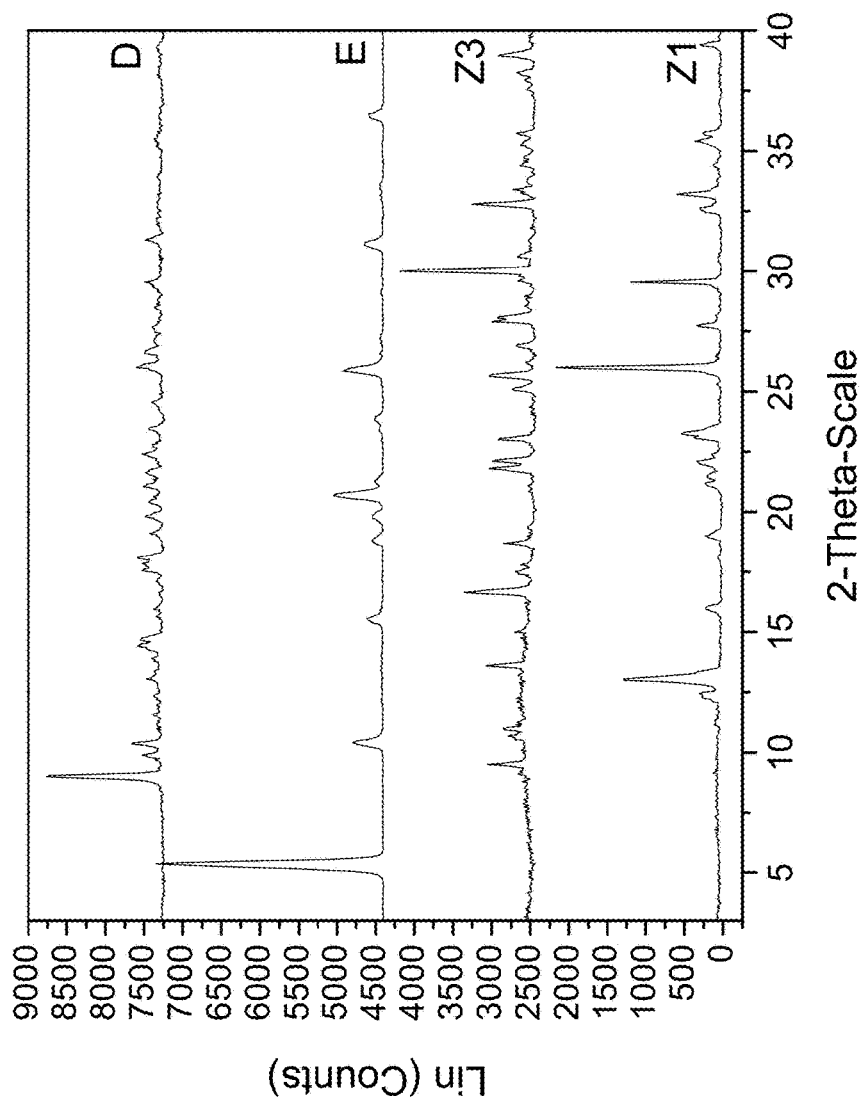
FIG. 5 shows PXRD diffractograms of: (D=zoledronic, L-lysine, and water complex), (E=L-lysine), (Z1=Zoledronic acid monohydrate), and (Z3=Zoledronic acid trihydrate).
Figure 6:
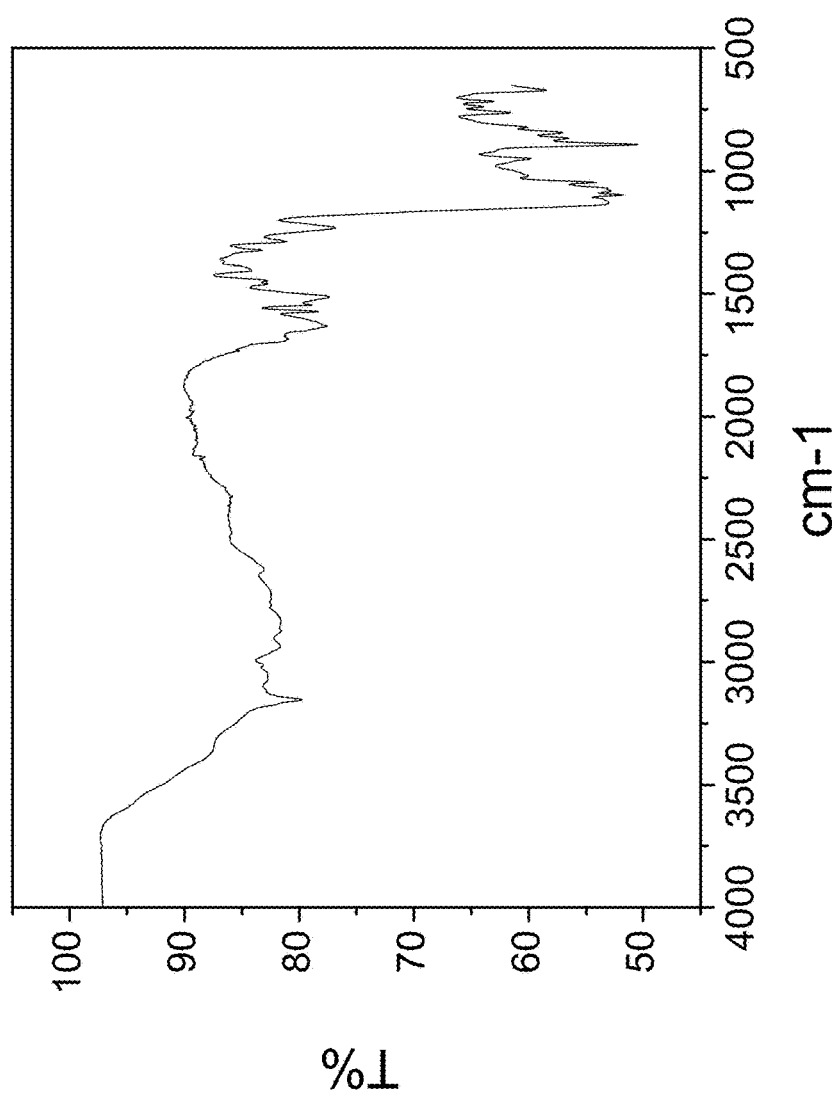
FIG. 6 is an FTIR spectrum of zoledronic, L-lysine, and water complex.

Example 3: Preparation of Zoledronic, L-Lysine, and Water Complex 200 mg of zoledronic acid and 54 mg of L-lysine were slurried in 2 mL of tetrahydrofuran and 200 μl of water overnight. The solids gathered after filtration were dried and stored in a screw cap vials for subsequent analysis. The material was characterized by PXRD and FTIR corresponding to FIG. 5 and FIG. 6, respectively.

Figure 7:
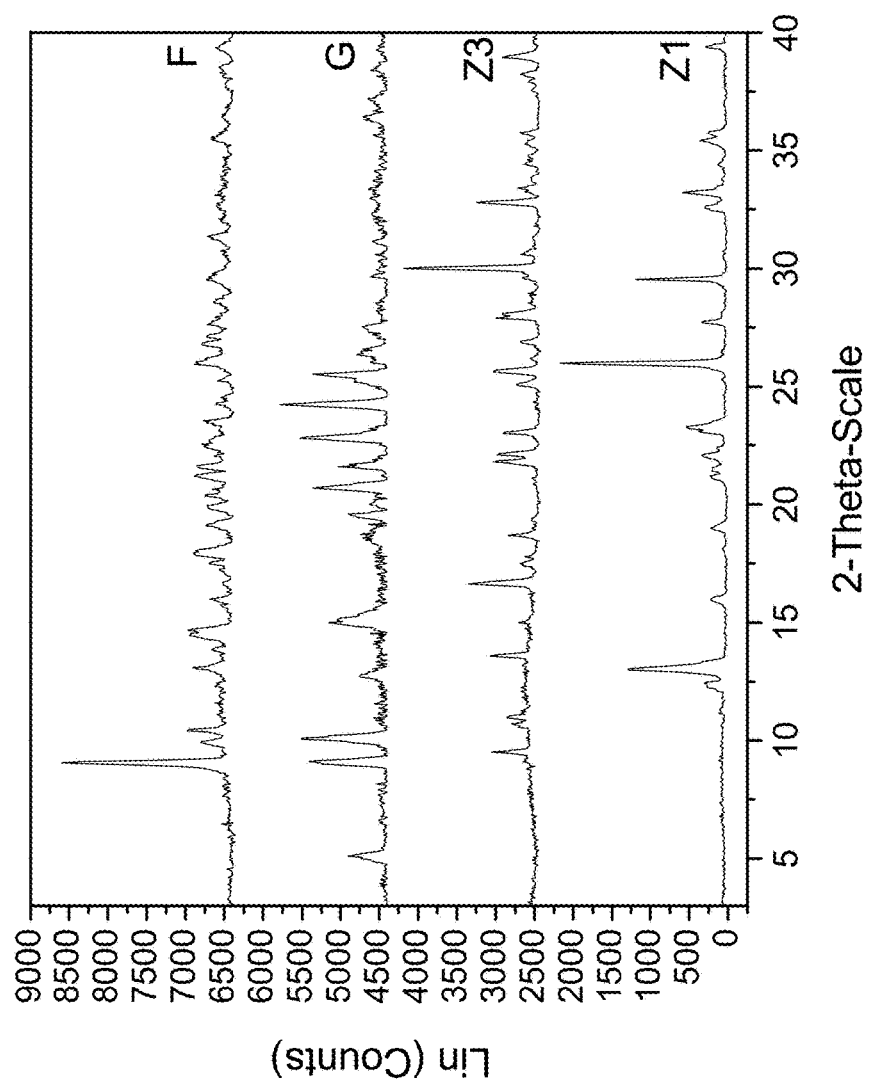
FIG. 7 shows PXRD diffractograms of: (F=zoledronic, DL-lysine, and water complex), (G=DL-lysine), (Z1=Zoledronic acid monohydrate), and (Z3=Zoledronic acid trihydrate).
Figure 8:
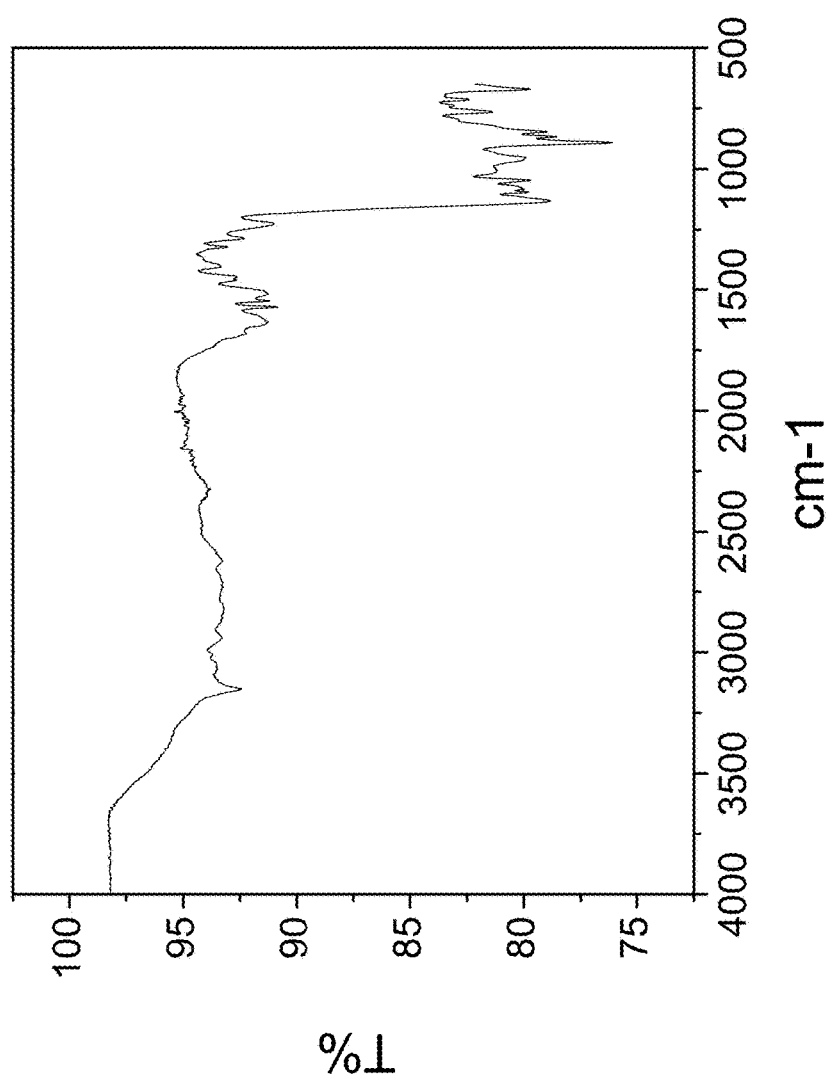
FIG. 8 is an FTIR spectrum of zoledronic, DL-lysine, and water complex.

Example 4: Preparation of Zoledronic, DL-Lysine, and Water Complex 204 mg of zoledronic acid and 59 mg of DL-lysine were slurried in 2 mL of tetrahydrofuran and 200 μl of water overnight. The solids gathered after filtration were dried and stored in a screw cap vials for subsequent analysis. The material was characterized by PXRD and FTIR corresponding to FIG. 7 and FIG. 8 respectively.

Figure 9:
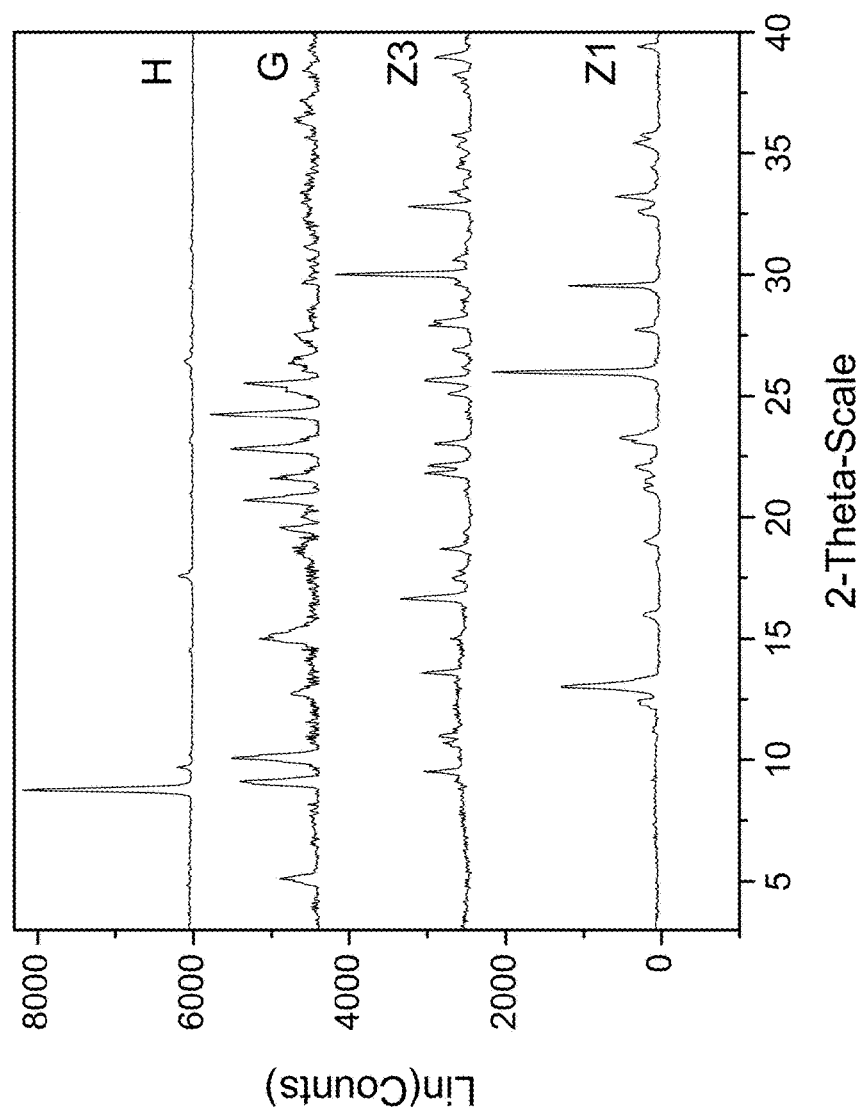
FIG. 9 shows PXRD diffractograms of: (H=zoledronic acid, zoledronic, DL-lysine, ethanol, and water complex), (G=DL-lysine), (Z1=Zoledronic acid monohydrate), (Z3=Zoledronic acid trihydrate).
Figure 10:
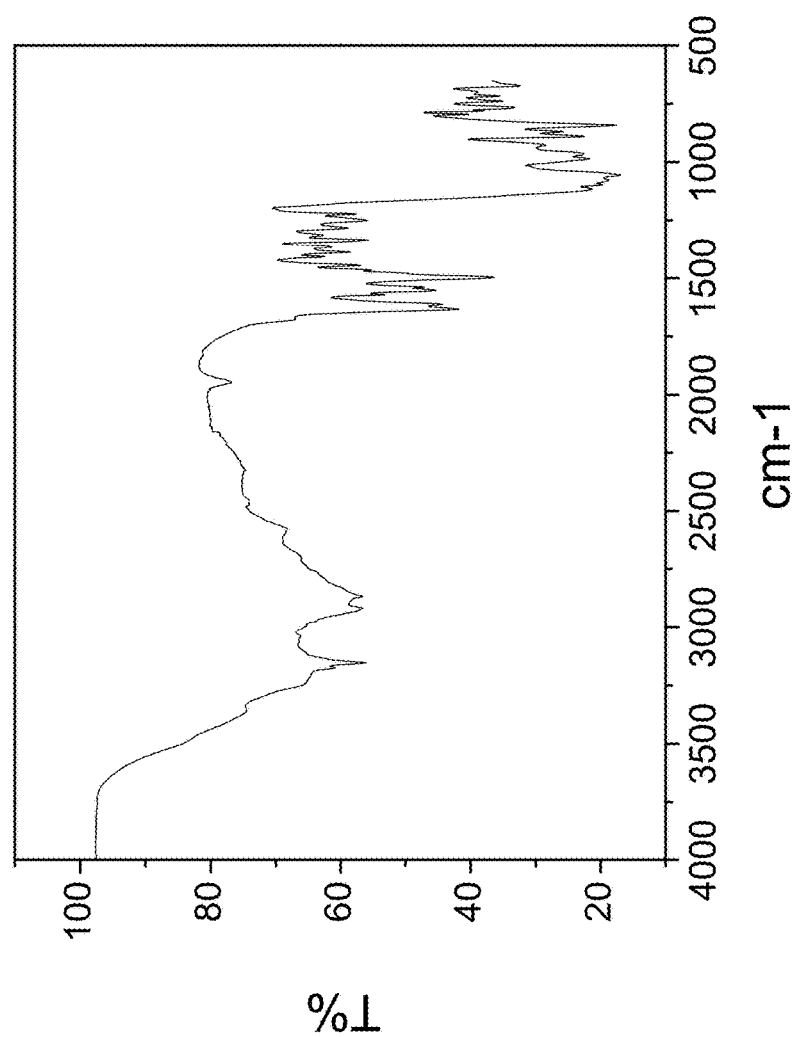
FIG. 10 is an FTIR spectrum of zoledronic acid, zoledronic, DL-lysine, ethanol, and water complex.

Example 5: Preparation of Zoledronic Acid, Zoledronic, DL-Lysine, Ethanol, and Water Complex 103 mg of zoledronic acid and 54 mg of DL-lysine were dissolved in 400 μl of water, capped and stirred overnight. The next day 0.25 mL of ethanol was added drop wise. The vial was capped with a screw cap vial and after 1 day crystals appeared and were filtered off. The material was stored for subsequent analysis. The material was characterized by PXRD and FTIR corresponding to FIG. 9 and FIG. 10 respectively.

Figure 11:
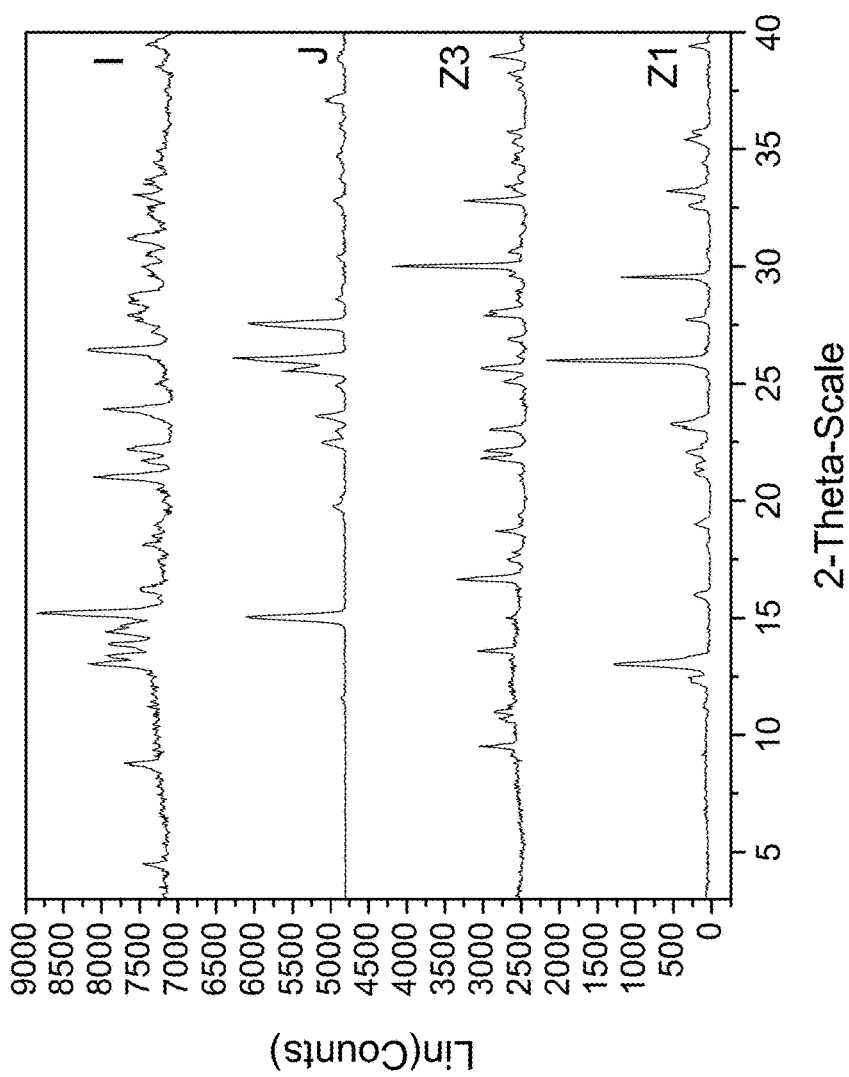
FIG. 11 shows PXRD diffractograms of: (I=zoledronic, nicotinamide, and water complex), (J=nicotinamide), (Z1=Zoledronic acid monohydrate), and (Z3=Zoledronic acid trihydrate).
Figure 12:
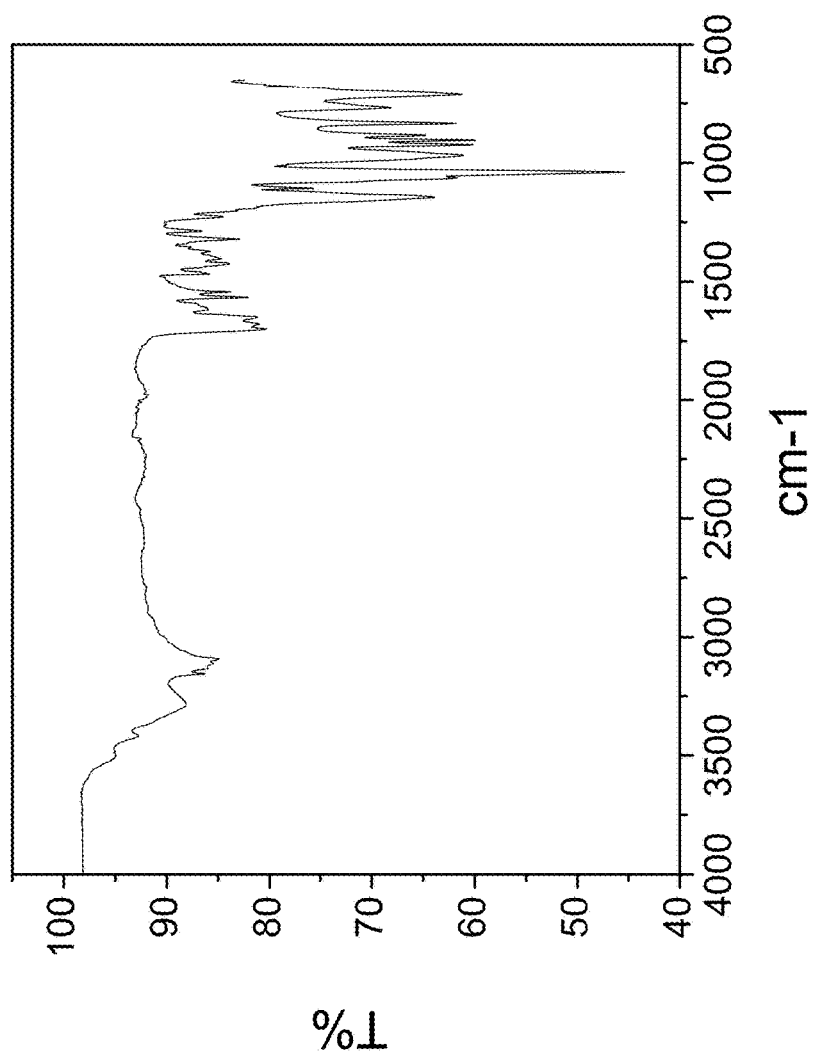
FIG. 12 is an FTIR spectrum of zoledronic, nicotinamide, and water complex.

Example 6: Preparation of Zoledronic, Nicotinamide, and Water Complex by Solvent-Drop Grinding 99 mg of zoledronic acid was ground with 44 mg of nicotinamide and 40 μl of water was added to the solid mixture. The solids gathered after grinding were stored in screw cap vials for subsequent analysis. The material was characterized by PXRD and FTIR corresponding to FIG. 11 and FIG. 12, respectively.

Example 7: Preparation of Zoledronic, Nicotinamide, and Water Complex from Solution Crystallization 25 mg of zoledronic acid and 138 mg of nicotinamide were dissolved in 2 mL of a water:ethylacetate mix (1:1 v/v). The solution was then allowed to stand for several hours to effect the slow evaporation of solvent. The solids gathered were characterized and produced very similar PXRD and FTIR patterns to that of Example 7 product.

Example 8: Preparation of Zoledronic, Adenine, and Water Complex by Solvent-Drop Grinding 96 mg of zoledronic acid was ground with 65 mg of adenine and 60 μL of water was added to the solid mixture.

Figure 13:
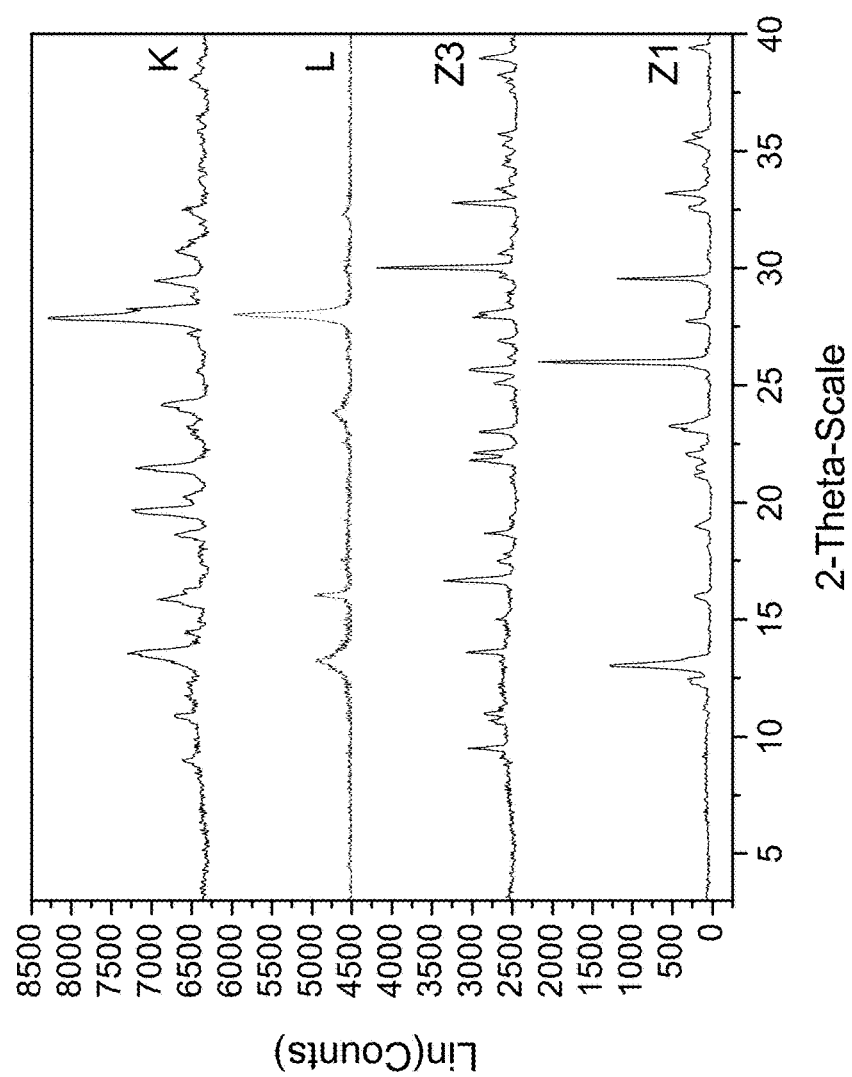
FIG. 13 shows PXRD diffractograms of: (K=zoledronic, adenine, and water complex), (L=adenine), (Z1=Zoledronic acid monohydrate), (Z3=Zoledronic acid trihydrate).
Figure 14:
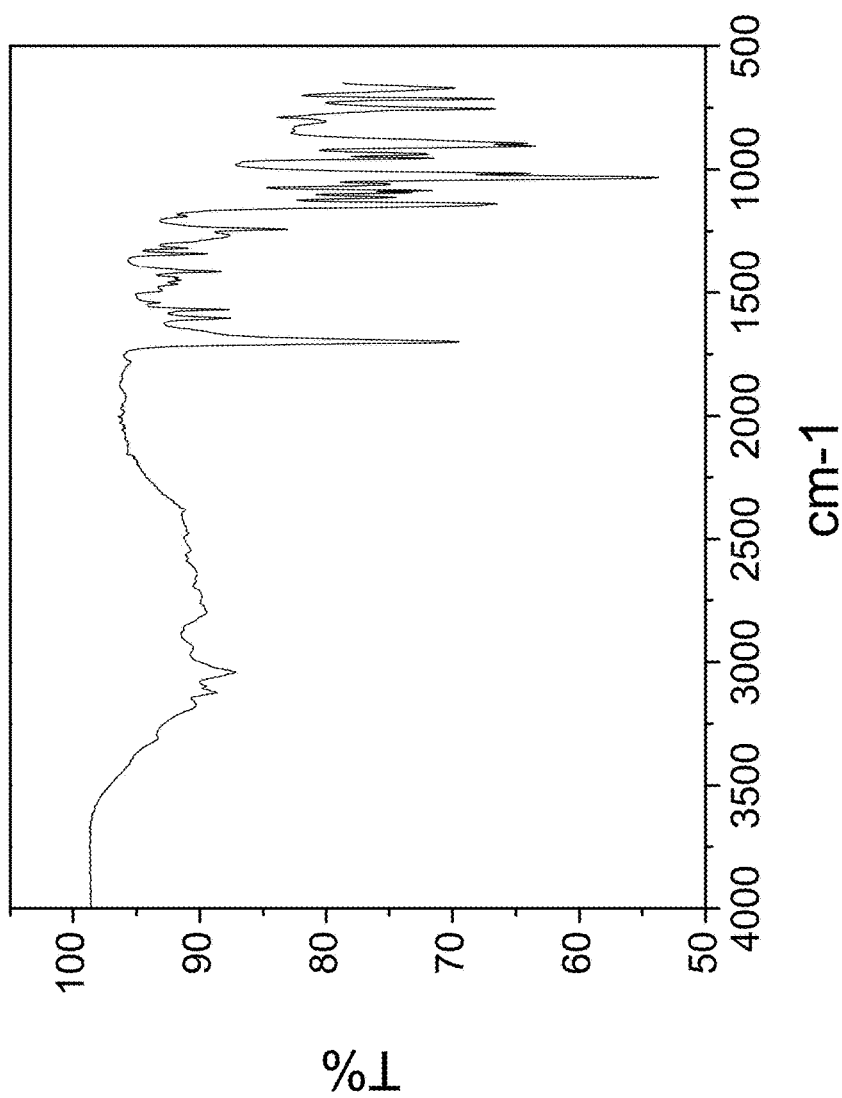
FIG. 14 is an FTIR spectrum of zoledronic, adenine, and water complex.

The solids gathered after grinding were stored in screw cap vials for subsequent analysis. The material was characterized by PXRD and FTIR corresponding to FIG. 13 and FIG. 14, respectively.

Example 9: Preparation of Zoledronic, Adenine, and Water Complex from Solution Slurry 99 mg of zoledronic acid and 54 mg of adenine were slurried in 2 mL of a water:ethanol mix (1:1 v/v) overnight. The solids gathered after filtration were dried, characterized and produced very similar PXRD and FTIR patterns to that of Example 8 product.

Figure 15:
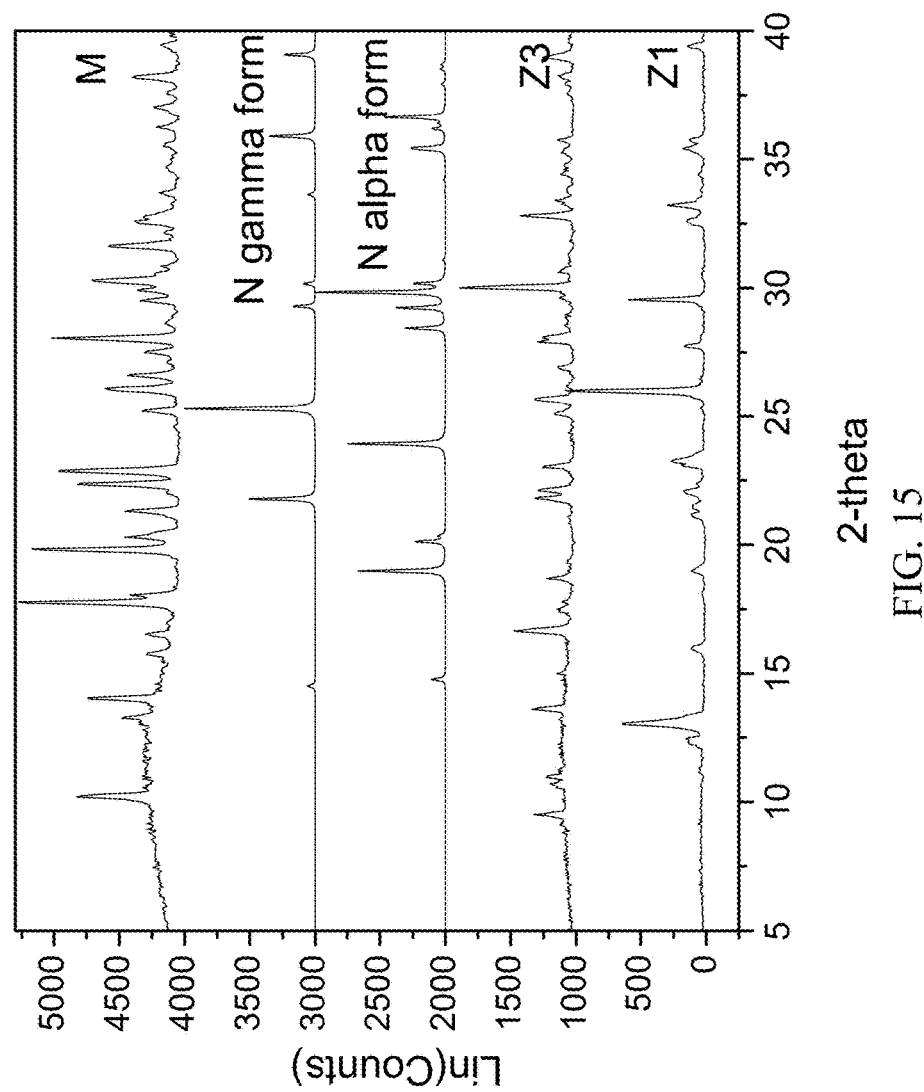
FIG. 15 shows PXRD diffractograms of: (M=zoledronic and glycine complex), (N=glycine), (Z1=Zoledronic acid monohydrate), and (Z3=Zoledronic acid trihydrate).
Figure 16:
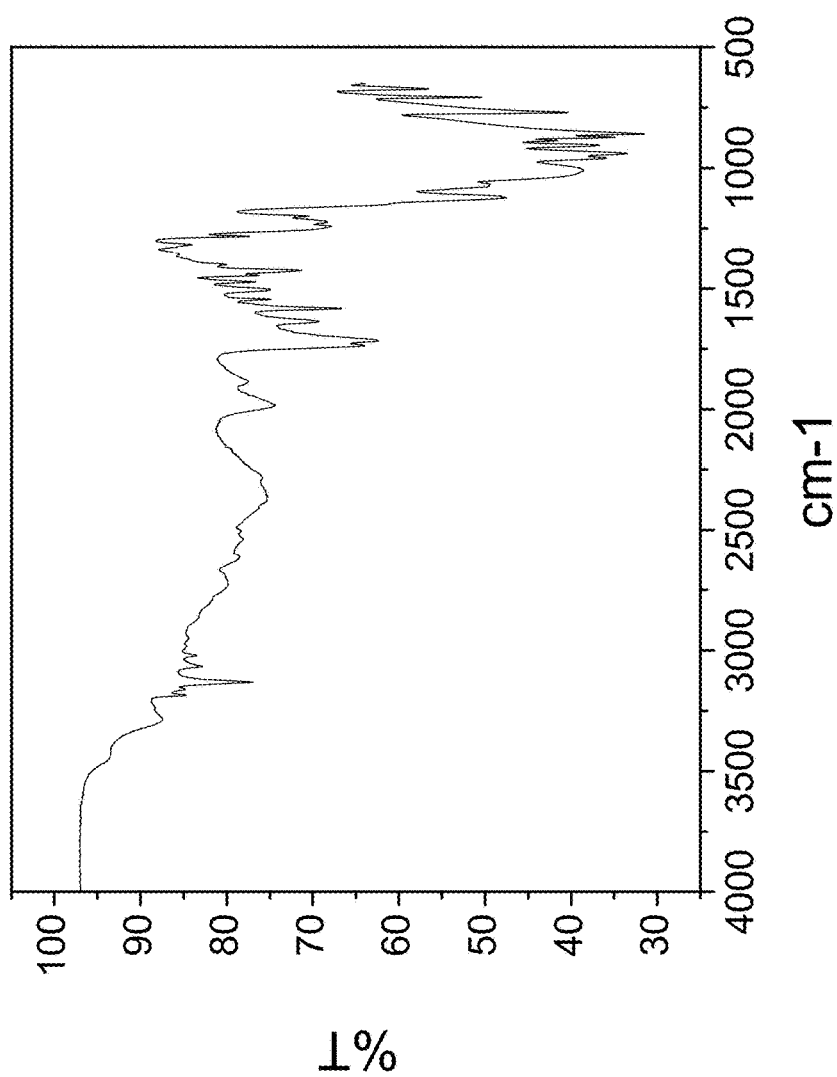
FIG. 16 is an FTIR spectrum of zoledronic and glycine complex.

Example 10: Preparation of Zoledronic and Glycine Complex 178 mg of zoledronic acid and 45 mg of glycine were slurried in 2 mL of water overnight. The solids gathered after filtration were dried and stored in a screw cap vials for subsequent analysis. The material was characterized by PXRD and FTIR corresponding to FIG. 15 and FIG. 16, respectively.

Figure 17:
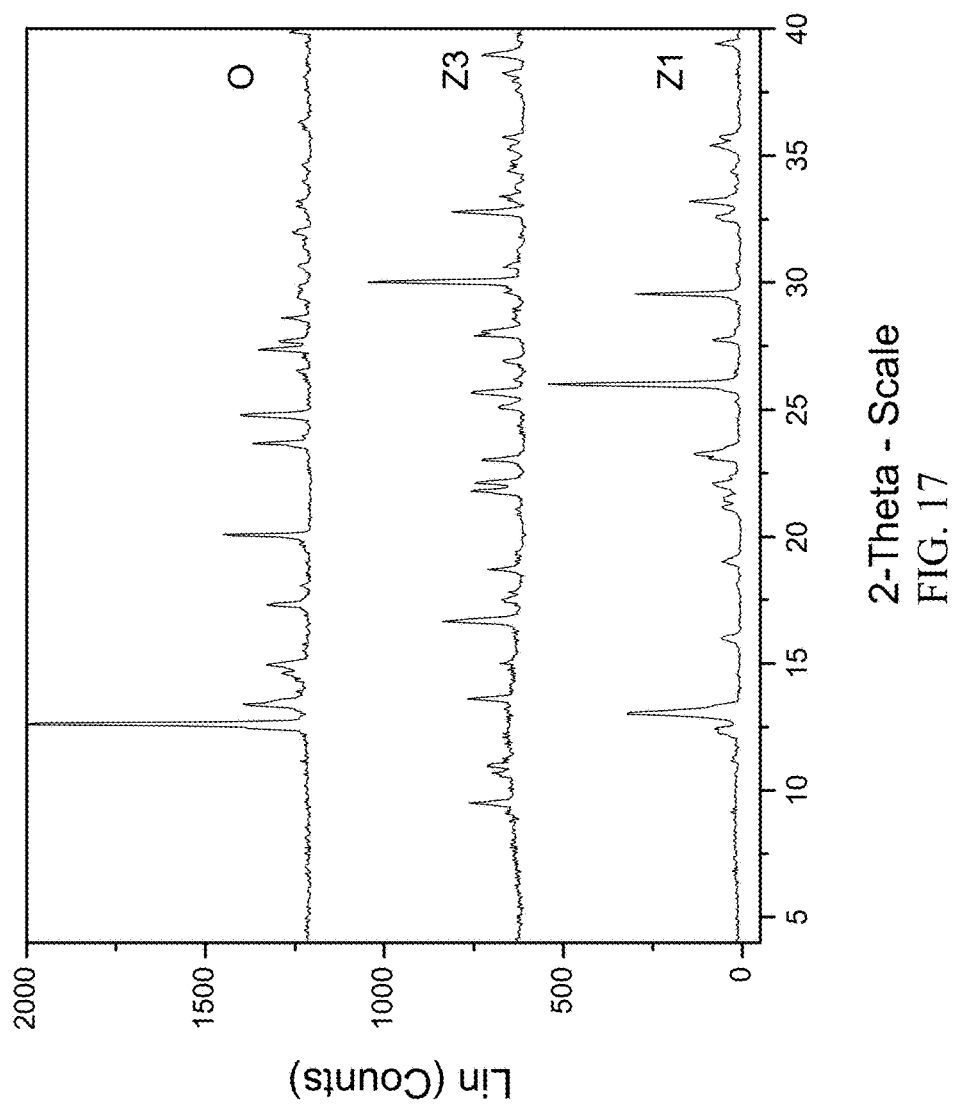
FIG. 17 shows PXRD diffractograms of: (O=zoledronic diammonia water complex), (Z1=Zoledronic acid monohydrate), and (Z3=Zoledronic acid trihydrate).
Figure 18:
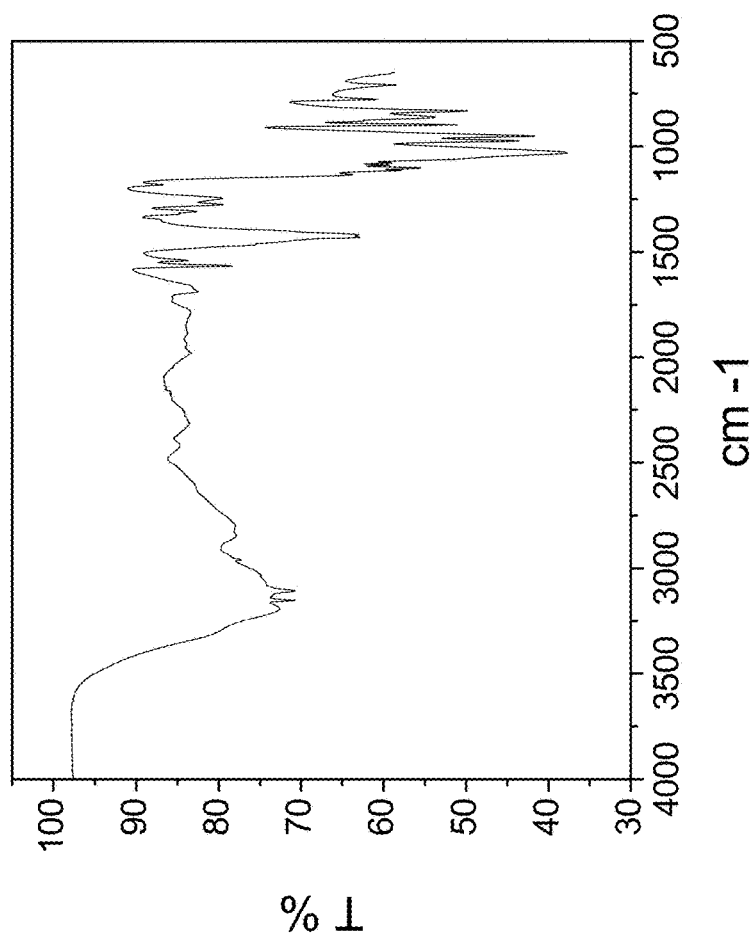
FIG. 18 is an FTIR spectrum of zoledronic diammonia water complex.

Example 11: Preparation of Zoledronic Diammonia Water Complex 1.5 g of zoledronic acid was slurried in 7N ammonia in methanol overnight. The material was filtered and rinsed. The particulate material was dissolved in water with medium heat and left to evaporate at ambient conditions to obtain colorless blocks after 1 day. The material was characterized by PXRD and FTIR corresponding to FIG. 17 and FIG. 18, respectively.

Figure 19:
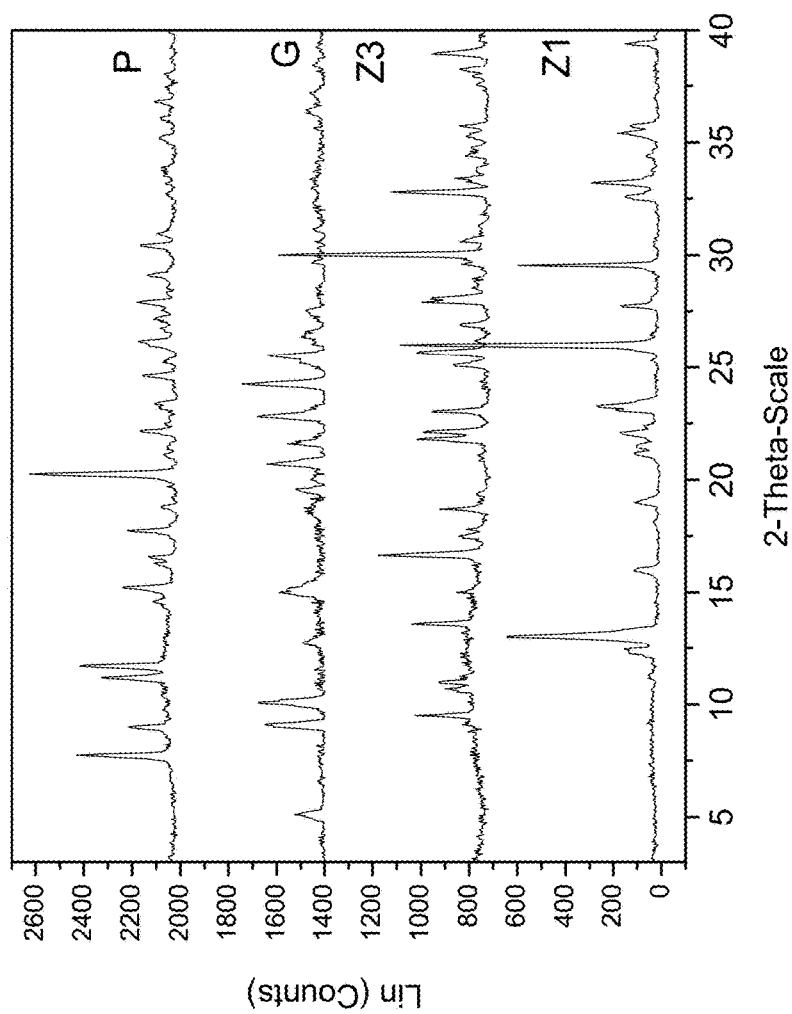
FIG. 19 shows PXRD diffractograms of: (P=zoledronic, DL-lysine, and water complex), (G=DL-lysine), (Z1=Zoledronic acid monohydrate), and (Z3=Zoledronic acid trihydrate).
Figure 20:
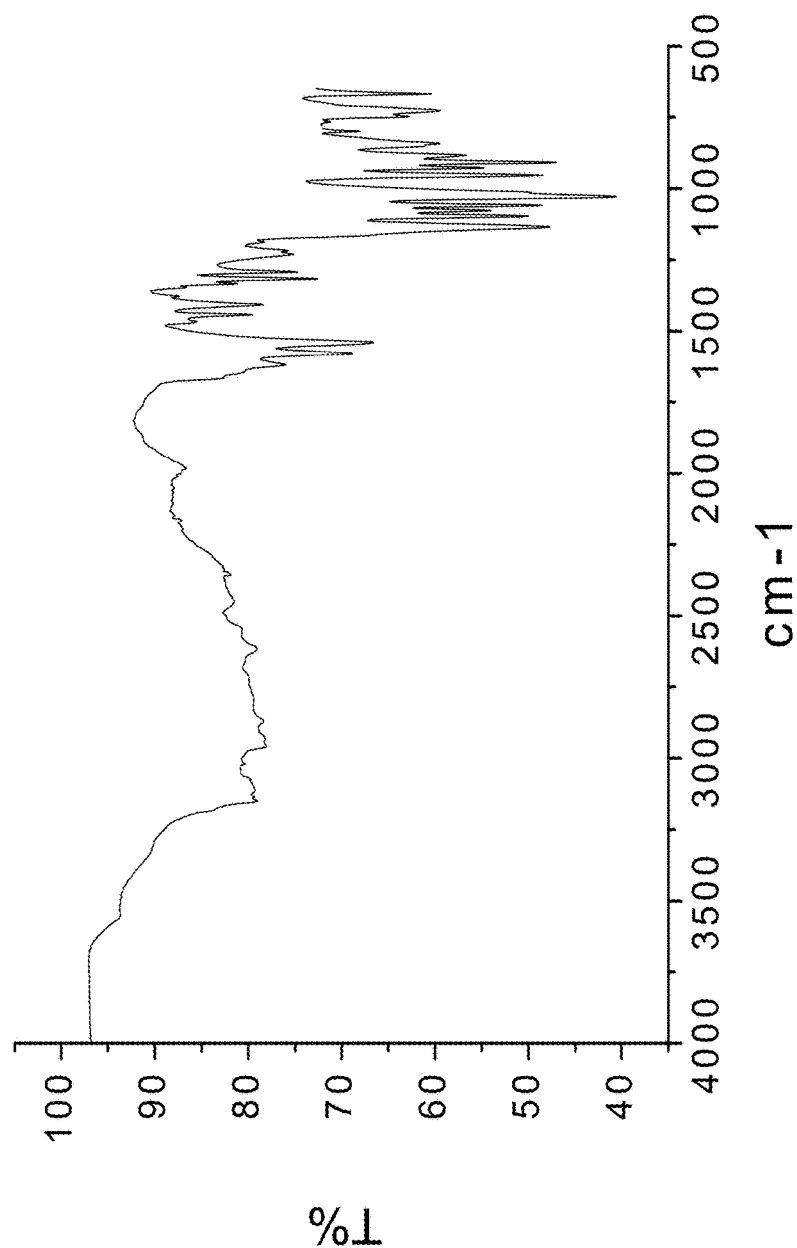
FIG. 20 is an FTIR spectrum of zoledronic, DL-lysine, and water complex.

Example 12: Preparation of Zoledronic, DL-Lysine, and Water Complex 200 mg of zoledronic acid and 102 mg of DL-lysine were slurried in 2 mL of tetrahydrofuran and 400 µl of water overnight. The solids gathered after filtration were dried and stored in a screw cap vials for subsequent analysis. The material was characterized by PXRD and FTIR corresponding to FIG. 19 and FIG. 20 respectively.

Figure 21:
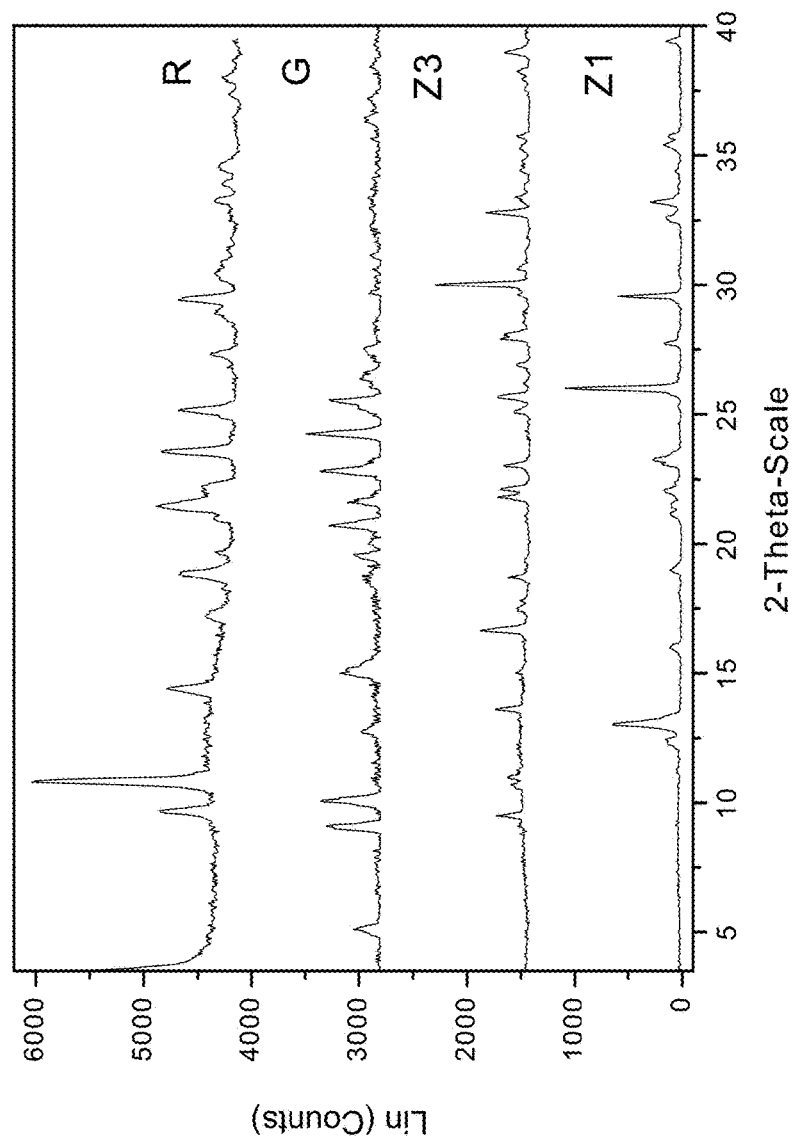
FIG. 21 shows PXRD diffractograms of: (R=zoledronic, DL-lysine, and water complex), (G=DL-lysine), (Z1=Zoledronic acid monohydrate), and (Z3=Zoledronic acid trihydrate).
Figure 22:
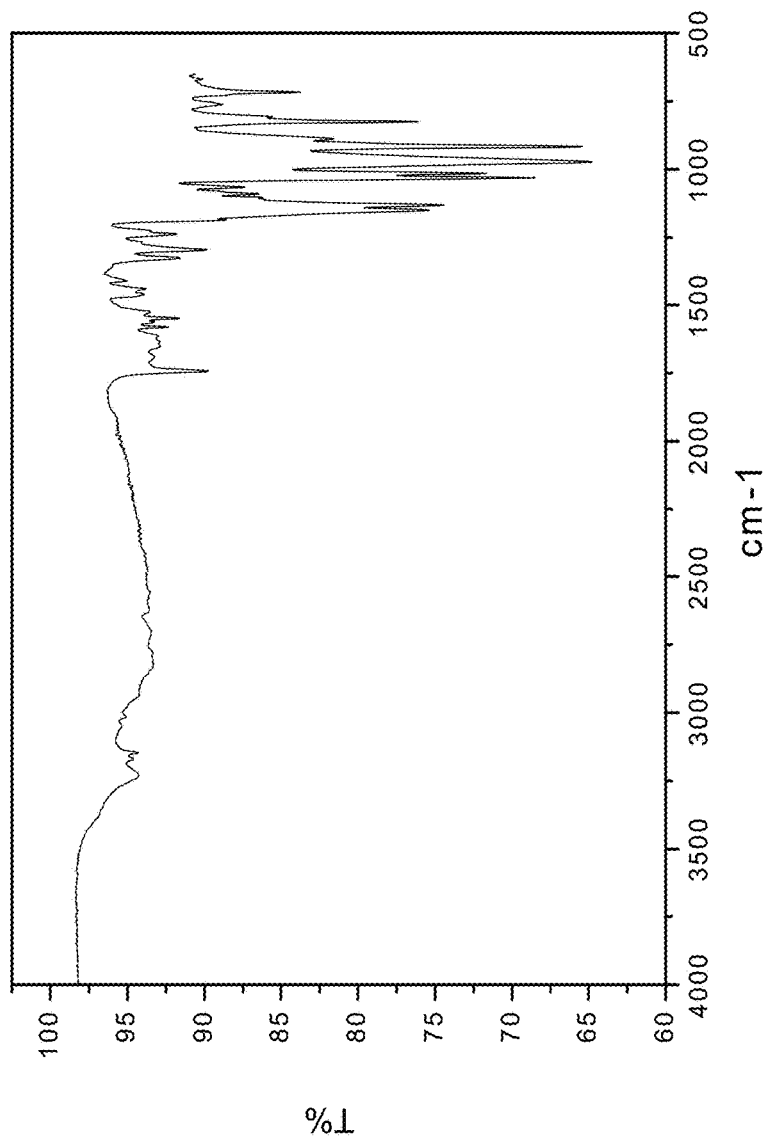
FIG. 22 is an FTIR spectrum of zoledronic, DL-lysine, and water complex.

Example 13: Preparation of Zoledronic, DL-Lysine, and Water Complex 1 g of zoledronic acid and 283 mg of DL-lysine were slurried in 80 mL of tetrahydrofuran and 8 mL of water overnight. The solids gathered after filtration were dried and stored in a screw cap vials for subsequent analysis. The material was characterized by PXRD and FTIR corresponding to FIG. 21 and FIG. 22 respectively.

Figure 23:
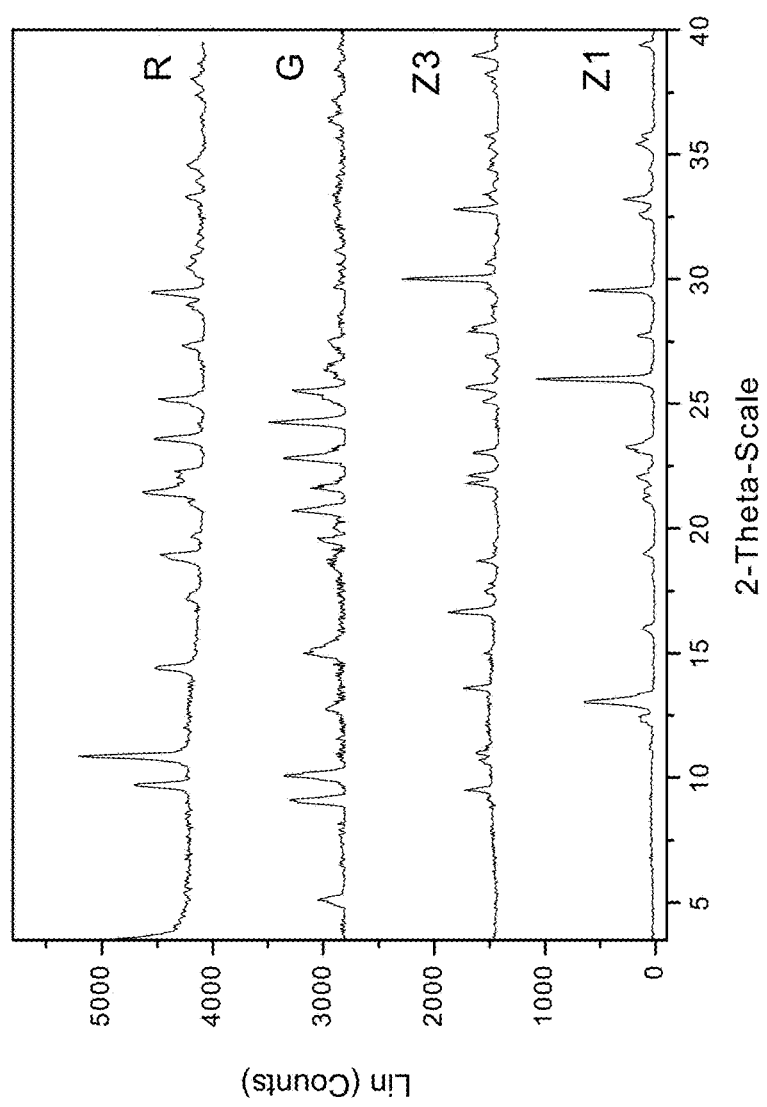
FIG. 23 shows PXRD diffractograms of: (R=zoledronic, DL-lysine, and water complex), (G=DL-lysine), (Z1=Zoledronic acid monohydrate), and (Z3=Zoledronic acid trihydrate).
Figure 24:
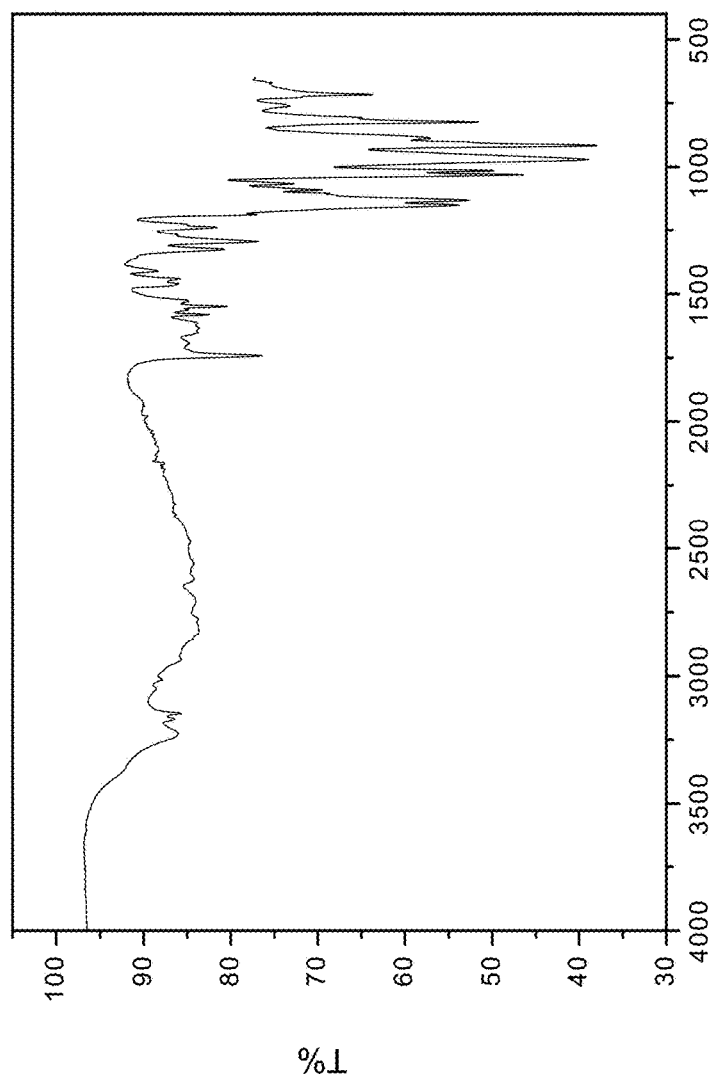
FIG. 24 is an FTIR spectrum of zoledronic, DL-lysine, and water complex.

Example 14: Preparation of Zoledronic, DL-Lysine, and Water Complex by Antisolvent Method This complex can also be prepared by the antisolvent method by dissolving 1 g of zoledronic acid and 283 mg of DL-lysine in 5 mL of hot water and adding 40 mL of ethanol as an antisolvent stirred overnight. Similar PXRD and FTIR profiles were obtained as shown in FIGS. 23 and 24 respectively.

Figure 25:
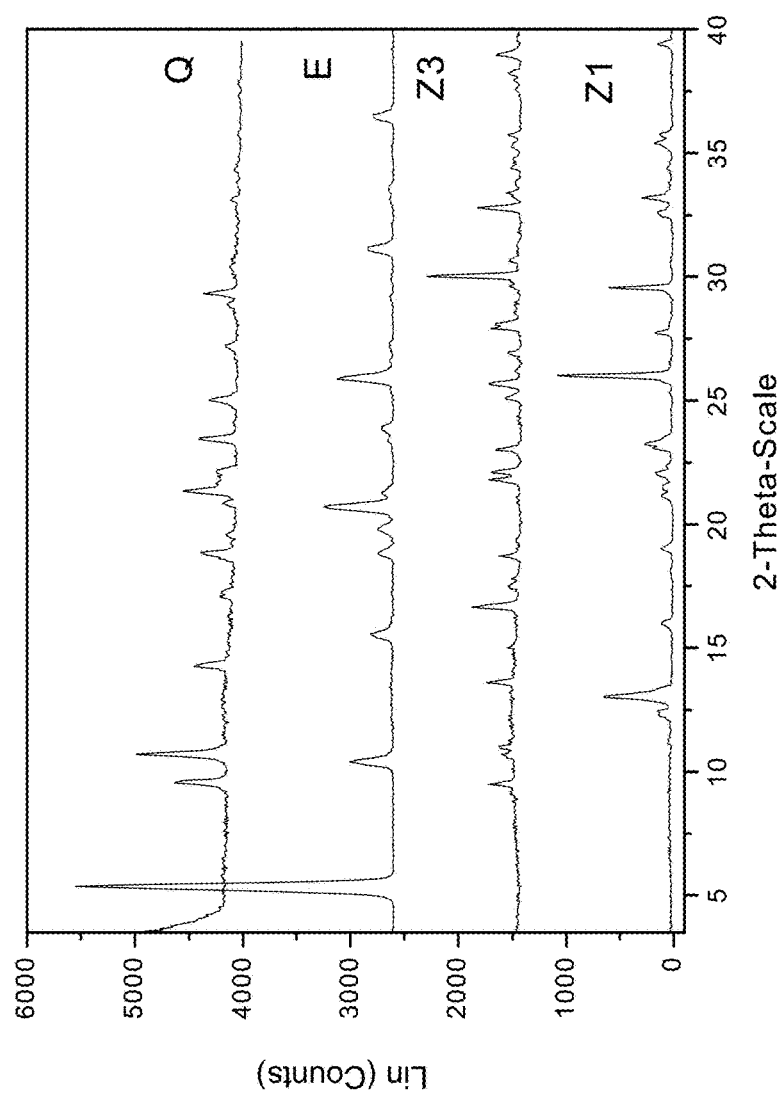
FIG. 25 shows PXRD diffractograms of: (Q=zoledronic, L-lysine, and water complex), (E=L-lysine), (Z1=Zoledronic acid monohydrate), and (Z3=Zoledronic acid trihydrate).
Figure 26:
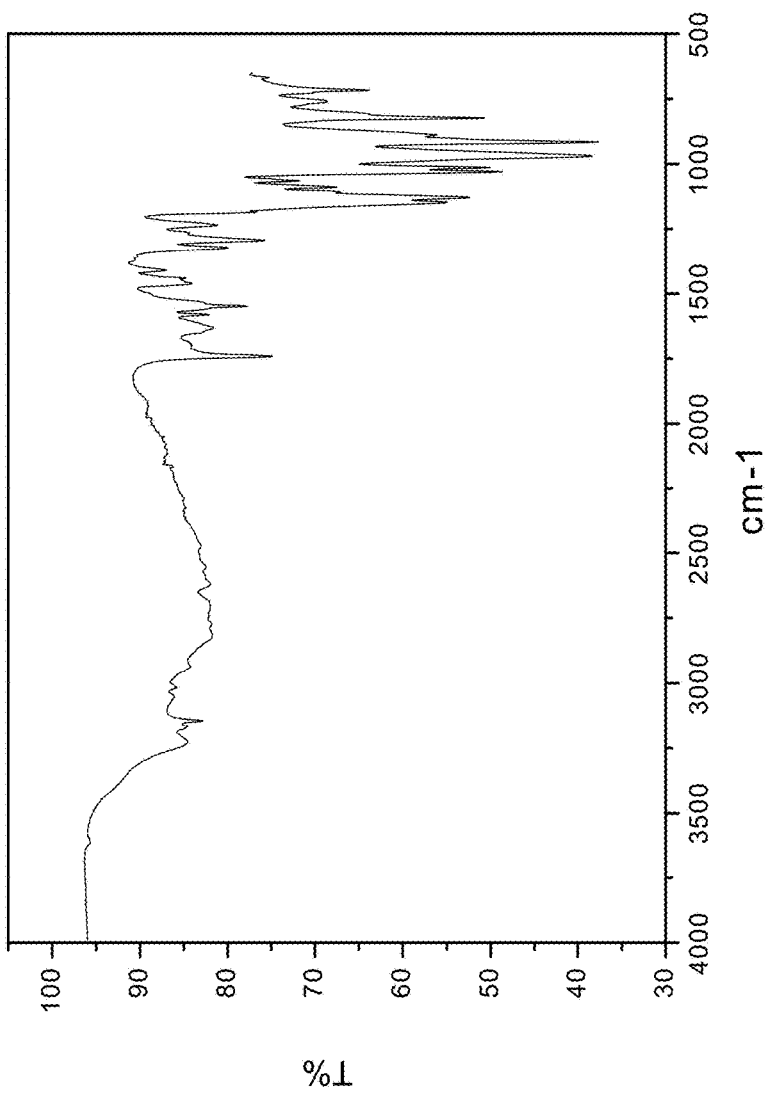
FIG. 26 is an FTIR spectrum of zoledronic, L-lysine, and water complex.

Example 15: Preparation of Zoledronic, L-Lysine, and Water Complex 1 g of zoledronic acid and 255 mg of L-lysine were dissolved in 60 mL of hot water. 100 mL of ethanol was then added as an antisolvent. The solids gathered after filtration were dried and stored in a screw cap vials for subsequent analysis. The material was characterized by PXRD and FTIR corresponding to FIG. 25 and FIG. 26 respectively.

Example 16: The Animal PK Studies

These studies were conducted on rats and dogs as they are suitable animal models for zoledronic acid. This can be attributed to the fact that both animals have historically been used in the safety evaluation and PK screening studies and are recommended by appropriate regulatory agencies. In addition, rats and dogs have also been established as appropriate species for assessing the absorption of bisphosphonate drugs including zoledronic acid. Pure zoledronic acid and zoledronic acid complexes prepared by the methods in this invention were delivered to the rats and dogs through IV or oral routes. Additional tests included ID administration in rats and administration of enteric coated capsules in dogs. All compounds delivered were well tolerated by the animals with no adverse events or physical abnormalities noticed.

Test Subjects:

8-week male Sprague-Dawley Rats (217-259 grams) were obtained from Hilltop Lab Animals, Scottdale, Pa. USA. Surgical catheters (jugular vein and intraduodenum) were implanted to the animals prior to the study. Beagle dogs from Marshall Farms, N.Y., USA, weighing from (9-12 kg) were used in this study. Surgical catheters (jugular vein) were implanted prior to the study.

Housing:

Rats were individually housed in stainless steel cages to prevent catheter exteriorization. Acclimation (Pre-dose Phase) was for 1 day. Dogs were already in the test facility (Absorption Systems Inc., USA) and did not need acclimation.

Environment:

Environmental controls for the animal room were set to maintain 18 to 26° C., a relative humidity of 30 to 70%, a minimum of 10 air changes/hour, and a 12-hour light/12-hour dark cycle. The light/dark cycle could be interrupted for study-related activities.

Diet:

For rats, water and certified Rodent Diet #8728C (Harlan Teklad) were provided. For dogs, water and the standard dog chow diet were given twice daily (every 12 hours).

Fasting:

All test animals were fasted overnight before IV, oral, or ID administration of zoledronic acid or zoledronic acid complexes.

Routes of Rat Dosing:

Zoledronic acid and its complex formulations were administered through IV, oral and ID. The doses administered to all study rats were measured as zoledronic acid, not as the complex form contained in the suspension:

i. IV Administration: the dose of zoledronic acid for IV administration was 0.5 mg/kg. The dose of each rat was calculated on a per rat basis (not on an average weight of all the rats in the lot).

ii. Oral gavage administration: solid suspensions were administered. The dose of each rat was calculated on a per rat basis (not on an average weight of all the rats in the lot). For solid suspensions, animals were administered 5 mg/kg of zoledronic acid or 5 mg/kg of zoledronic acid in zoledronic acid complexes contained in a suspension of PEG 400.

iii. Duodenal cannula administration: solid suspensions were administered. The dose of each rat was calculated on a per rat basis (not on an average weight of all the rats in the lot). For solid suspensions, animals were administered 5 mg/kg of zoledronic acid or 5 mg/kg of zoledronic acid in zoledronic acid complexes contained in a suspension of PEG 400.

Routes of Dog Dosing:

Zoledronic acid and its complex formulations were administered IV and orally. The doses administered to all study dogs were measured as zoledronic acid in each complex, not as the complex form contained in the powder in the gelatin capsule or in solution for IV:

i. IV Administration: The dose volume of each dog was adjusted based upon the average weight of the dog.
ii. Oral administration: zoledronic acid and its equivalent of zoledronic acid complex formulations were administered through size 0 or 00 gelatin capsules based on the average weight of the dogs.
iii. Oral administration with enteric coated capsules: zoledronic acid and its equivalent of zoledronic acid complex formulations were administered through size 0 enteric coated gelatin capsules based on the average weight of the dogs.
iv. Oral administration of the molecular complexes with additional coformers: physical mixtures of zoledronic acid complexes with additional coformers were administered through size 0 or 00 or 000 gelatin capsules based on the average weight of the dogs.

Groups:

Two major groups of animals were selected for the study.

Group 1, rats that contained four subgroups (I-IV) where the results of each data point on the PK profile graphs was the average drug concentration in the plasma of 3 rats.

Group 2, dog PK study contained three groups with subgroups (A, B, C, D, E and F) where the results of each data point on the PK profile graphs was the average drug concentration in the serum of 5 dogs.

Details of Group 1 Rat Dosing

Group I (IV administration). Group members, designated IV doses are listed below

| Group # I | Designation | # of rats | Dose* | Dose volume |
|---|---|---|---|---|
| G1 | Zoledronic Acid | 3 | 0.5 mg/kg | 1 mL |

IV comparator group, was conducted to calculate MAT (mean absorption time) and ka (absorption rate constant) for the oral groups.

Group II (oral gavage): Group designations and oral doses are listed below:

| Group # II | Designation | # of Rats | Dose* | Dose volume mL/kg | Compound |
|---|---|---|---|---|---|
| G2 | Zoledronic Acid in PEG400 | 3 | 5 mg/kg | 1 mL | Zoledronic acid |
| G3 | Solid suspension in PEG400 | 3 | 5 mg/kg equivalent | 1 mL | Zoledronic and glycine complex |
| G4 | Solid suspension in PEG400 | 3 | 5 mg/kg equivalent | 1 mL | Zoledronic, nicotinamide, and water complex |
| G5 | Solid suspension in PEG400 | 3 | 5 mg/kg equivalent | 1 mL | Zoledronic acid, sodium zoledronic salt, and water complex |
| G6 | Solid suspension in PEG400 | 3 | 5 mg/kg equivalent | 1 mL | Zoledronic, L-lysine, and water complex |
| G7 | Solid suspension in PEG400 | 3 | 5 mg/kg equivalent | 1 mL | Zoledronic, DL-lysine, and water complex |

Group III (ID administration): Group designations and oral doses are listed below:

| Group # III | Designation | # of rats | Dose* | Dose volume mL/kg | Compound |
|---|---|---|---|---|---|
| G8 | Zoledronic Acid in PEG400 | 3 | 5 mg/kg | 1 mL | Zoledronic acid |
| G9 | Solid suspension in PEG400 | 3 | 5 mg/kg equivalent | 1 mL | Zoledronic and glycine complex |
| G10 | Solid suspension in PEG400 | 3 | 5 mg/kg equivalent | 1 mL | Zoledronic, nicotinamide, and water complex |
| G11 | Solid suspension in PEG400 | 3 | 5 mg/kg equivalent | 1 mL | Zoledronic acid, sodium zoledronic salt, and water complex |
| G12 | Solid suspension in PEG400 | 3 | 5 mg/kg equivalent | 1 mL | Zoledronic, L-lysine, and water complex |
| G13 | Solid suspension in PEG400 | 3 | 5 mg/kg equivalent | 1 mL | Zoledronic, DL-lysine, and water complex |

Group IV (oral gavage): Group designations and oral doses are listed below:

| Group # IV | Compound | # of rats | Dose | Dose volume/kg | Excess coformer | Excess coformer amount mg/kg |
|---|---|---|---|---|---|---|
| G14 | Zoledronic and glycine complex, solid suspension in PEG400 | 3 | 5 mg/kg equivalent | 1 mL | Glycine | 45 |
| G15 | Zoledronic and glycine complex, solid suspension in PEG400 | 3 | 5 mg/kg equivalent | 1 mL | Glycine | 25 |
| G16 | Zoledronic and glycine complex, solid suspension in PEG400 | 3 | 5 mg/kg equivalent | 1 mL | Glycine | 5 |
| G17 | Zoledronic, DL-lysine, and water complex, solid suspension in PEG400 | 3 | 5 mg/kg equivalent | 1 mL | DL-lysine monohydrate | 39.32 |
| G18 | Zoledronic, DL-lysine, and water complex, solid suspension in PEG400 | 3 | 5 mg/kg equivalent | 1 mL | DL-lysine monohydrate | 28.08 |
| G19 | Zoledronic, DL-lysine, and water complex, solid suspension in PEG400 | 3 | 5 mg/kg equivalent | 1 mL | DL-lysine monohydrate | 5.62 |
| G20 | Zoledronic, DL-lysine, and water complex, solid suspension in PEG400 | 3 | 5 mg/kg equivalent | 1 mL | n/a | n/a |

Rat Blood Sample Collection, Handling and Analysis:

Blood (approx. 300 μL per sample) samples were withdrawn from each of 3 animals in Group I (IV administration) at eight (8) time points: 5 min, 15 min, 30 min, 1 hr, 2 hr, 4 hr, 8 hr, and 24 hrs, after initial administration of zoledronic acid or its complexes, into EDTA plasma tubes. Plasma was collected after centrifugation at 13,000 rpm for 5 min at 4° C. and immediately frozen and stored at −60 to −80° C. till analysis.

Samples were thawed on the day of analysis and the amount of zoledronic acid in the samples was quantified by analyzed by LC/MS/MS method.

Details of Group 2 Dog Dosing:

Prior to dosing, all dogs received a 20 mL dose of citric acid (24 mg/mL in water) to lower the pH of their stomach. After dosing capsules or IV, all dogs received additional 6.25 mL citric acid solution (24 mg/mL in water) as a rinse.

Group A, (IV administration). Group members, designated IV doses are listed below:

| Group # A | Designation | # of fasted Dogs | Dose* | Dose volume |
|---|---|---|---|---|
| Leg 1 | Zoledronic Acid | 5 | 0.05 mg/kg | 1 mL/kg |

IV comparator group, was conducted to calculate MAT (mean absorption time) and ka (absorption rate constant) for the oral groups.

Group B (oral administration): Group designations and oral doses are listed below:

| Group # B | Compound | Dosing Route | Dose of compound in the gelatin capsules | # of fasted Dogs (9-12 kg) | Dosing Solution Conc. mg/mL |
|---|---|---|---|---|---|
| Leg 2 | Zoledronic acid | oral | 5 mg/kg equivalent | 5 | n/a |
| Leg 3 | Zoledronic and glycine complex | oral | 5 mg/kg equivalent | 5 | n/a |
| Leg 4 | Zoledronic, DL-lysine, and water complex | oral | 5 mg/kg equivalent | 5 | n/a |
| Leg 5 | Zoledronic, L-lysine, and water complex | oral | 5 mg/kg equivalent | 5 | n/a |
| Leg 6 | Zoledronic, DL-lysine, and water complex | oral | 5 mg/kg equivalent | 5 | n/a |

Group C (oral administration): Group designations and oral doses are listed below:

| Group # C | Compound | # of fasted Dogs (9-12 kg) | Dosing Route | Dose of compound in the gelatin capsules | Excess coformer | Excess coformer amount |
| --- | --- | --- | --- | --- | --- | --- |
| Leg 7 | Zoledronic acid monohydrate | 5 | oral | 56.0 mg; enteric coated capsules | n/a | n/a |
| Leg 8 | Zoledronic and glycine complex | 5 | oral | 67.0 mg; enteric coated capsules | n/a | n/a |
| Leg 9 | Zoledronic, DL-lysine, and water complex | 5 | oral | 87.7 mg | DL-lysine monohydrate | 294.8 mg |
| Leg 10 | Zoledronic, DL-lysine, and water complex | 5 | oral | 87.7 mg; enteric coated capsules | DL-lysine monohydrate | 294.8 mg |
| Leg 11 | Zoledronic, DL-lysine, and water complex | 5 | oral | 84.2 mg | DL-lysine monohydrate | 294.8 mg |
| Leg 12 | Zoledronic, DL-lysine, and water complex | 5 | oral | 87.7 mg; enteric coated capsules | n/a | n/a |

Group D, (15 min IV infusion): Group members, designated IV doses are listed below:

| Group # D | Designation | # of fasted Dogs (9-12 kg) | Dose* | Dosing solution concentration |
| --- | --- | --- | --- | --- |
| Leg 13 | Zoledronic Acid | 5 | 0.183 mg/kg IV | 0.1 mg/mL |

Group E, (oral administration): Group members, designated IV doses are listed below:

| Group # E | Compound | # of fasted Dogs (9-12 kg) | Dosing Route | Dose of compound in the gelatin capsules | Excess coformer | Excess coformer amount |
| --- | --- | --- | --- | --- | --- | --- |
| Leg 14 | Zoledronic, DL-lysine, and water complex | 5 | oral | 35.4 mg | DL-lysine monohydrate | 123.8 mg |
| Leg 15 | Zoledronic and glycine complex | 5 | oral | 67.0 mg | DL-lysine monohydrate | 294.8 mg |
| Leg 16 | Zoledronic, L-lysine, and water complex | 5 | oral | 87.7 mg | DL-lysine monohydrate | 294.8 mg |
| Leg 17 | Zoledronic, DL-lysine, and water complex | 5 | oral | 35.4 mg | DL-lysine monohydrate | 294.8 mg |

Group F, (15 min IV infusion): Group members, designated IV doses are listed below:

| Group # F | Designation | # of fasted Dogs (9-12 kg) | Dose* | Dosing solution concentration |
| --- | --- | --- | --- | --- |
| Leg 18 | Zoledronic Acid | 5 | 0.12 mg/kg IV infusion | 0.1 mg/mL |

Group G (oral administration): Group designations and oral doses are listed below:

| Group # G | Compound | # of fasted Dogs (10-13 kg) | Dosing Route | Dose of compound in the gelatin capsules | Excess coformer | Excess coformer amount |
|---|---|---|---|---|---|---|
| Leg 19 | Zoledronic acid | 5 | PO | 61.3 mg | DL-lysine monohydrate | 322.9 mg |
| Leg 20 | Zoledronic, L-lysine, and water complex (2:1:2) | 5 | PO | 76.8 mg | L-lysine HCl | 359.2 mg |

Group H (oral administration): Group designations and oral doses are listed below:

| Group # H | Compound | # of fasted Dogs (9-12 kg) | Dosing Route | Dose of compound in the gelatin capsules | Excess coformer | Excess coformer amount |
|---|---|---|---|---|---|---|
| Leg 21 | Zoledronic, DL-lysine, and water complex (1:1:1) | 5 | PO | 84.2 mg | L-lysine HCl | 328.0 mg |
| Leg 22 | Zoledronic, DL-lysine, and water complex (1:1:1) | 5 | PO | 69.0 mg | DL-lysine monohydrate | 241.8 mg |
| Leg 23 | Zoledronic, L-lysine, and water complex (2:1:2) | 5 | PO | 70.1 mg | DL-lysine monohydrate | 294.9 mg |

Group J (oral administration): Group designations and oral doses are listed below:

| Group # J | Compound | # of fasted Dogs (10.5-13.5 kg) | Dosing Route | Dose of compound in the gelatin capsules | Excess coformer | Excess coformer amount |
|---|---|---|---|---|---|---|
| Leg 24 | Zoledronic acid | 5 | PO | 64.0 mg | L-lysine HCl | 374.8 mg |
| Leg 25 | Zoledronic, L-lysine, and water complex (2:1:2) | 5 | PO | 80.1 mg | N/A | N/A |
| Leg 26 | Zoledronic and glycine complex (1:1) | 5 | PO | 76.5 mg | L-lysine HCl | 374.8 mg |

Group K (oral administration): Group designations and oral doses are listed below:

| Group # K | Compound | # of fasted Dogs (8-11 kg) | Dosing Route | Dose of compound in the gelatin capsules | Excess coformer | Excess coformer amount |
|---|---|---|---|---|---|---|
| Leg 27 | Zoledronic, DL-lysine, and water complex (1:1:1) | 5 | PO | 32.0 mg | DL-lysine monohydrate | 266.8 mg |
| Leg 28 | Zoledronic, DL-lysine, and water complex (1:1:1) | 5 | PO | 76.2 mg | DL-lysine monohydrate | 266.8 mg |

Group L (oral administration): Group designations and oral doses are listed below:

| Group # L | Compound | # of fasted Dogs (8.3-11.3 kg) | Dosing Route | Dose of compound in the gelatin capsules | Excess coformer | Excess coformer amount |
|---|---|---|---|---|---|---|
| Leg 29 | Zoledronic, DL-lysine, and water complex (1:1:1) | 5 | PO | 64.4 mg | DL-lysine monohydrate | 275.2 mg |
| Leg 30 | Micronized Zoledronic, DL-lysine, and water complex (1:1:1) | 5 | PO | 64.4 mg | Micronized DL-lysine monohydrate | 275.2 mg |

Group M (oral administration): Group designations and oral doses are listed below:

| Group # M | Compound | # of fasted Dogs (8.4-11.4 kg) | Dosing Route | Dose of compound in the gelatin capsules | Excess coformer | Excess coformer amount |
|---|---|---|---|---|---|---|
| Leg 31 | Zoledronic, DL-lysine, and water complex (1:1:1) | 4 | PO | 50.8 mg | DL-lysine monohydrate | 278.0 mg |
| Leg 32 | Micronized Zoledronic, DL-lysine, and water complex (1:1:1) | 5 | PO | 50.8 mg | Micronized DL-lysine monohydrate | 278.0 mg |

After initial administration of zoledronic acid or its complexes, blood (approx. 2.5 mL per sample) was withdrawn from each of 5 animals in Group A (IV administration) at 15 time points: Pre-dose (0), 2, 5, 10, 15, 30, 45 min, 1, 1.5, 2, 4, 6, 8, 24 and 48 hrs and at 13 time points for Group B (oral administration): Pre-dose (0), 5, 10, 15, 30, 45 min, 1, 1.5, 2, 4, 6, 8, and 24 hrs. Blood samples were placed without the use of an anticoagulant and allowed to sit at room temperature for approximately 30 minutes. Samples were then centrifuged at a temperature of 4° C., at a speed of 13,000 rpm, for 5 minutes. Serum was collected and split into two aliquots and stored frozen (−80° C.) till analysis. Samples were thawed on the day of analysis and processed using analytical procedures for zoledronic acid containing an LC/MS/MS analysis method.

Animal PK Studies Results

Figure 27:
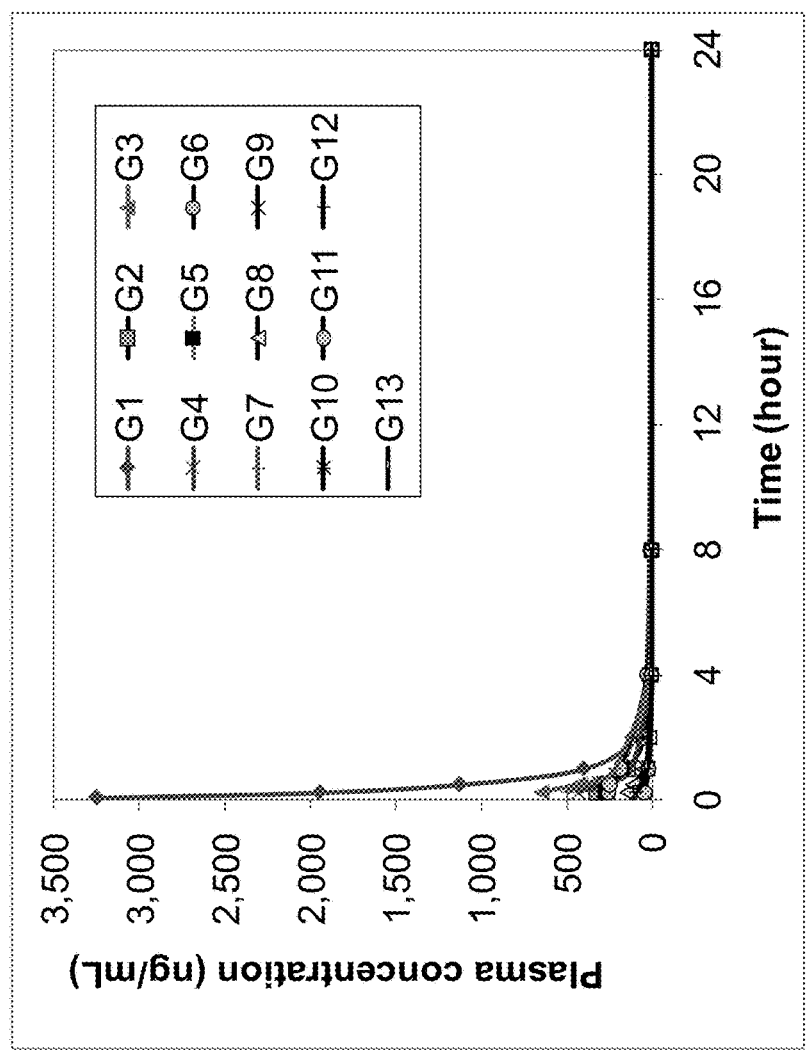
FIG. 27 shows the 24 hr rat plasma PK profile of parent zoledronic acid and zoledronic acid complexes delivered via IV, oral, and intraduodenal (ID) routes.
Figure 28:
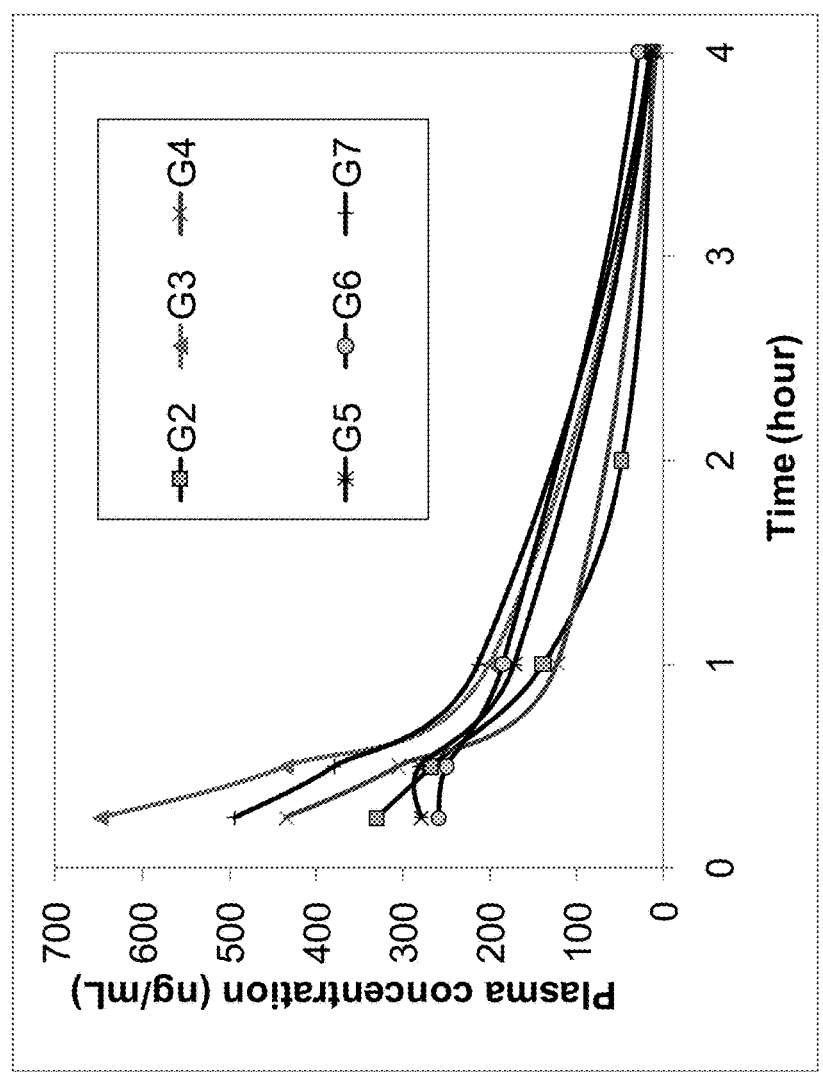
FIG. 28 shows the 4 hr rat plasma PK profile of parent zoledronic acid and zoledronic acid complexes delivered orally.
Figure 29:
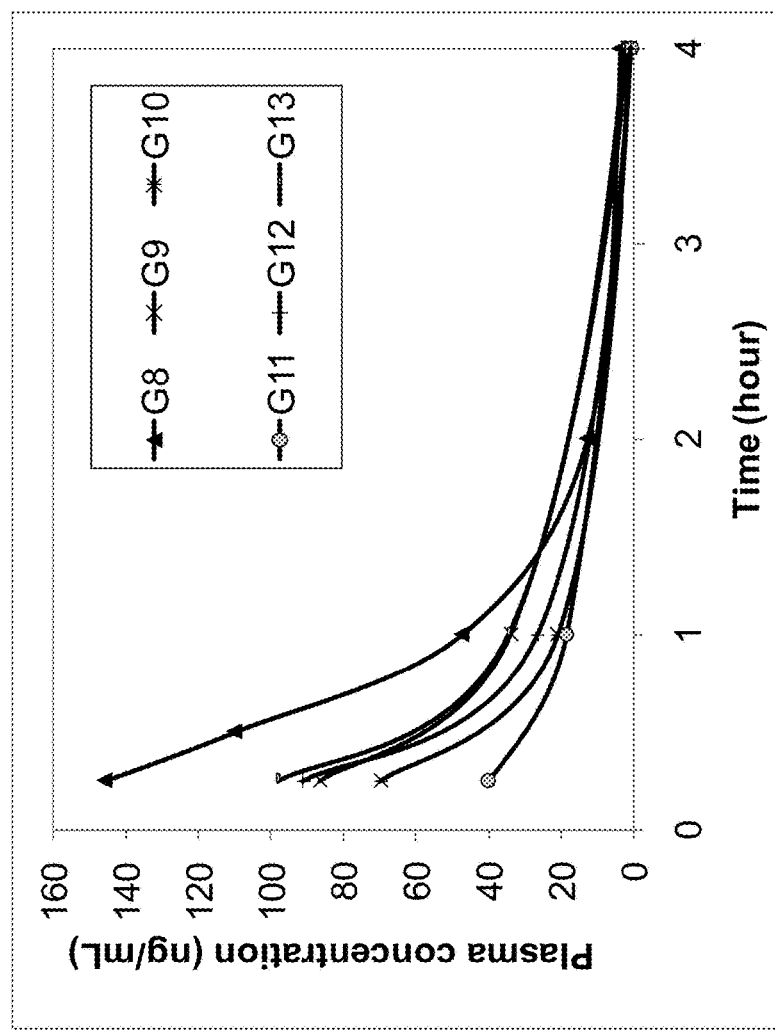
FIG. 29 shows the 4 hr rat plasma PK profile of parent zoledronic acid and zoledronic acid complexes delivered ID.
Figure 30:
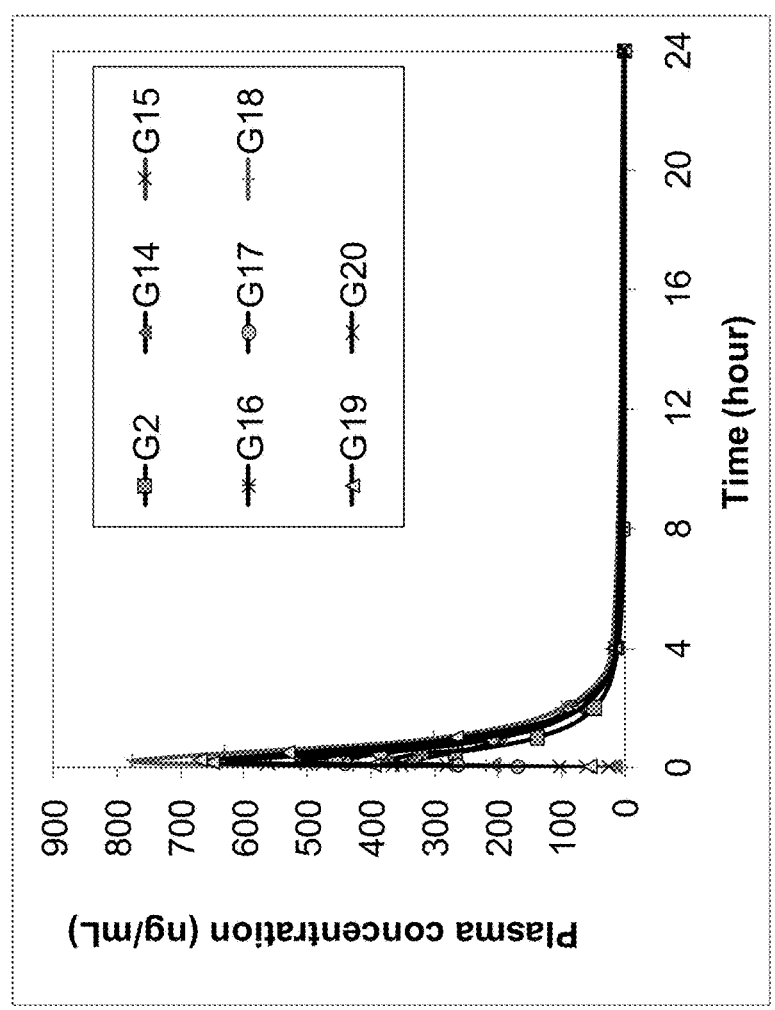
FIG. 30 shows the 24 hr rat plasma PK profile of parent zoledronic acid and zoledronic acid complexes delivered by oral gavage.
Figure 31:
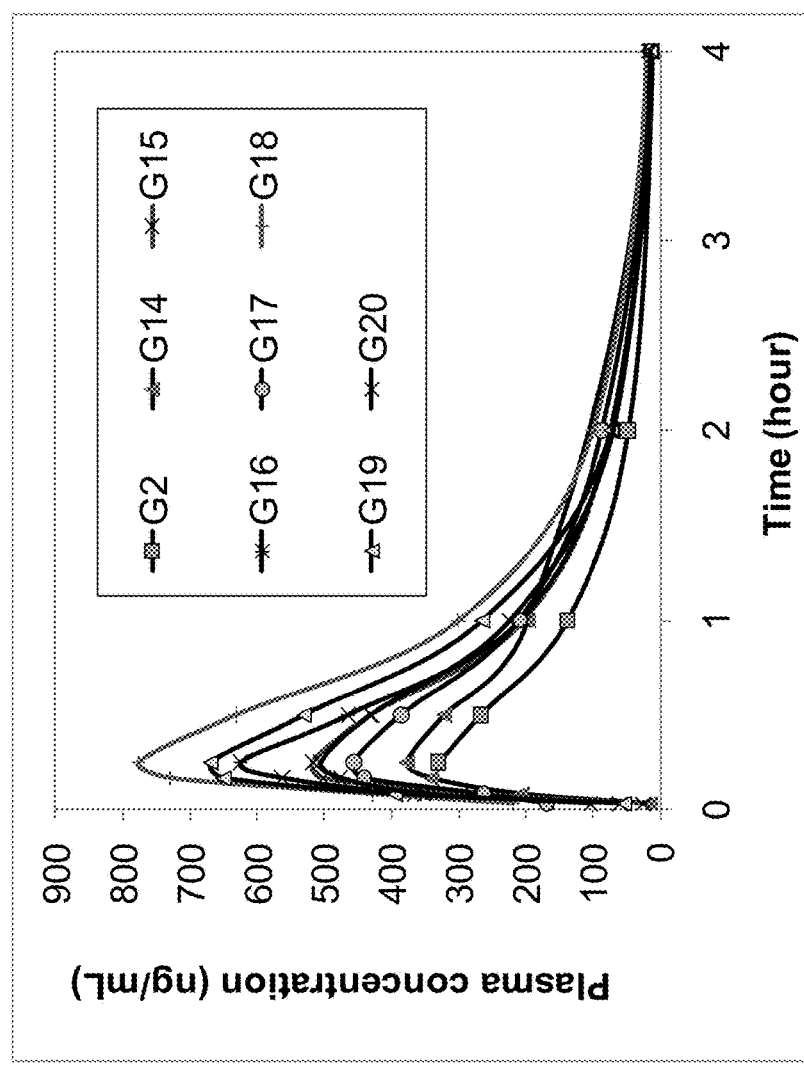
FIG. 31 shows the 4 hr rat plasma PK profile of parent zoledronic acid and zoledronic acid complexes delivered orally.
Figure 32:
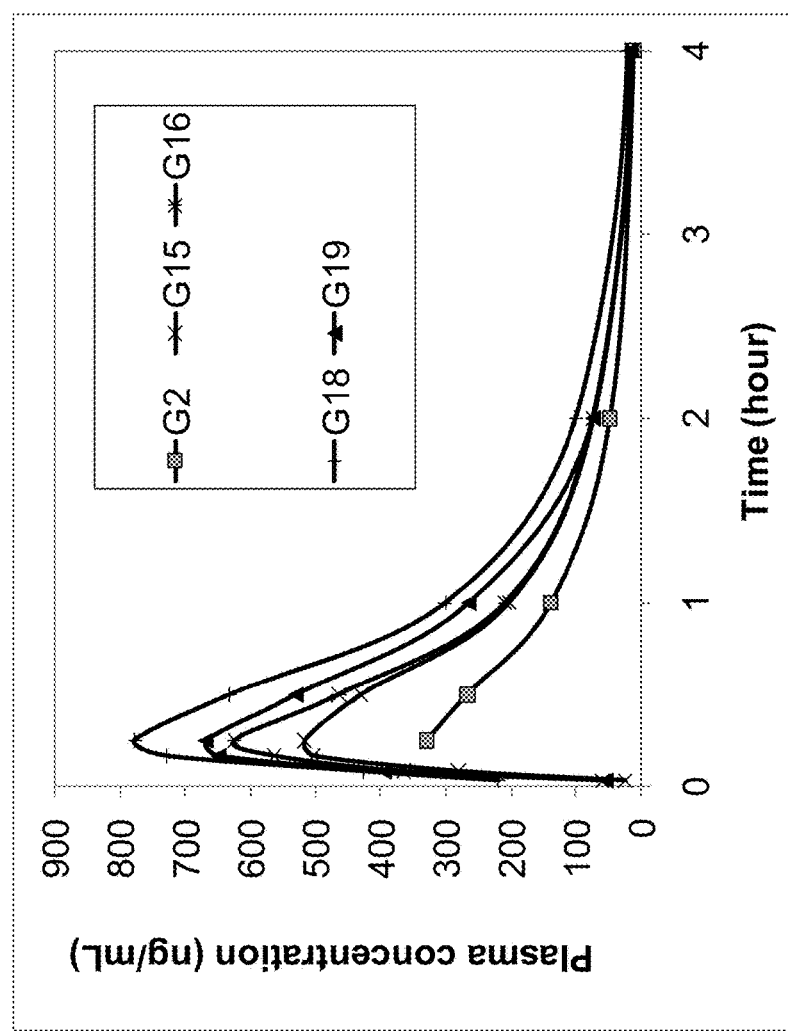
FIG. 32 shows the 4 hr rat plasma PK profile of parent zoledronic acid and selected zoledronic acid complexes delivered orally.

Rat Study:

The results of the first rat study are summarized in Table 1; the concentrations (ng/mL) of zoledronic acid in the plasma samples are the average values of the analytical results of 3 rats. In addition, the PK profiles of the IV, oral and ID groups are shown in FIG. 27. The profiles of oral and ID groups are shown in FIGS. 28 and 29. It suggests that some zoledronic acid complexes have improved oral bioavailability compared with that of the parent zoledronic acid. The complexes with improved bioavailability were further tested in a second rat PK study in which excess coformers were added to the zoledronic acid complexes and then administered to rats by oral gavage. The results of this second study are summarized in Table 2 and their PK profiles are shown in FIGS. 30, 31 and 32. These figures show improved bioavailabilities of several zoledronic acid complexes with excess coformers. The effect of excess coformers with zoledronic acid complexes in improving bioavailability is not fully understood.

Figure 33:
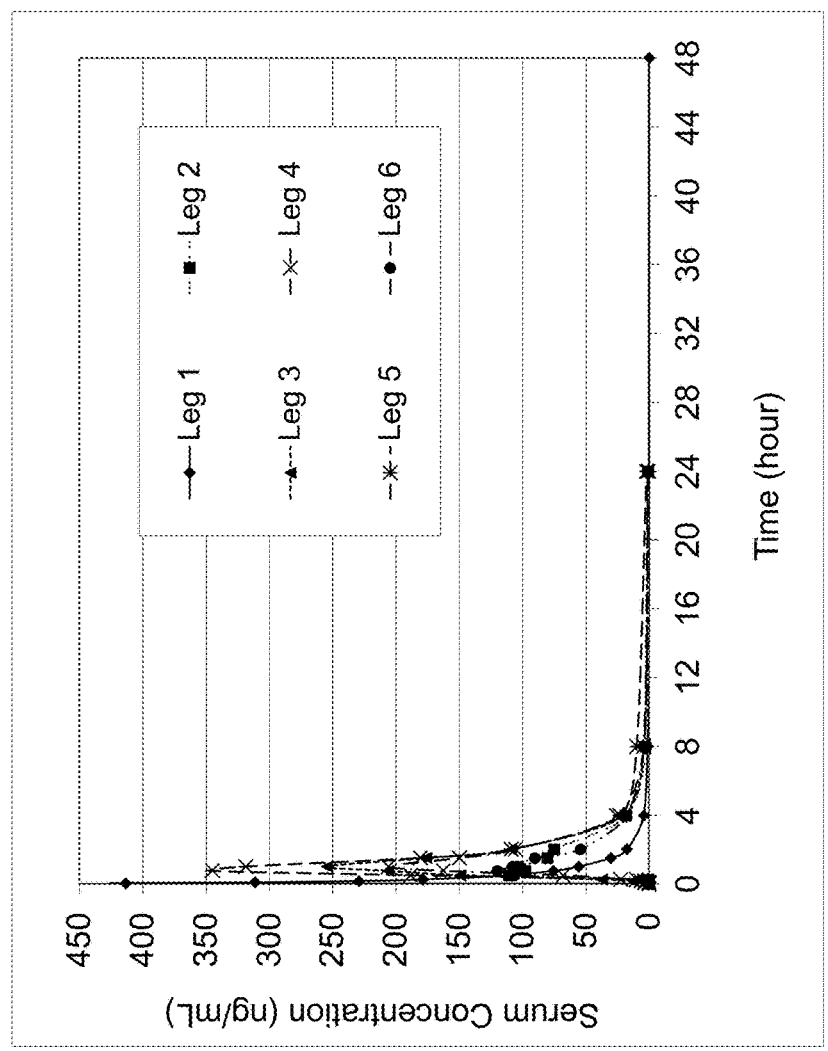
FIG. 33 shows the dog serum PK profile of parent zoledronic acid and zoledronic acid complexes delivered IV and orally.
Figure 34:
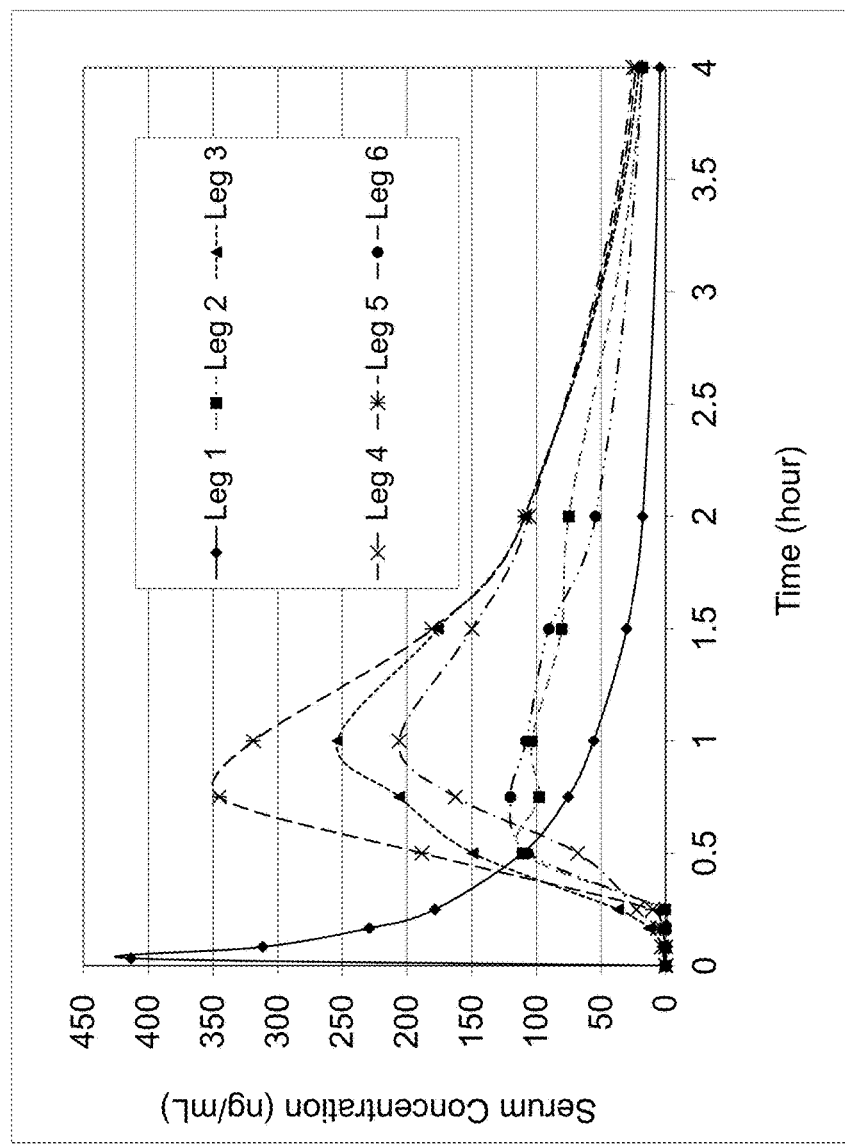
FIG. 34 shows the 4 hr dog serum PK profile of parent zoledronic acid and zoledronic acid complexes delivered IV and orally.

Dog Study:

The results of the first dog study are summarized in Table 3. The concentrations (ng/mL) of zoledronic acid are the average values of the analytical results of 5 dogs. The PK profiles of the IV and oral groups are shown in FIGS. 33 and 34 which represent the first four hours of the 48 hr PK profile. These results and FIG. 34 suggest that most if not all zoledronic acid complexes have achieved improved oral bioavailability compared to that of the parent zoledronic acid delivered orally.

Figure 35:
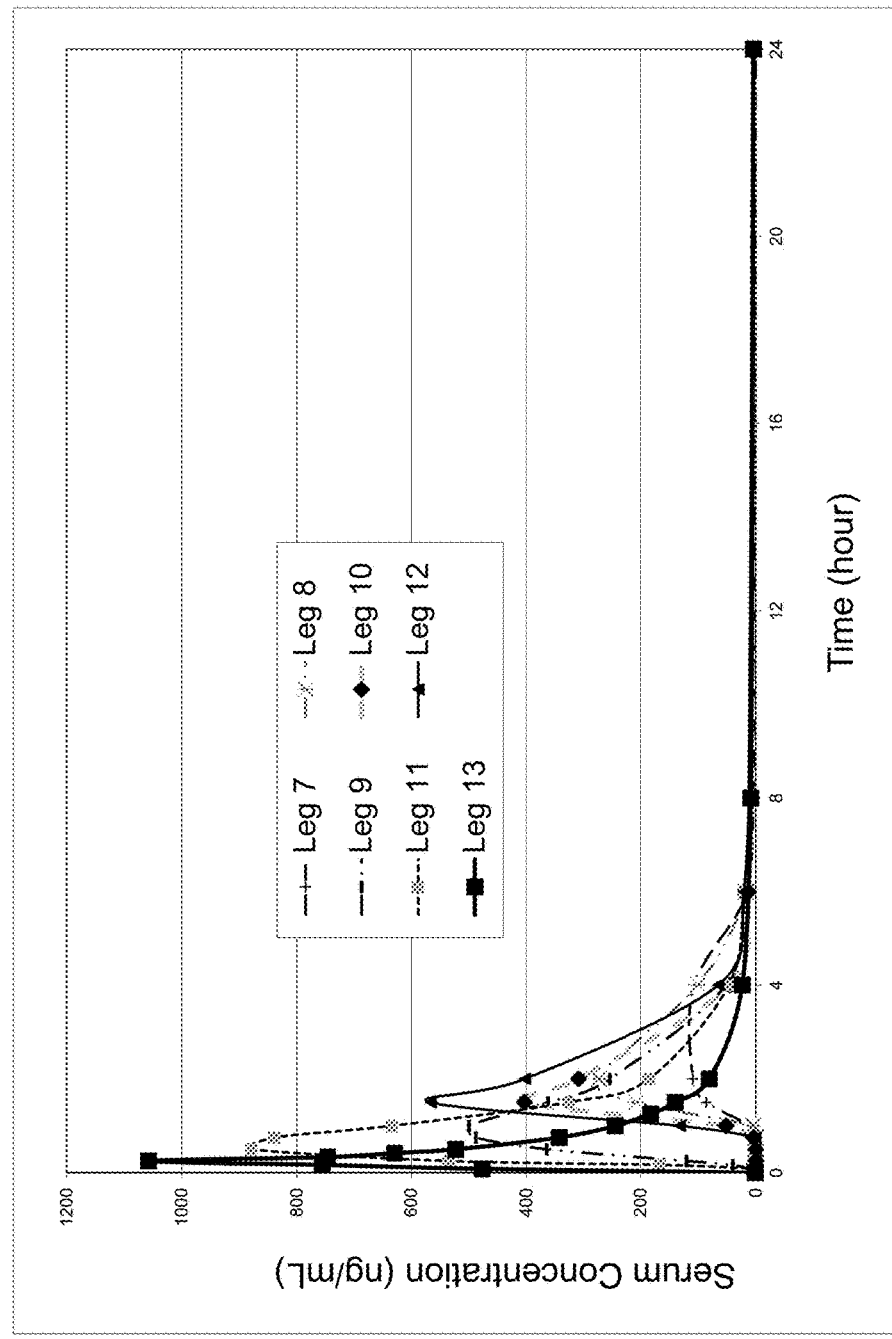
FIG. 35 shows the dog serum PK profile of parent zoledronic acid and zoledronic acid complexes delivered IV and orally; enteric and non-enteric coated capsules.
Figure 36:
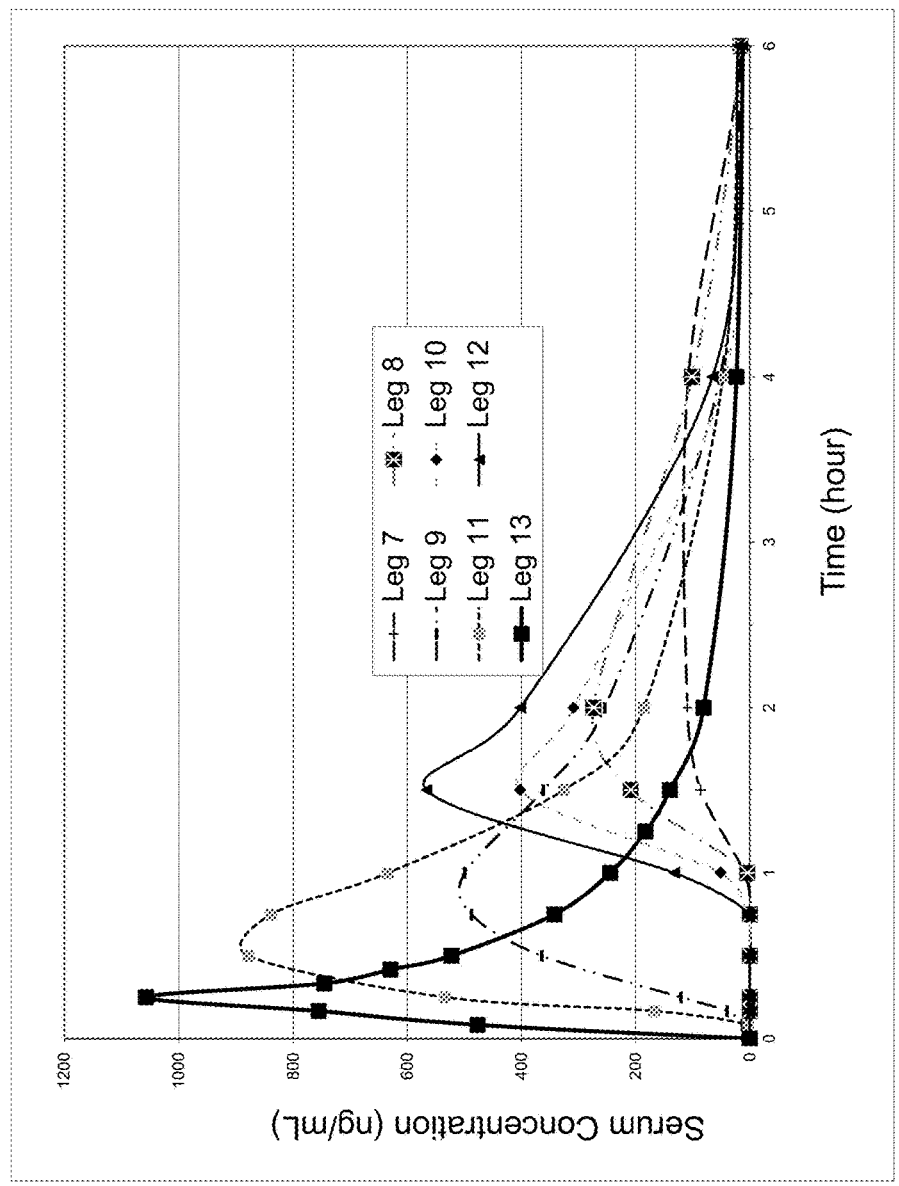
FIG. 36 shows the 6 hr dog serum PK profile of parent zoledronic acid and zoledronic acid complexes delivered IV and orally; enteric and non-enteric coated capsules.
Figure 37:
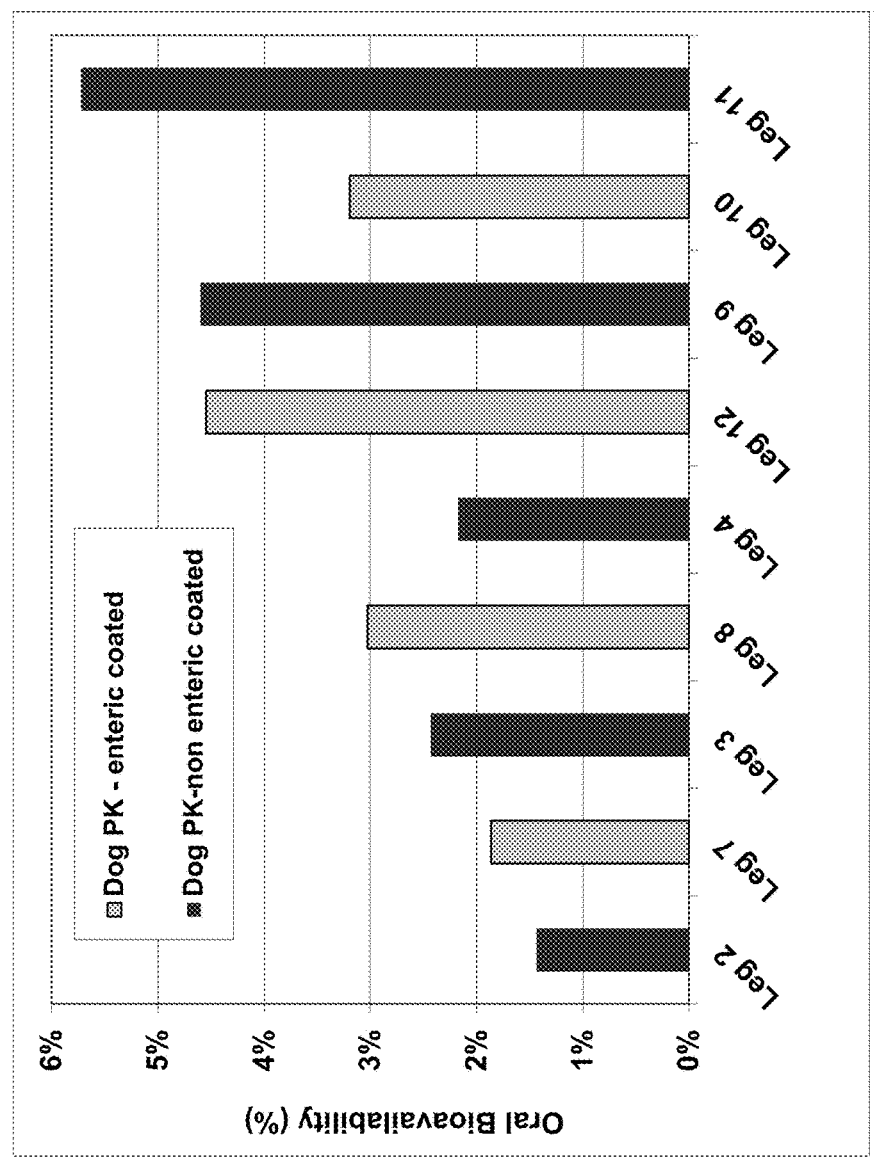
FIG. 37 shows the dog PK data for the enteric and non-enteric coated hard gelatin capsules.

The results of the second dog study are summarized in Table 4; the concentrations (ng/mL) of zoledronic acid shown are the average values of the analytical results of 5 dogs. The PK profiles of the IV and oral groups are shown in FIGS. 35 and 36. FIG. 36 represents the first 6 hours of the 24 hour PK profile. These results and FIG. 35 suggest that most if not all zoledronic acid complexes have achieved improved oral bioavailability compared with that of the parent zoledronic acid delivered orally. Specifically, there was a significant improvement in zoledronic acid bioavailability for the novel zoledronic acid complexes with excess amino acid coformer (Leg 11, FIG. 37) compared to that of the parent drug. The results have also shown that there was improvement in the bioavailability of the enterically coated capsules compared with the non-enterically coated capsules (FIG. 37, Legs 7 and 2, Legs 8 and 3, Legs 12 and 4), but surprisingly the bioavailability was significantly altered when excess amino acid coformer was added to form a physical mixture to the enterically coated capsules (FIG. 37, Legs 9 and 10). The reason behind it is not fully understood.

The results have shown that there is a slight increase in the oral bioavailability of zoledronic acid from the enteric coated capsules filled with neat (i.e. with no excess coformer) zoledronic acid amino acid complex. Therefore, it is expected that the excess coformer with the novel zoledronic acid complexes would also lead to increased bioavailability when delivered in enterically coated capsules. Surprisingly, when excess coformer was added to the zoledronic acid, the bioavailability of the enterically coated capsules was lower than that of the non-enterically coated capsules. This suggests that a physical powder mixture of the molecular complex and excess coformer might decrease the bioavailability when delivered to the duodenum. The mechanism behind this surprising finding is not yet understood.

Figure 38:
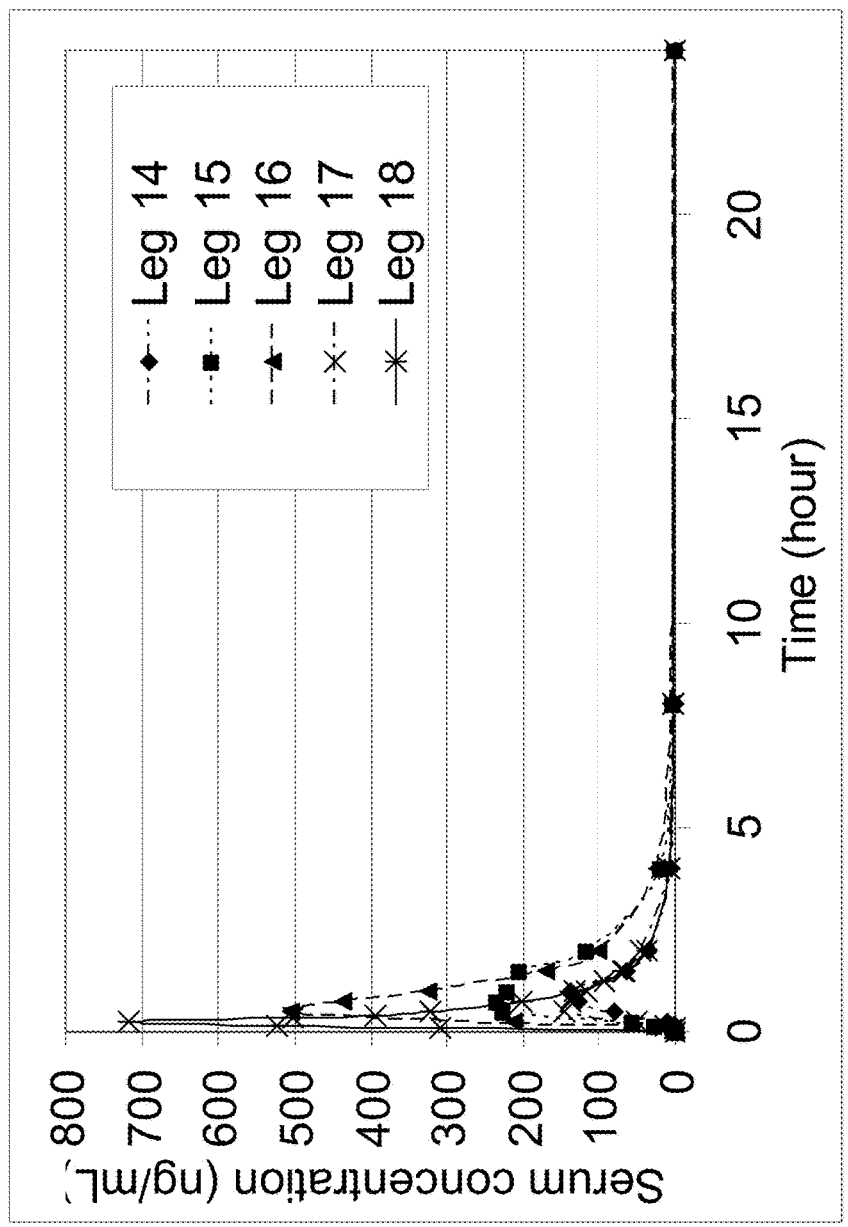
FIG. 38 shows the 24 hr dog serum PK profile of zoledronic acid complexes delivered IV and orally.
Figure 39:
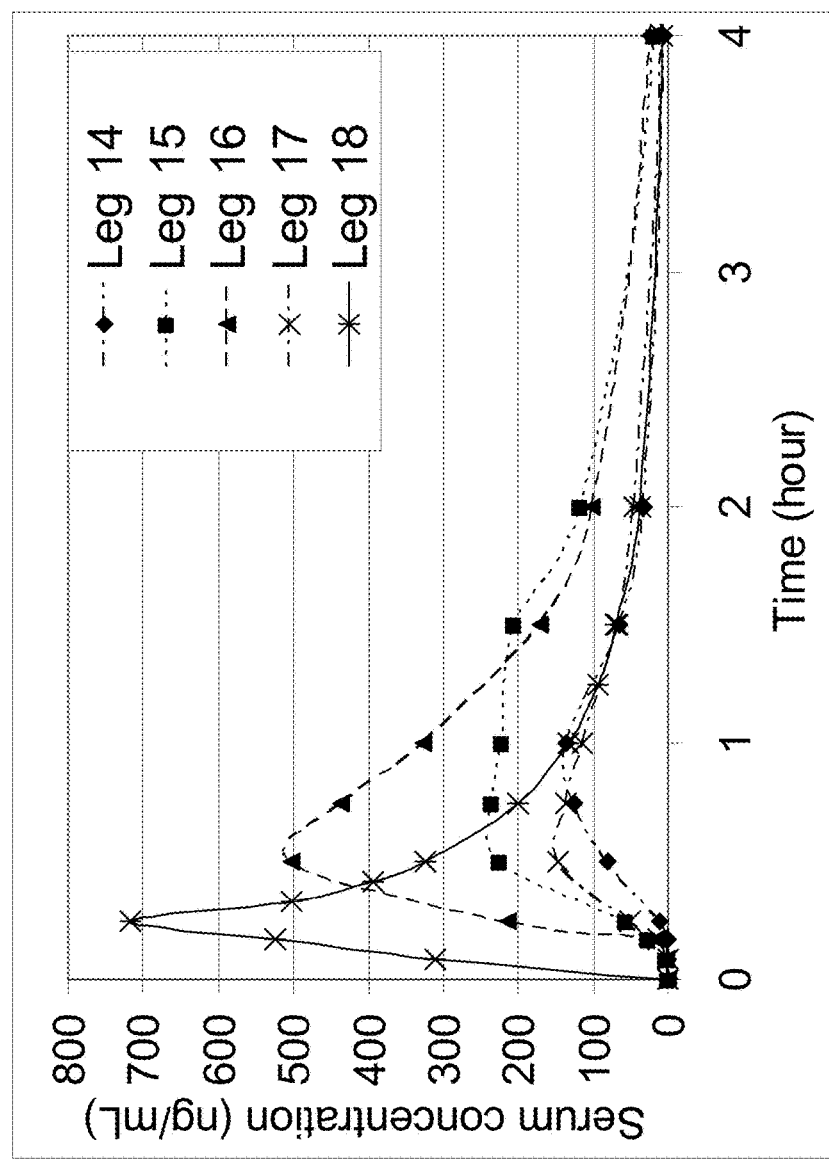
FIG. 39 shows the 4 hr dog serum PK profile of zoledronic acid complexes delivered IV and orally.

The analytical results of the third dog study are shown in Table 5, which contains averaged data from five dogs. The PK profiles of the IV and oral groups are shown in FIGS. 38 and 39. FIG. 39 represents the first 4 hours of the 24 hour PK profile.

Figure 40:
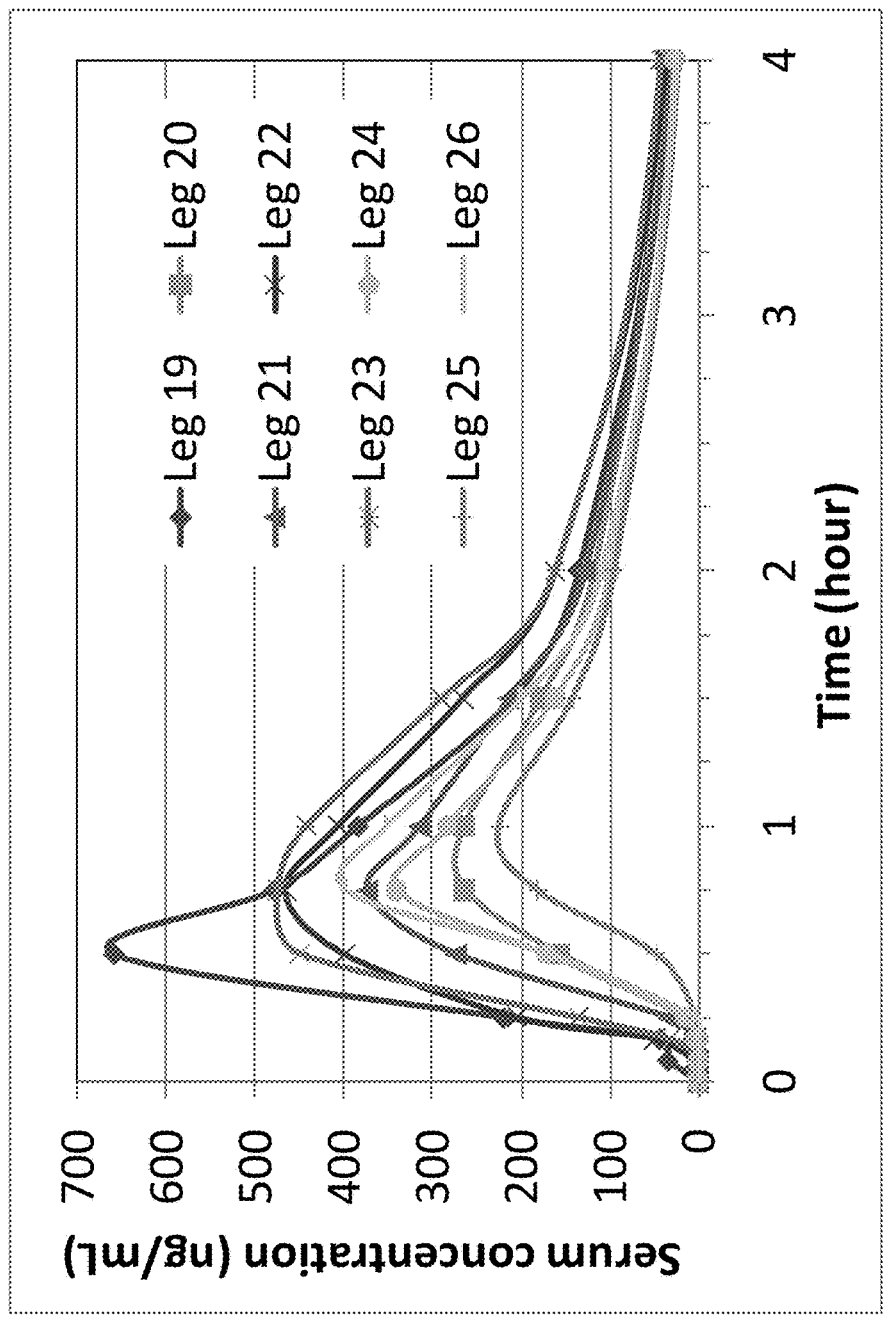
FIG. 40 shows the 4 hr dog serum PK profile of zoledronic acid complexes delivered orally.
Figure 41:
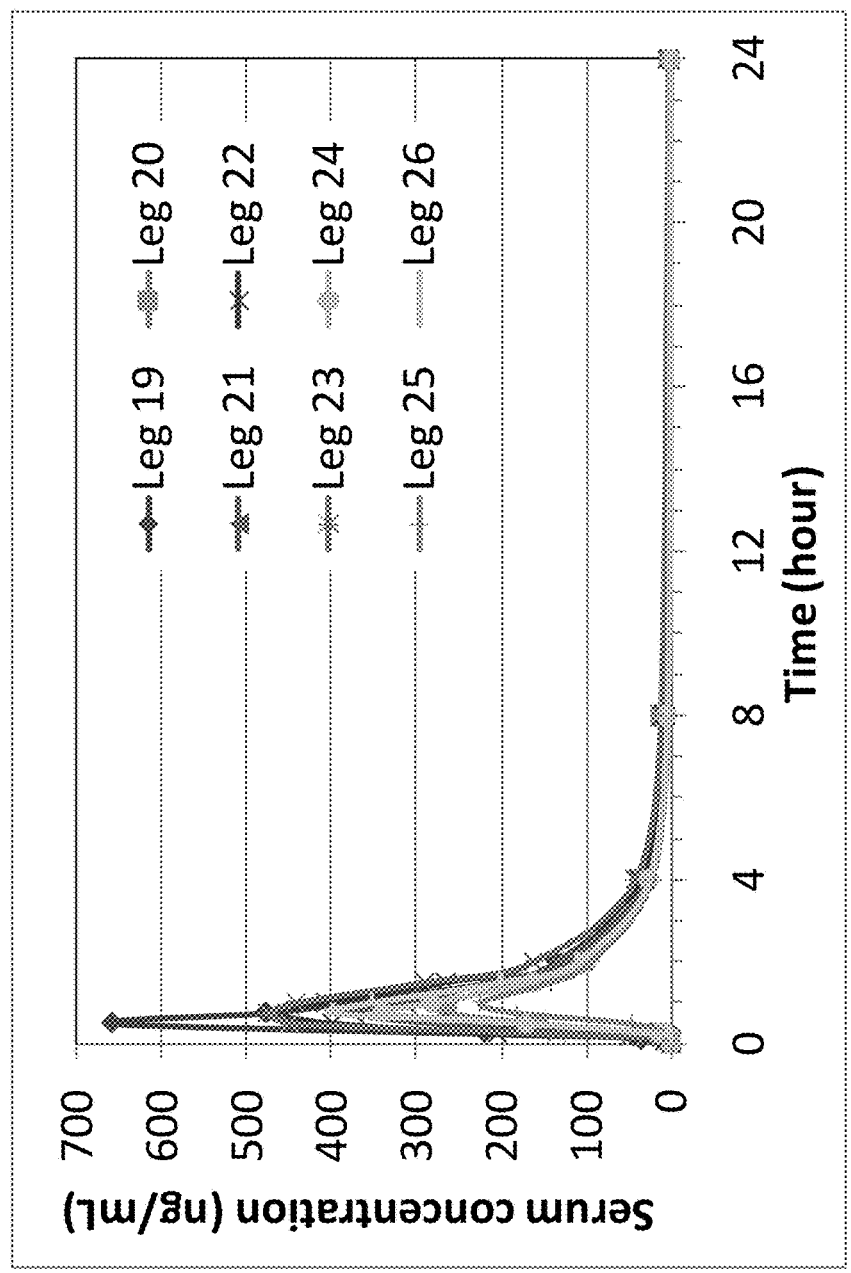
FIG. 41 shows the 24 hr dog serum PK profile of zoledronic acid complexes delivered orally.

The analytical results of the fourth dog study are shown in Table 6, which contains averaged data from five dogs. The PK profiles of the IV and oral groups are shown in FIGS. 40 and 41. FIG. 40 represents the first 4 hours of the 24 hour PK profile.

Figure 42:
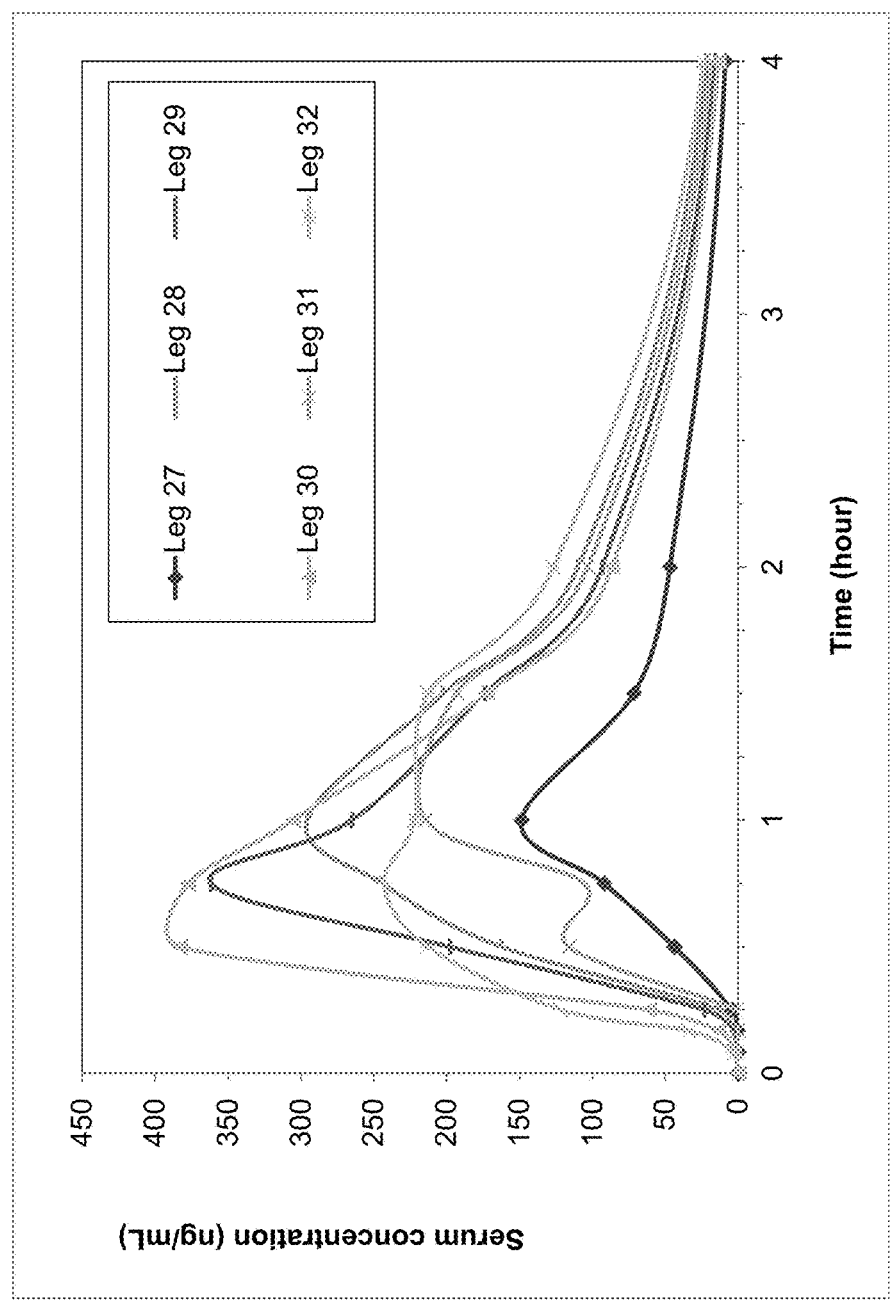
FIG. 42 shows the 4 hr dog serum PK profile of zoledronic acid complex delivered orally.
Figure 43:
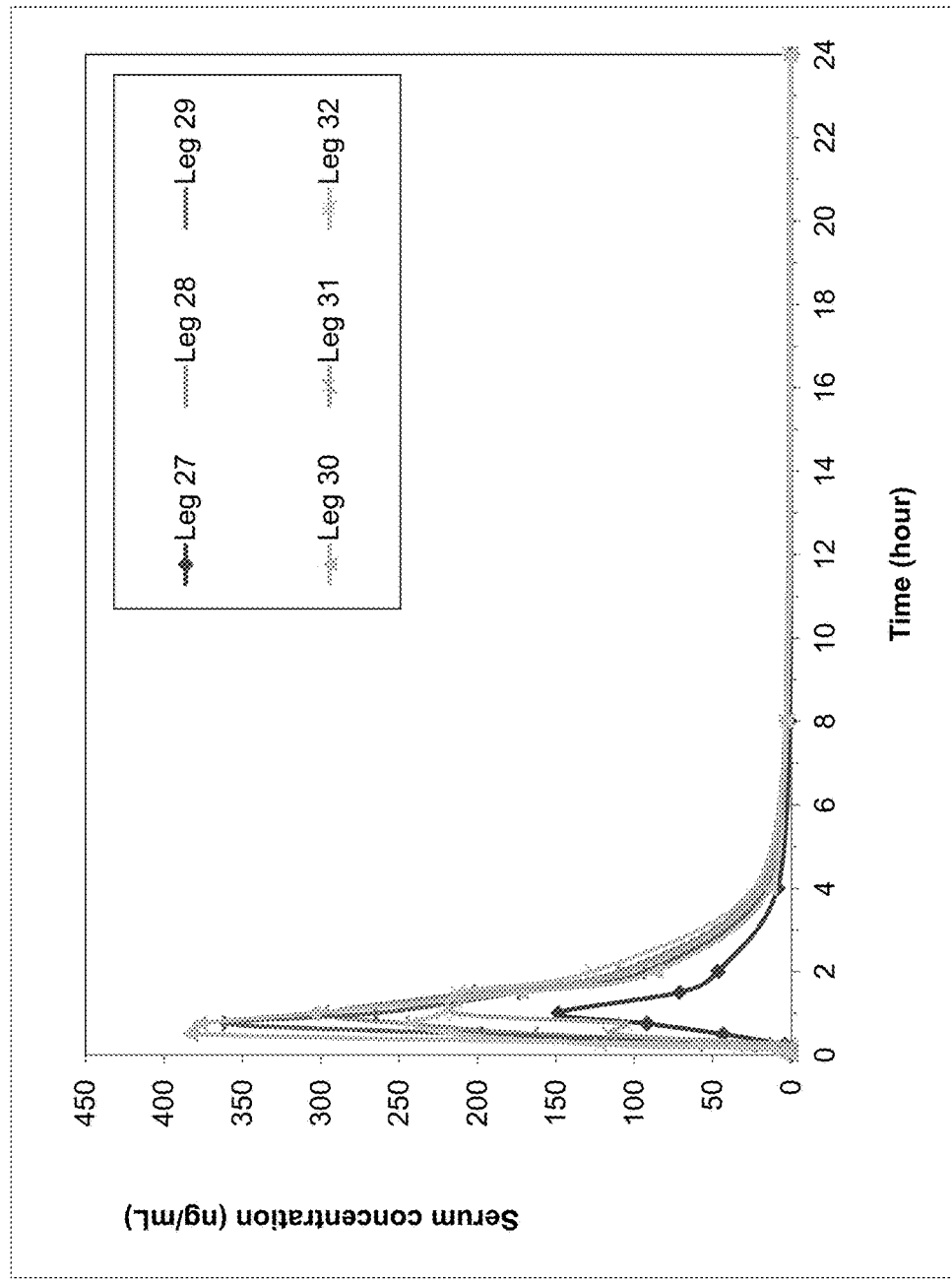
FIG. 43 shows the 24 hr dog serum PK profile of zoledronic acid complex delivered orally.

The analytical results of the fifth dog study are shown in Table 7, which contains the average data from 5 dogs with the exception of Leg 31 which is the average of 4 dogs. In this study, micronized materials (zoledronic:DL-lysine:water complex and pure DL-lysine) with size mean diameter of 5 micron by volume were used. Micronized materials were employed in our study to examine the possibility of increasing the Cmax of the drug through increasing the surface area and subsequently improving its rate of dissolution that should lead to higher concentration of the drug available for absorption through the GI tract. The results are summarized in Leg 30 and 32 in Table 7. The results of the micronized materials in both legs have shown a slight increase in the bioavailability of the drug. The PK profiles of the oral groups are shown in FIGS. 42 and 43. FIG. 42 represents the first 4 hours of the 24 hour PK profile.

TABLE 1

Rat plasma concentrations for pure zoledronic acid and zoledronic acid complexes via different routes of delivery.

| Group # | Complex | Dosing Route | Vehicle | Time (hour) | Average plasma concentration of 3 Rats (ng/mL) |
|---|---|---|---|---|---|
| G1 | Zoledronic acid | IV | Water | 0.083333 | 3254.05 |
| | | | | 0.25 | 1950.62 |
| | | | | 0.5 | 1128.75 |
| | | | | 1 | 404.28 |
| | | | | 2 | 112.68 |
| | | | | 4 | 30.46 |
| | | | | 8 | 10.66 |
| | | | | 24 | 2.98 |
| G2 | Zoledronic acid | PO | PEG 400 | 0.25 | 330.06 |
| | | | | 0.5 | 267.45 |
| | | | | 1 | 138.91 |
| | | | | 2 | 47.72 |
| | | | | 4 | 11.78 |
| | | | | 8 | 2.00 |
| | | | | 24 | 0.00 |
| G3 | Zoledronic and glycine complex | PO | PEG 400 | 0.25 | 648.01 |
| | | | | 0.5 | 435.38 |
| | | | | 1 | 200.88 |
| | | | | 4 | 12.78 |
| | | | | 8 | 1.46 |
| | | | | 24 | 0.00 |
| G4 | Zoledronic, nicotinamide, and water complex | PO | PEG 400 | 0.25 | 434.61 |
| | | | | 0.5 | 304.94 |
| | | | | 1 | 122.35 |
| | | | | 4 | 7.68 |
| | | | | 8 | 1.82 |
| | | | | 24 | 0.00 |
| G5 | Zoledronic acid, sodium zoledronic salt, and water complex | PO | PEG 400 | 0.25 | 278.47 |
| | | | | 0.5 | 280.20 |
| | | | | 1 | 171.59 |
| | | | | 4 | 13.42 |
| | | | | 8 | 1.78 |
| | | | | 24 | 0.00 |
| G6 | Zoledronic, L-lysine, and water complex | PO | PEG 400 | 0.25 | 258.43 |
| | | | | 0.5 | 249.82 |
| | | | | 1 | 184.95 |
| | | | | 4 | 28.70 |
| | | | | 8 | 3.27 |
| | | | | 24 | 0.00 |
| G7 | Zoledronic, DL-lysine, and water complex | PO | PEG 400 | 0.25 | 494.31 |
| | | | | 0.5 | 379.27 |
| | | | | 1 | 213.48 |
| | | | | 4 | 14.57 |
| | | | | 8 | 3.42 |
| | | | | 24 | 0.00 |
| G8 | Zoledronic acid | ID | PEG 400 | 0.25 | 145.67 |
| | | | | 0.5 | 109.92 |
| | | | | 1 | 47.36 |
| | | | | 2 | 12.94 |
| | | | | 4 | 3.85 |
| | | | | 8 | 0.97 |
| | | | | 24 | 0.00 |
| G9 | Zoledronic and glycine complex | ID | PEG 400 | 0.25 | 86.51 |
| | | | | 1 | 33.93 |
| | | | | 4 | 1.75 |
| | | | | 8 | 1.55 |
| | | | | 24 | 0.00 |
| G10 | Zoledronic, nicotinamide, and water complex | ID | PEG 400 | 0.25 | 69.71 |
| | | | | 1 | 21.03 |
| | | | | 4 | 0.86 |
| | | | | 8 | 0.00 |
| | | | | 24 | 0.00 |
| G11 | Zoledronic acid, sodium zoledronic salt, and water complex | ID | PEG 400 | 0.25 | 39.99 |
| | | | | 1 | 18.50 |
| | | | | 4 | 0.71 |
| | | | | 8 | 0.00 |
| | | | | 24 | 0.00 |
| G12 | Zoledronic, L-lysine, and water complex | ID | PEG 400 | 0.25 | 91.21 |
| | | | | 1 | 26.53 |
| | | | | 4 | 0.74 |
| | | | | 8 | 0.00 |
| | | | | 24 | 0.00 |
| G13 | Zoledronic, DL-lysine, and water complex | ID | PEG 400 | 0.25 | 98.25 |
| | | | | 1 | 34.61 |
| | | | | 4 | 2.65 |
| | | | | 8 | 1.02 |
| | | | | 24 | 0.80 |

TABLE 2

Rat plasma concentrations for zoledronic acid complexes with excess coformers, delivered by oral gavage

| Group # | Complex | Dosing Route | Vehicle | Time (hour) | Average plasma concentration of 3 Rats (ng/mL) |
|---|---|---|---|---|---|
| G14 | Zoledronic and glycine complex and 45 mg/kg glycine | PO | PEG 400 | 0.0333333 | 14.61 |
| | | | | 0.0833333 | 206.26 |
| | | | | 0.1666667 | 340.19 |
| | | | | 0.25 | 375.99 |
| | | | | 0.5 | 321.36 |
| | | | | 1 | 197.01 |
| | | | | 4 | 17.35 |
| | | | | 24 | 0.00 |
| G15 | Zoledronic and glycine complex and 25 mg/kg glycine | PO | PEG 400 | 0.0333333 | 24.48 |
| | | | | 0.0833333 | 281.08 |
| | | | | 0.1666667 | 502.20 |
| | | | | 0.25 | 516.58 |
| | | | | 0.5 | 430.10 |
| | | | | 1 | 203.48 |
| | | | | 2 | 73.27 |
| | | | | 4 | 14.70 |
| | | | | 24 | 0.00 |
| G16 | Zoledronic and glycine complex and 5 mg/kg glycine | PO | PEG 400 | 0.0333333 | 60.03 |
| | | | | 0.0833333 | 365.23 |
| | | | | 0.1666667 | 563.83 |
| | | | | 0.25 | 625.05 |
| | | | | 0.5 | 464.34 |
| | | | | 1 | 209.65 |
| | | | | 2 | 74.28 |
| | | | | 4 | 12.17 |
| | | | | 24 | 0.00 |
| G17 | Zoledronic, DL-lysine, and water complex and 39.32 mg/kg DL-lysine monohydrate | PO | PEG 400 | 0.0333333 | 168.19 |
| | | | | 0.0833333 | 263.28 |
| | | | | 0.1666667 | 440.26 |
| | | | | 0.25 | 456.18 |
| | | | | 0.5 | 385.57 |
| | | | | 1 | 209.26 |
| | | | | 2 | 85.65 |
| | | | | 4 | 14.58 |
| | | | | 24 | 0.71 |
| G18 | Zoledronic, DL-lysine, and water complex and 28.08 mg/kg DL-lysine monohydrate | PO | PEG 400 | 0.0333333 | 219.95 |
| | | | | 0.0833333 | 427.02 |
| | | | | 0.1666667 | 729.65 |
| | | | | 0.25 | 777.54 |
| | | | | 0.5 | 632.07 |
| | | | | 1 | 300.86 |
| | | | | 2 | 100.59 |
| | | | | 4 | 21.14 |
| | | | | 24 | 0.00 |
| G19 | Zoledronic, DL-lysine, and water complex and 5.62 mg/kg DL-lysine monohydrate | PO | PEG 400 | 0.0333333 | 53.78 |
| | | | | 0.0833333 | 394.73 |
| | | | | 0.1666667 | 649.52 |
| | | | | 0.25 | 669.20 |
| | | | | 0.5 | 530.00 |
| | | | | 1 | 265.20 |
| | | | | 2 | 73.31 |
| | | | | 4 | 15.41 |
| | | | | 24 | 0.00 |
| G20 | Zoledronic, DL-lysine, and water complex | PO | PEG 400 | 0.0333333 | 103.13 |
| | | | | 0.0833333 | 352.18 |
| | | | | 0.1666667 | 475.33 |
| | | | | 0.25 | 505.48 |
| | | | | 0.5 | 431.41 |
| | | | | 1 | 224.56 |
| | | | | 2 | 69.95 |
| | | | | 4 | 14.96 |
| | | | | 24 | 0.00 |

TABLE 3

Dog serum concentrations for pure zoledronic acid and zoledronic acid complexes via different routes of delivery (IV and oral).

| Leg # | Complex | Dosing Route | Vehicle | Time (hour) | Average serum concentration of 5 dogs (ng/mL) |
|---|---|---|---|---|---|
| 1 | 0.05 mg/kg Zoledronic acid | IV | Saline solution | 0 | 0.00 |
| | | | | 0.0333 | 413.44 |
| | | | | 0.0833 | 311.68 |
| | | | | 0.1667 | 228.97 |
| | | | | 0.25 | 178.63 |
| | | | | 0.5 | 111.11 |
| | | | | 0.75 | 75.91 |
| | | | | 1 | 56.07 |
| | | | | 1.5 | 30.35 |
| | | | | 2 | 17.61 |
| | | | | 4 | 4.29 |
| | | | | 8 | 1.13 |
| | | | | 24 | 0.00 |
| | | | | 48 | 0.00 |
| 2 | 56.0 mg Zoledronic acid monohydrate capsule | PO | n/a | 0 | 0.00 |
| | | | | 0.0833 | 0.00 |
| | | | | 0.1667 | 0.00 |
| | | | | 0.25 | 0.31 |
| | | | | 0.5 | 110.73 |
| | | | | 0.75 | 97.98 |
| | | | | 1 | 103.60 |
| | | | | 1.5 | 80.57 |
| | | | | 2 | 75.16 |
| | | | | 4 | 17.86 |
| | | | | 8 | 2.71 |
| | | | | 24 | 0.56 |
| 3 | 67.0 mg Zoledronic and glycine complex capsule | PO | n/a | 0 | 0.00 |
| | | | | 0.0833 | 2.45 |
| | | | | 0.1667 | 12.75 |
| | | | | 0.25 | 37.07 |
| | | | | 0.5 | 149.20 |
| | | | | 0.75 | 206.14 |
| | | | | 1 | 254.20 |
| | | | | 1.5 | 176.11 |
| | | | | 2 | 109.25 |
| | | | | 4 | 20.43 |
| | | | | 8 | 3.96 |
| | | | | 24 | 0.97 |
| 4 | 87.7 mg Zoledronic, DL-lysine, and water complex capsule | PO | n/a | 0 | 0.00 |
| | | | | 0.0833 | 3.11 |
| | | | | 0.1667 | 6.49 |
| | | | | 0.25 | 22.55 |
| | | | | 0.5 | 68.28 |
| | | | | 0.75 | 162.72 |
| | | | | 1 | 206.14 |
| | | | | 1.5 | 149.92 |
| | | | | 2 | 105.81 |
| | | | | 4 | 25.51 |
| | | | | 8 | 4.22 |
| | | | | 24 | 0.56 |
| 5 | 87.7 mg Zoledronic, L-lysine, and water complex capsule | PO | n/a | 0 | 0.00 |
| | | | | 0.0833 | 0.00 |
| | | | | 0.1667 | 3.13 |
| | | | | 0.25 | 10.06 |
| | | | | 0.5 | 188.52 |
| | | | | 0.75 | 345.28 |
| | | | | 1 | 318.97 |
| | | | | 1.5 | 180.77 |
| | | | | 2 | 109.23 |
| | | | | 4 | 23.11 |
| | | | | 8 | 9.73 |
| | | | | 24 | 1.93 |
| 6 | 84.2 mg Zoledronic, DL-lysine, and water complex capsule | PO | n/a | 0 | 0.00 |
| | | | | 0.0833 | 0.00 |
| | | | | 0.1667 | 0.20 |
| | | | | 0.25 | 1.92 |
| | | | | 0.5 | 106.47 |
| | | | | 0.75 | 120.13 |
| | | | | 1 | 108.13 |
| | | | | 1.5 | 90.45 |

TABLE 3-continued

Dog serum concentrations for pure zoledronic acid and zoledronic acid complexes via different routes of delivery (IV and oral).

| Leg # | Complex | Dosing Route | Vehicle | Time (hour) | Average serum concentration of 5 dogs (ng/mL) |
|---|---|---|---|---|---|
| | | | | 2 | 54.48 |
| | | | | 4 | 18.14 |
| | | | | 8 | 4.35 |
| | | | | 24 | 1.06 |

TABLE 4

Dog serum concentrations for pure zoledronic acid and zoledronic acid complexes via different routes of delivery IV and oral; enteric and non-enteric coated gelatin capsules.

| Leg # | Complex | Dosing Route | Vehicle | Time (hour) | Average serum concentration of 5 dogs (ng/mL) |
|---|---|---|---|---|---|
| 7 | 56.0 mg Zoledronic acid monohydrate enteric coated capsule | PO | n/a | 0 | 0.00 |
| | | | | 0.1667 | 0.00 |
| | | | | 0.25 | 0.00 |
| | | | | 0.5 | 0.00 |
| | | | | 0.75 | 0.00 |
| | | | | 1 | 9.84 |
| | | | | 1.5 | 86.13 |
| | | | | 2 | 109.37 |
| | | | | 4 | 107.64 |
| | | | | 6 | 14.15 |
| | | | | 8 | 4.57 |
| | | | | 24 | 0.50 |
| 8 | 67.0 mg Zoledronic and glycine complex enteric coated capsule | PO | n/a | 0 | 0.00 |
| | | | | 0.1667 | 0.00 |
| | | | | 0.25 | 0.00 |
| | | | | 0.5 | 0.00 |
| | | | | 0.75 | 0.00 |
| | | | | 1 | 4.42 |
| | | | | 1.5 | 208.97 |
| | | | | 2 | 274.53 |
| | | | | 4 | 101.20 |
| | | | | 6 | 16.71 |
| | | | | 8 | 7.14 |
| | | | | 24 | 2.17 |
| 9 | 87.7 mg Zoledronic, DL-lysine, and water complex with 294.8 mg DL-lysine monohydrate capsule | PO | n/a | 0 | 0.00 |
| | | | | 0.0833 | 13.31 |
| | | | | 0.1667 | 39.76 |
| | | | | 0.25 | 120.41 |
| | | | | 0.5 | 364.68 |
| | | | | 0.75 | 487.59 |
| | | | | 1 | 499.60 |
| | | | | 1.5 | 362.16 |
| | | | | 2 | 254.72 |
| | | | | 4 | 52.22 |
| | | | | 6 | 16.61 |
| | | | | 8 | 8.93 |
| | | | | 24 | 2.92 |
| 10 | 87.7 mg Zoledronic, DL-lysine, and water complex with 294.8 mg DL-lysine monohydrate enteric coated capsule | PO | n/a | 0 | 0.00 |
| | | | | 0.1667 | 0.00 |
| | | | | 0.25 | 0.00 |
| | | | | 0.5 | 0.00 |
| | | | | 0.75 | 3.71 |
| | | | | 1 | 51.32 |
| | | | | 1.5 | 403.15 |
| | | | | 2 | 309.08 |
| | | | | 4 | 44.83 |
| | | | | 6 | 13.15 |
| | | | | 8 | 7.09 |
| | | | | 24 | 2.66 |
| 11 | 84.2 mg Zoledronic, DL-lysine, and water complex with 294.8 mg DL-lysine monohydrate capsule | PO | n/a | 0 | 0.22 |
| | | | | 0.1667 | 167.03 |
| | | | | 0.25 | 533.96 |
| | | | | 0.5 | 878.63 |
| | | | | 0.75 | 838.82 |
| | | | | 1 | 633.50 |
| | | | | 1.5 | 326.63 |
| | | | | 2 | 185.44 |
| | | | | 4 | 46.86 |
| | | | | 6 | 20.26 |
| | | | | 8 | 11.49 |
| | | | | 24 | 5.95 |
| 12 | 87.7 mg Zoledronic, DL-lysine, and water complex enteric coated capsule | PO | n/a | 0 | 0.57 |
| | | | | 0.1667 | 0.60 |
| | | | | 0.25 | 0.59 |
| | | | | 0.5 | 0.61 |
| | | | | 0.75 | 0.40 |
| | | | | 1 | 132.15 |
| | | | | 1.5 | 566.18 |
| | | | | 2 | 402.12 |
| | | | | 4 | 65.35 |
| | | | | 6 | 21.02 |
| | | | | 8 | 12.18 |
| | | | | 24 | 4.33 |
| 13 | 0.183 mg/kg Zoledronic acid | IV | Saline solution | 0 | 0.64 |
| | | | | 0.0833 | 476.79 |
| | | | | 0.1667 | 755.68 |
| | | | | 0.25 | 1057.75 |
| | | | | 0.3333 | 745.67 |
| | | | | 0.4167 | 629.22 |
| | | | | 0.5 | 522.78 |
| | | | | 0.75 | 342.58 |
| | | | | 1 | 245.36 |
| | | | | 1.25 | 182.59 |
| | | | | 1.5 | 139.77 |
| | | | | 2 | 80.87 |
| | | | | 4 | 23.40 |
| | | | | 8 | 8.78 |
| | | | | 24 | 3.84 |

TABLE 5

Dog serum concentrations for pure zoledronic acid and zoledronic acid complexes via different routes of delivery (IV and oral).

| Leg # | Complex | Dosing Route | Vehicle | Time (hour) | Average serum concentration of 5 dogs (ng/mL) |
|---|---|---|---|---|---|
| 14 | 35.4 mg Zoledronic, DL-lysine, and water complex, with 123.8 mg DL-lysine monohydrate gelatin capsule | PO | n/a | 0 | 0.00 |
| | | | | 0.0833 | 0.00 |
| | | | | 0.1667 | 0.72 |
| | | | | 0.25 | 11.40 |
| | | | | 0.5 | 78.95 |
| | | | | 0.75 | 126.46 |
| | | | | 1 | 137.38 |
| | | | | 1.5 | 64.73 |
| | | | | 2 | 33.38 |
| | | | | 4 | 6.14 |
| | | | | 8 | 0.89 |
| | | | | 24 | 0.00 |
| 15 | 67.0 mg Zoledronic | PO | n/a | 0 | 0.00 |
| | | | | 0.0833 | 2.58 |

TABLE 5-continued

Dog serum concentrations for pure zoledronic acid and zoledronic acid complexes via different routes of delivery (IV and oral).

| Leg # | Complex | Dosing Route | Vehicle | Time (hour) | Average serum concentration of 5 dogs (ng/mL) |
|---|---|---|---|---|---|
|  | and glycine complex, with 294.8 mg DL-lysine monohydrate gelatin capsule |  |  | 0.1667 | 26.13 |
|  |  |  |  | 0.25 | 55.58 |
|  |  |  |  | 0.5 | 225.41 |
|  |  |  |  | 0.75 | 234.95 |
|  |  |  |  | 1 | 221.91 |
|  |  |  |  | 1.5 | 204.90 |
|  |  |  |  | 2 | 117.22 |
|  |  |  |  | 4 | 17.79 |
|  |  |  |  | 8 | 3.34 |
|  |  |  |  | 24 | 0.77 |
| 16 | 87.7 mg Zoledronic, L-lysine, and water complex, with 294.8 mg DL-lysine monohydrate gelatin capsule | PO | n/a | 0 | 0.00 |
|  |  |  |  | 0.0833 | 3.26 |
|  |  |  |  | 0.1667 | 17.21 |
|  |  |  |  | 0.25 | 213.77 |
|  |  |  |  | 0.5 | 504.17 |
|  |  |  |  | 0.75 | 436.00 |
|  |  |  |  | 1 | 325.21 |
|  |  |  |  | 1.5 | 171.42 |
|  |  |  |  | 2 | 100.81 |
|  |  |  |  | 4 | 23.38 |
|  |  |  |  | 8 | 4.65 |
|  |  |  |  | 24 | 1.48 |
| 17 | 35.4 mg Zoledronic, DL-lysine, and water complex, with 294.8 mg DL-lysine monohydrate gelatin capsule | PO | n/a | 0 | 0.00 |
|  |  |  |  | 0.0833 | 0.00 |
|  |  |  |  | 0.1667 | 13.47 |
|  |  |  |  | 0.25 | 50.04 |
|  |  |  |  | 0.5 | 146.68 |
|  |  |  |  | 0.75 | 137.24 |
|  |  |  |  | 1 | 116.38 |
|  |  |  |  | 1.5 | 66.70 |
|  |  |  |  | 2 | 44.94 |
|  |  |  |  | 4 | 8.87 |
|  |  |  |  | 8 | 1.58 |
|  |  |  |  | 24 | 0.21 |
| 18 | 0.12 mg/kg Zoledronic acid | IV | Saline solution | 0 | 0.00 |
|  |  |  |  | 0.0833 | 309.13 |
|  |  |  |  | 0.1667 | 524.58 |
|  |  |  |  | 0.25 | 717.15 |
|  |  |  |  | 0.3333 | 501.70 |
|  |  |  |  | 0.4167 | 392.35 |
|  |  |  |  | 0.5 | 322.84 |
|  |  |  |  | 0.75 | 201.78 |
|  |  |  |  | 1 | 132.86 |
|  |  |  |  | 1.25 | 93.22 |
|  |  |  |  | 1.5 | 69.06 |
|  |  |  |  | 2 | 38.38 |
|  |  |  |  | 4 | 9.14 |
|  |  |  |  | 8 | 3.24 |
|  |  |  |  | 24 | 1.21 |

TABLE 6

Dog serum concentrations for pure zoledronic acid and zoledronic acid complexes delivered orally.

| Leg # | Complex | Dosing Route | Vehicle | Time (hour) | Average plasma concentration of 5 dogs (ng/mL) |
|---|---|---|---|---|---|
| 19 | 61.3 mg Zoledronic acid, with 322.9 mg DL-lysine monohydrate gelatin capsule | PO | n/a | 0 | 0.00 |
|  |  |  |  | 0.0833 | 34.10 |
|  |  |  |  | 0.1667 | 42.74 |
|  |  |  |  | 0.25 | 219.76 |
|  |  |  |  | 0.5 | 659.25 |
|  |  |  |  | 0.75 | 478.77 |
|  |  |  |  | 1 | 383.80 |
|  |  |  |  | 1.5 | 209.87 |
|  |  |  |  | 2 | 135.97 |
|  |  |  |  | 4 | 34.22 |
|  |  |  |  | 8 | 8.53 |
|  |  |  |  | 24 | 2.07 |
| 20 | 76.8 mg Zoledronic, L-lysine, and water complex (2:1:2), with 359.2 mg L-lysine HCl gelatin capsule | PO | n/a | 0 | 0.20 |
|  |  |  |  | 0.0833 | 0.21 |
|  |  |  |  | 0.1667 | 4.10 |
|  |  |  |  | 0.25 | 12.03 |
|  |  |  |  | 0.5 | 156.89 |
|  |  |  |  | 0.75 | 263.80 |
|  |  |  |  | 1 | 265.48 |
|  |  |  |  | 1.5 | 178.89 |
|  |  |  |  | 2 | 118.73 |
|  |  |  |  | 4 | 36.12 |
|  |  |  |  | 8 | 12.32 |
|  |  |  |  | 24 | 2.56 |
| 21 | 84.2 mg Zoledronic, DL-lysine, and water complex (1:1:1), with 328.0 mg L-lysine HCl gelatin capsule | PO | n/a | 0 | 0.00 |
|  |  |  |  | 0.0833 | 0.20 |
|  |  |  |  | 0.1667 | 5.77 |
|  |  |  |  | 0.25 | 32.62 |
|  |  |  |  | 0.5 | 273.09 |
|  |  |  |  | 0.75 | 373.00 |
|  |  |  |  | 1 | 314.46 |
|  |  |  |  | 1.5 | 214.18 |
|  |  |  |  | 2 | 128.08 |
|  |  |  |  | 4 | 30.87 |
|  |  |  |  | 8 | 6.80 |
|  |  |  |  | 24 | 2.12 |
| 22 | 69.0 mg Zoledronic, DL-lysine, and water complex (1:1:1), with 241.8 mg DL-lysine monohydrate gelatin capsule | PO | n/a | 0 | 0.00 |
|  |  |  |  | 0.0833 | 7.35 |
|  |  |  |  | 0.1667 | 48.84 |
|  |  |  |  | 0.25 | 204.61 |
|  |  |  |  | 0.5 | 398.98 |
|  |  |  |  | 0.75 | 465.56 |
|  |  |  |  | 1 | 406.10 |
|  |  |  |  | 1.5 | 265.75 |
|  |  |  |  | 2 | 161.63 |
|  |  |  |  | 4 | 36.68 |
|  |  |  |  | 8 | 9.66 |
|  |  |  |  | 24 | 3.45 |
| 23 | 70.1 mg Zoledronic, L-lysine, and water complex (2:1:2), with 294.9 mg DL-lysine monohydrate gelatin capsule | PO | n/a | 0 | 0.52 |
|  |  |  |  | 0.0833 | 1.99 |
|  |  |  |  | 0.1667 | 31.45 |
|  |  |  |  | 0.25 | 135.92 |
|  |  |  |  | 0.5 | 449.28 |
|  |  |  |  | 0.75 | 474.97 |
|  |  |  |  | 1 | 442.86 |
|  |  |  |  | 1.5 | 290.01 |
|  |  |  |  | 2 | 162.59 |
|  |  |  |  | 4 | 42.25 |
|  |  |  |  | 8 | 10.77 |
|  |  |  |  | 24 | 3.28 |
| 24 | 64.0 mg Zoledronic acid, with 374.8 mg L-lysine HCl gelatin capsule | PO | n/a | 0 | 0.00 |
|  |  |  |  | 0.0833 | 0.00 |
|  |  |  |  | 0.1667 | 1.20 |
|  |  |  |  | 0.25 | 14.11 |
|  |  |  |  | 0.5 | 171.59 |
|  |  |  |  | 0.75 | 340.09 |
|  |  |  |  | 1 | 283.01 |
|  |  |  |  | 1.5 | 162.59 |
|  |  |  |  | 2 | 99.96 |
|  |  |  |  | 4 | 26.27 |
|  |  |  |  | 8 | 4.56 |
|  |  |  |  | 24 | 0.89 |
| 25 | 80.1 mg Zoledronic, L-lysine, | PO | n/a | 0 | 0.00 |
|  |  |  |  | 0.0833 | 0.00 |
|  |  |  |  | 0.1667 | 0.32 |

TABLE 6-continued

Dog serum concentrations for pure zoledronic acid and zoledronic acid complexes delivered orally.

| Leg # | Complex | Dosing Route | Vehicle | Time (hour) | Average plasma concentration of 5 dogs (ng/mL) |
|---|---|---|---|---|---|
|  | and water complex (2:1:2) gelatin capsule |  |  | 0.25 | 2.16 |
|  |  |  |  | 0.5 | 47.70 |
|  |  |  |  | 0.75 | 181.00 |
|  |  |  |  | 1 | 224.61 |
|  |  |  |  | 1.5 | 142.02 |
|  |  |  |  | 2 | 95.10 |
|  |  |  |  | 4 | 23.06 |
|  |  |  |  | 8 | 3.97 |
|  |  |  |  | 24 | 1.20 |
| 26 | 76.5 mg Zoledronic and glycine complex (1:1), with 374.8 mg L-lysine HCl gelatin capsule | PO | n/a | 0 | 0.00 |
|  |  |  |  | 0.0833 | 0.00 |
|  |  |  |  | 0.1667 | 0.85 |
|  |  |  |  | 0.25 | 3.18 |
|  |  |  |  | 0.5 | 169.29 |
|  |  |  |  | 0.75 | 397.95 |
|  |  |  |  | 1 | 352.39 |
|  |  |  |  | 1.5 | 200.22 |
|  |  |  |  | 2 | 109.96 |
|  |  |  |  | 4 | 25.15 |
|  |  |  |  | 8 | 4.34 |
|  |  |  |  | 24 | 1.66 |

TABLE 7

Dog serum concentrations for zoledronic, DL-lysine and water complex delivered orally at different doses.

| Leg # | Complex | Dosing Route | Vehicle | Time (hour) | Average plasma concentration of 5 dogs (ng/mL) |
|---|---|---|---|---|---|
| 27 | 32.0 mg Zoledronic, DL-lysine, and water complex (1:1:1), with 266.8 mg DL-lysine monohydrate gelatin capsule | PO | n/a | 0 | 0.00 |
|  |  |  |  | 0.0833 | 0.00 |
|  |  |  |  | 0.1667 | 0.52 |
|  |  |  |  | 0.25 | 4.25 |
|  |  |  |  | 0.5 | 43.64 |
|  |  |  |  | 0.75 | 91.85 |
|  |  |  |  | 1 | 148.71 |
|  |  |  |  | 1.5 | 71.25 |
|  |  |  |  | 2 | 46.68 |
|  |  |  |  | 4 | 8.83 |
|  |  |  |  | 8 | 1.02 |
|  |  |  |  | 24 | 0.00 |
| 28 | 76.2 mg Zoledronic, DL-lysine, and water complex (1:1:1), with 266.8 mg DL-lysine monohydrate gelatin capsule | PO | n/a | 0 | 0.00 |
|  |  |  |  | 0.0833 | 0.37 |
|  |  |  |  | 0.1667 | 3.48 |
|  |  |  |  | 0.25 | 12.59 |
|  |  |  |  | 0.5 | 162.37 |
|  |  |  |  | 0.75 | 244.28 |
|  |  |  |  | 1 | 295.79 |
|  |  |  |  | 1.5 | 202.36 |
|  |  |  |  | 2 | 110.16 |
|  |  |  |  | 4 | 21.43 |
|  |  |  |  | 8 | 3.16 |
|  |  |  |  | 24 | 0.81 |
| 29 | 64.4 mg Zoledronic, DL-lysine, and water complex (1:1:1), with 275.2 mg DL-lysine | PO | n/a | 0 | 0.00 |
|  |  |  |  | 0.0833 | 0.00 |
|  |  |  |  | 0.1667 | 2.10 |
|  |  |  |  | 0.25 | 23.08 |
|  |  |  |  | 0.5 | 197.71 |
|  |  |  |  | 0.75 | 361.80 |
|  |  |  |  | 1 | 264.70 |
|  |  |  |  | 1.5 | 173.72 |
|  |  |  |  | 2 | 93.35 |

TABLE 7-continued

Dog serum concentrations for zoledronic, DL-lysine and water complex delivered orally at different doses.

| Leg # | Complex | Dosing Route | Vehicle | Time (hour) | Average plasma concentration of 5 dogs (ng/mL) |
|---|---|---|---|---|---|
|  | monohydrate gelatin capsule |  |  | 4 | 15.54 |
|  |  |  |  | 8 | 2.97 |
|  |  |  |  | 24 | 0.71 |
| 30 | 64.4 mg micronized Zoledronic, DL-lysine, and water complex (1:1:1), with 275.2 mg micronized DL-lysine monohydrate gelatin capsule | PO | n/a | 0 | 0.00 |
|  |  |  |  | 0.0833 | 2.95 |
|  |  |  |  | 0.1667 | 13.08 |
|  |  |  |  | 0.25 | 61.19 |
|  |  |  |  | 0.5 | 383.13 |
|  |  |  |  | 0.75 | 377.27 |
|  |  |  |  | 1 | 305.30 |
|  |  |  |  | 1.5 | 172.67 |
|  |  |  |  | 2 | 86.54 |
|  |  |  |  | 4 | 13.56 |
|  |  |  |  | 8 | 3.52 |
|  |  |  |  | 24 | 0.87 |
| 31 | 50.8 mg Zoledronic, DL-lysine, and water complex (1:1:1), with 278.0 mg DL-lysine monohydrate gelatin capsule | PO | n/a | 0 | 0.00 |
|  |  |  |  | 0.0833 | 0.00 |
|  |  |  |  | 0.1667 | 0.00 |
|  |  |  |  | 0.25 | 1.50 |
|  |  |  |  | 0.5 | 116.12 |
|  |  |  |  | 0.75 | 105.85 |
|  |  |  |  | 1 | 214.29 |
|  |  |  |  | 1.5 | 193.10 |
|  |  |  |  | 2 | 103.50 |
|  |  |  |  | 4 | 18.42 |
|  |  |  |  | 8 | 2.57 |
|  |  |  |  | 24 | 0.31 |
| 32 | 50.8 mg micronized Zoledronic, DL-lysine, and water complex (1:1:1), with 278.0 mg micronized DL-lysine monohydrate gelatin capsule | PO | n/a | 0 | 0.00 |
|  |  |  |  | 0.0833 | 2.42 |
|  |  |  |  | 0.1667 | 33.98 |
|  |  |  |  | 0.25 | 121.95 |
|  |  |  |  | 0.5 | 212.75 |
|  |  |  |  | 0.75 | 242.80 |
|  |  |  |  | 1 | 221.71 |
|  |  |  |  | 1.5 | 212.75 |
|  |  |  |  | 2 | 126.93 |
|  |  |  |  | 4 | 23.77 |
|  |  |  |  | 8 | 3.64 |
|  |  |  |  | 24 | 0.80 |

TABLE 8

Aqueous solubility of zoledronic acid (ZA) and novel zoledronic acid complexes at room temperature.

| Compound | Conc. mg/mL | mMol/L (complex) |
|---|---|---|
| ZA monohydrate | 1.57 | 5.41 |
| ZA:Glycine | 11.89 | 34.25 |
| ZA:L-Lysine dihydrate | 8.22 | 18.09 |
| ZA:DL-Lysine dihydrate | 6.85 | 15.08 |
| ZA:DL-Lysine monohydrate | 13.9 | 31.86 |

The invention claimed is:

1. A method of treating psoriatic arthritis, said method comprising the step of administering to a psoriatic arthritis patient a therapeutically effective amount of a crystalline molecular complex of zoledronic acid, lysine and water, and an additional lysine apart from the lysine in the crystalline molecular complex,
wherein the lysine is selected from D,L-lysine or L-lysine.

2. A method of treating psoriatic arthritis according to claim 1, wherein the lysine is D,L-lysine.

3. A method of treating psoriatic arthritis according to claim 1, wherein the lysine is L-lysine.

4. A method of treating psoriatic arthritis according to claim 1, wherein the crystalline molecular complex is administered as a pharmaceutical composition comprising the crystalline molecular complex and a pharmaceutical carrier.

5. A method of treating psoriatic arthritis according to claim 2, wherein the crystalline molecular complex is administered as a pharmaceutical composition comprising the crystalline molecular complex and a pharmaceutical carrier.

6. A method of treating psoriatic arthritis according to claim 3, wherein the crystalline molecular complex is administered as a pharmaceutical composition comprising the crystalline molecular complex and a pharmaceutical carrier.

7. A method of treating psoriatic arthritis according to claim 5, wherein the pharmaceutical composition further comprises additional D,L-lysine apart from the D,L-lysine in the crystalline molecular complex.

8. A method of treating psoriatic arthritis according to claim 7, wherein the D,L-lysine is D,L-lysine monohydrate.

9. A method of treating psoriatic arthritis according to claim 6, wherein the pharmaceutical composition further comprises additional L-lysine apart from the L-lysine in the crystalline molecular complex.

10. A method of treating psoriatic arthritis according to claim 4, wherein the pharmaceutical composition is an oral dosage form.

11. A method of treating psoriatic arthritis according to claim 10, wherein the oral dosage form is selected from a tablet and a capsule.

12. A method of treating psoriatic arthritis according to claim 5, wherein the pharmaceutical composition is an oral dosage form.

13. A method of treating psoriatic arthritis according to claim 12, wherein the oral dosage form is selected from a tablet and a capsule.

14. A method of treating psoriatic arthritis according to claim 6, wherein the pharmaceutical composition is an oral dosage form.

15. A method of treating psoriatic arthritis according to claim 14, wherein the oral dosage form is selected from a tablet and a capsule.

16. A method of treating psoriatic arthritis according to claim 4, wherein the pharmaceutical composition is an oral dosage form.

17. A method of treating psoriatic arthritis according to claim 16, wherein the oral dosage form is selected from a tablet and a capsule.

18. A method of treating psoriatic arthritis according to claim 7, wherein the pharmaceutical composition is an oral dosage form.

19. A method of treating psoriatic arthritis according to claim 18, wherein the oral dosage form is selected from a tablet and a capsule.

\* \* \* \* \*